(12) United States Patent
Bloom et al.

(10) Patent No.: US 8,753,290 B2
(45) Date of Patent: Jun. 17, 2014

(54) FLUID TRANSFER SYSTEM AND METHOD

(75) Inventors: Daniel Bloom, Alameda, CA (US); Nicholas A. Nelson, San Francisco, CA (US); Morten J. Jensen, San Francisco, CA (US); Laurence R. Shea, San Francisco, CA (US); Ed Donlon, San Jose, CA (US); Joe Vivolo, San Francisco, CA (US); Stuart Taylor, Santa Clara, CA (US)

(73) Assignee: Intellectual Inspiration, LLC, Austin, TX (US)

( * ) Notice: Subject to any disclaimer, the term of this patent is extended or adjusted under 35 U.S.C. 154(b) by 729 days.

(21) Appl. No.: 12/731,010

(22) Filed: Mar. 24, 2010

(65) Prior Publication Data

US 2011/0077480 A1 Mar. 31, 2011

Related U.S. Application Data

(60) Provisional application No. 61/164,285, filed on Mar. 27, 2009.

(51) Int. Cl.
*A61B 5/00* (2006.01)

(52) U.S. Cl.
USPC .......................................................... 600/584

(58) Field of Classification Search
USPC ................... 600/316, 573, 575, 584
See application file for complete search history.

(56) References Cited

U.S. PATENT DOCUMENTS

| | | | |
|---|---|---|---|
| 2,483,924 A | 10/1949 | Mouliner | |
| 3,340,869 A | 9/1967 | Bane | |
| 3,469,577 A | 9/1969 | Kater | |
| 3,498,899 A | 3/1970 | Kater et al. | |
| 3,539,300 A | 11/1970 | Stone | |
| 3,910,256 A | 10/1975 | Clark et al. | |
| 3,993,049 A | 11/1976 | Kater | |
| 4,077,395 A | 3/1978 | Woolner | |
| 4,094,822 A | 6/1978 | Kater | |
| 4,127,111 A | 11/1978 | Drolet | |
| 4,218,421 A | 8/1980 | Mack, Jr. et al. | |

(Continued)

FOREIGN PATENT DOCUMENTS

| | | |
|---|---|---|
| JP | 06317566 A | 11/1994 |
| WO | WO-91/16416 A1 | 10/1991 |

(Continued)

OTHER PUBLICATIONS

Edwards Lifesciences (2000)."Safe and Accurate Blood Sampling in Surgery and Intensive Care", Edwards Lifesciences LLC (VAMP Plus System) located at: <http://www.edwards.com/NR/rdonlyres/8B42Fa81-225A-4204-BBE3-6ED73A376CC2/0/1141VAMPPlus04Update.pdf>, last visited on Jan. 16, 2008, four pages.

(Continued)

*Primary Examiner* — Max Hindenburg
(74) *Attorney, Agent, or Firm* — Morrison & Foerster LLP

(57) ABSTRACT

Devices and methods for automatic monitoring of fluid of a patient are disclosed, comprising a patient line, a transfer disk which receives the fluid and controllably transfers the fluid to test substrates, and a sensor disk which houses the test substrates. The sterile transfer disk may be configured to maintain the sterility of the patient sampling assembly while transferring samples to non-sterile components, such as the sensor disk.

11 Claims, 49 Drawing Sheets

(56) References Cited

U.S. PATENT DOCUMENTS

| | | |
|---|---|---|
| 4,240,438 A | 12/1980 | Updike et al. |
| 4,258,717 A | 3/1981 | Bisera et al. |
| 4,340,457 A | 7/1982 | Kater |
| 4,411,792 A | 10/1983 | Babb |
| 4,535,786 A | 8/1985 | Kater |
| 4,573,968 A | 3/1986 | Parker |
| 4,608,996 A | 9/1986 | Brown |
| 4,657,027 A | 4/1987 | Paulsen |
| 4,696,309 A | 9/1987 | Stephan |
| 4,743,228 A | 5/1988 | Butterfield |
| 4,786,394 A | 11/1988 | Enzer et al. |
| 4,796,644 A | 1/1989 | Polaschegg |
| 4,838,855 A | 6/1989 | Lynn |
| 4,871,439 A | 10/1989 | Enzer et al. |
| 4,872,813 A | 10/1989 | Gorton et al. |
| 4,878,896 A | 11/1989 | Garrison et al. |
| 4,919,596 A | 4/1990 | Slate et al. |
| 4,928,694 A | 5/1990 | Maxwell |
| 4,934,369 A | 6/1990 | Maxwell |
| 4,951,669 A | 8/1990 | Maxwell et al. |
| 5,002,066 A | 3/1991 | Simpson et al. |
| 5,019,974 A | 5/1991 | Beckers |
| 5,035,704 A | 7/1991 | Lambert et al. |
| 5,037,396 A | 8/1991 | Streeter |
| 5,048,537 A | 9/1991 | Messinger |
| 5,077,010 A | 12/1991 | Ishizaka et al. |
| 5,096,669 A | 3/1992 | Lauks et al. |
| 5,134,079 A | 7/1992 | Cusack et al. |
| 5,135,489 A | 8/1992 | Jepson et al. |
| 5,148,811 A | 9/1992 | Messinger |
| 5,165,406 A | 11/1992 | Wong |
| 5,178,603 A | 1/1993 | Prince |
| 5,195,963 A | 3/1993 | Yafuso et al. |
| 5,216,597 A | 6/1993 | Beckers |
| 5,225,063 A | 7/1993 | Gumbrecht et al. |
| 5,237,993 A | 8/1993 | Skrabal |
| 5,252,213 A | 10/1993 | Ahmad et al. |
| 5,271,815 A | 12/1993 | Wong |
| 5,307,263 A | 4/1994 | Brown |
| 5,325,853 A | 7/1994 | Morris et al. |
| 5,325,867 A | 7/1994 | Skrabal et al. |
| 5,330,634 A | 7/1994 | Wong et al. |
| 5,335,658 A | 8/1994 | Bedingham |
| 5,345,932 A | 9/1994 | Yafuso et al. |
| 5,368,029 A | 11/1994 | Holcombe et al. |
| 5,368,555 A | 11/1994 | Sussman et al. |
| 5,379,764 A | 1/1995 | Barnes et al. |
| 5,380,665 A | 1/1995 | Cusack et al. |
| 5,421,328 A | 6/1995 | Bedingham |
| 5,431,174 A | 7/1995 | Knute |
| 5,462,052 A | 10/1995 | Gehrich et al. |
| 5,505,828 A | 4/1996 | Wong et al. |
| 5,531,672 A | 7/1996 | Lynn |
| 5,536,249 A | 7/1996 | Castellano et al. |
| 5,569,186 A | 10/1996 | Lord et al. |
| 5,582,184 A | 12/1996 | Erickson et al. |
| 5,638,828 A | 6/1997 | Lauks et al. |
| 5,665,065 A | 9/1997 | Colman et al. |
| 5,695,623 A | 12/1997 | Michel et al. |
| 5,697,366 A | 12/1997 | Kimball et al. |
| 5,697,899 A | 12/1997 | Hillman et al. |
| 5,720,924 A | 2/1998 | Eikmeier et al. |
| 5,741,211 A | 4/1998 | Renirie et al. |
| 5,746,217 A | 5/1998 | Erickson et al. |
| 5,747,666 A | 5/1998 | Willis |
| 5,758,643 A | 6/1998 | Wong et al. |
| 5,800,387 A | 9/1998 | Duffy et al. |
| 5,804,048 A | 9/1998 | Wong et al. |
| 5,820,570 A | 10/1998 | Erickson et al. |
| 5,871,494 A | 2/1999 | Simons et al. |
| 5,902,253 A | 5/1999 | Pfeiffer et al. |
| 5,928,880 A | 7/1999 | Wilding et al. |
| 5,932,175 A | 8/1999 | Knute et al. |
| 5,947,911 A | 9/1999 | Wong et al. |
| 5,971,941 A | 10/1999 | Simons et al. |
| 5,976,085 A | 11/1999 | Kimball et al. |
| 6,017,318 A | 1/2000 | Gauthier et al. |
| 6,027,479 A | 2/2000 | Alei et al. |
| 6,036,924 A | 3/2000 | Simons et al. |
| 6,066,243 A | 5/2000 | Anderson et al. |
| 6,071,294 A | 6/2000 | Simons et al. |
| 6,080,116 A | 6/2000 | Erickson et al. |
| 6,099,484 A | 8/2000 | Douglas et al. |
| 6,113,554 A | 9/2000 | Gilcher et al. |
| 6,117,290 A | 9/2000 | Say et al. |
| 6,123,827 A | 9/2000 | Wong et al. |
| 6,128,519 A | 10/2000 | Say |
| 6,175,752 B1 | 1/2001 | Say et al. |
| 6,184,029 B1 | 2/2001 | Wilding et al. |
| 6,188,648 B1 | 2/2001 | Olsen |
| 6,192,891 B1 | 2/2001 | Gravel et al. |
| 6,203,759 B1 | 3/2001 | Pelc et al. |
| 6,233,471 B1 | 5/2001 | Berner et al. |
| 6,251,660 B1 | 6/2001 | Muir et al. |
| 6,272,364 B1 | 8/2001 | Kurnik |
| 6,279,511 B1 | 8/2001 | Loughnane |
| 6,296,615 B1 | 10/2001 | Brockway et al. |
| 6,302,855 B1 | 10/2001 | Lav et al. |
| 6,372,182 B1 | 4/2002 | Mauro et al. |
| 6,375,627 B1 | 4/2002 | Mauze et al. |
| 6,464,849 B1 | 10/2002 | Say et al. |
| 6,472,220 B1 | 10/2002 | Simons et al. |
| 6,484,046 B1 | 11/2002 | Say et al. |
| 6,540,672 B1 | 4/2003 | Simonsen et al. |
| 6,540,890 B1 | 4/2003 | Bhullar et al. |
| 6,541,266 B2 | 4/2003 | Modzelewski et al. |
| 6,546,269 B1 | 4/2003 | Kurnik |
| 6,558,351 B1 | 5/2003 | Steil et al. |
| 6,561,989 B2 | 5/2003 | Whitson |
| 6,565,509 B1 | 5/2003 | Say et al. |
| 6,572,545 B2 | 6/2003 | Knobbe et al. |
| 6,576,101 B1 | 6/2003 | Heller et al. |
| 6,595,919 B2 | 7/2003 | Berner et al. |
| 6,602,205 B1 | 8/2003 | Erickson et al. |
| 6,602,702 B1 | 8/2003 | McDevitt et al. |
| 6,605,471 B1 | 8/2003 | Lundsgaard et al. |
| 6,612,111 B1 | 9/2003 | Hodges et al. |
| 6,645,359 B1 | 11/2003 | Bhullar et al. |
| 6,653,091 B1 | 11/2003 | Dunn et al. |
| 6,656,114 B1 | 12/2003 | Poulsen et al. |
| 6,656,428 B1 | 12/2003 | Clark et al. |
| 6,659,959 B2 | 12/2003 | Brockway et al. |
| 6,666,821 B2 | 12/2003 | Keimel |
| 6,669,663 B1 | 12/2003 | Thompson |
| 6,695,803 B1 | 2/2004 | Robinson et al. |
| 6,736,783 B2 | 5/2004 | Blake et al. |
| 6,740,072 B2 | 5/2004 | Starkweather et al. |
| 6,743,633 B1 | 6/2004 | Hunter |
| 6,749,567 B2 | 6/2004 | Davis et al. |
| 6,755,807 B2 | 6/2004 | Risk, Jr. et al. |
| 6,755,949 B1 | 6/2004 | Bhullar et al. |
| 6,764,462 B2 | 7/2004 | Risk, Jr. et al. |
| 6,768,879 B2 | 7/2004 | Kosuge |
| 6,780,297 B2 | 8/2004 | Matsumoto et al. |
| 6,800,074 B2 | 10/2004 | Henley et al. |
| 6,814,843 B1 | 11/2004 | Bhullar et al. |
| 6,814,844 B2 | 11/2004 | Bhullar et al. |
| 6,824,533 B2 | 11/2004 | Risk, Jr. et al. |
| 6,849,237 B2 | 2/2005 | Housefield et al. |
| 6,866,758 B2 | 3/2005 | Bhullar et al. |
| 6,872,297 B2 | 3/2005 | Mansouri et al. |
| 6,872,358 B2 | 3/2005 | Hagen et al. |
| 6,875,619 B2 | 4/2005 | Blackburn |
| 6,902,703 B2 | 6/2005 | Marquiss et al. |
| 6,911,182 B2 | 6/2005 | Tegeler et al. |
| 6,911,621 B2 | 6/2005 | Bhullar et al. |
| 6,923,764 B2 | 8/2005 | Aceti et al. |
| 6,988,996 B2 | 1/2006 | Roe et al. |
| 7,004,928 B2 | 2/2006 | Aceti et al. |
| 7,022,219 B2 | 4/2006 | Mansouri et al. |
| 7,152,616 B2 | 12/2006 | Zucchelli et al. |
| 7,157,049 B2 | 1/2007 | Valencia et al. |
| 7,162,290 B1 | 1/2007 | Levin |
| 7,179,423 B2 | 2/2007 | Böhm et al. |

(56) References Cited

U.S. PATENT DOCUMENTS

| | | | |
|---|---|---|---|
| 7,198,606 | B2 | 4/2007 | Boecker et al. |
| 7,232,547 | B2 | 6/2007 | Rusch et al. |
| 7,244,232 | B2 | 7/2007 | Connelly et al. |
| 7,244,393 | B2 | 7/2007 | Kaylor et al. |
| 7,258,672 | B2 | 8/2007 | Hansson et al. |
| 7,299,081 | B2 * | 11/2007 | Mace et al. ............... 600/345 |
| 7,303,727 | B1 | 12/2007 | Dubrow et al. |
| 7,338,802 | B2 | 3/2008 | Frischauf et al. |
| 7,378,270 | B2 | 5/2008 | Azarnia et al. |
| 7,524,293 | B2 * | 4/2009 | Freeman et al. ............ 600/583 |
| 7,892,185 | B2 * | 2/2011 | Freeman et al. ............ 600/583 |
| 8,070,692 | B2 * | 12/2011 | Ghesquiere et al. ......... 600/583 |
| 2003/0191415 | A1 | 10/2003 | Moerman et al. |
| 2004/0138688 | A1 | 7/2004 | Giraud |
| 2005/0214881 | A1 | 9/2005 | Azarnia et al. |
| 2006/0188407 | A1 | 8/2006 | Gable et al. |
| 2006/0235348 | A1 | 10/2006 | Callicoat et al. |
| 2006/0278537 | A1 | 12/2006 | Cai et al. |
| 2006/0281187 | A1 | 12/2006 | Emery et al. |

FOREIGN PATENT DOCUMENTS

| | | |
|---|---|---|
| WO | WO-02/080762 A1 | 10/2002 |
| WO | WO-02/100254 A2 | 12/2002 |
| WO | WO-02/100254 A3 | 12/2002 |
| WO | WO-03/080166 A1 | 10/2003 |
| WO | WO-2004/047642 A1 | 6/2004 |
| WO | WO-2004/052204 A1 | 6/2004 |
| WO | WO-2004/056269 A1 | 7/2004 |
| WO | WO-2007/137285 A2 | 11/2007 |
| WO | WO-2007-137285 A3 | 11/2007 |

OTHER PUBLICATIONS

Edwards Lifesciences (2002) "Edward VAMP and VAMP Jr. Systems," located at: <http://www.edwards.com/Products/PressureMonitoring/VAMPSystemBrochurePDF.htm>, last visited on Jan. 16, 2008, four pages.

Genexel-Sien, Inc. (2006) "Introducing Duo-Care Combined Blood Glucose and Wrist Blood Pressure Monitor," located at: www.duo-care.com/01product.html <http://www.duo-care.com/01product.html>, last visited on Jan. 2, 2008, one page.

International Preliminary Report on Patentability mailed on Dec. 16, 2008, for PCT Application No. PCT/US2006/045642, filed on Nov. 28, 2006, seven pages.

International Preliminary Report on Patentability mailed on Nov. 28, 2008, for PCT Application No. PCT/US/2007/069546, filed on May 23, 2007, five pages.

International Preliminary Report on Patentability mailed on Nov. 28, 2008, for PCT Application No. PCT/US2007/069542, filed on May 23, 2007, five pages.

International Preliminary Report on Patentability mailed on Jun. 12, 2008 for PCT Application No. PCT/US06/045359, filed on Nov. 27, 2006, six pages.

International Search Report mailed on Jun. 10, 2008, for PCT Application No. PCT/US07/69542, filed on May 23, 2007, one page.

International Search Report mailed on May 23, 2007, for PCT Application No. PCT/US06/24167, filed on Jun. 20, 2006, one page.

International Search Report mailed on Aug. 27, 2007, for PCT Application No. PCT/US06/45359, filed on Nov. 27, 2006, one page.

International Search Report mailed Sep. 24, 2007, for PCT Application No. PCT/US06/45440, one page.

Lifescan, Inc. (Dates from 1996-2006). "OneTouch Lancing Devices," located at: <http://lifescan.com/products/lancing>, last visited on Jan. 2, 2008, three pages.

Lifescan, Inc. (Dates from 1996-2006). "OneTouch SureStep Test Strips for use with OneTouch Surestep Meters", located at: <http://www.lifescan.com/products/teststrips/surestep>, last visited on Jan. 2, 2008, two pages.

Lifescan, Inc. (2001). "Lifescan Makes Getting Accurate Glucose Results Perfectly Easy," located at: <http://www.lifescan.net/pdf/hospital/ss_technology.pdf>, last visited on Jan. 16, 2008, five pages.

Lifescan, Inc. (2002). "OneTouch SureStep Blood Glucose Monitoring System Owner's Manual," located at: <http://www.lifescan.com/pdf/ss_ob.pdf>, last visited on Jan. 2, 2008, eighty-four pages.

Non-Final Office Action mailed on Aug. 18, 2008, for U.S. Appl. No. 11/288,031, filed Nov. 28, 2005, seven pages.

Roche (2008) "Accu-Chek Compact Plus DiabetesTest Strips," located at: <http://www.accu-chek.com/us/rewrite/generalContent/en_US/articie/ACCM_general_article_2656.htm>, last visited on Jan. 14, 2008, two pages.

Via Medicial Corporation (Dates from 1988-1998). "Study on On-Line Hematocrit and Glucose Analysis Animal Study," Infusion Pump FDA documents submitted by Via Medical Corporation, one hundred and eighty-four pages.

* cited by examiner

Section A-A

Section B-B

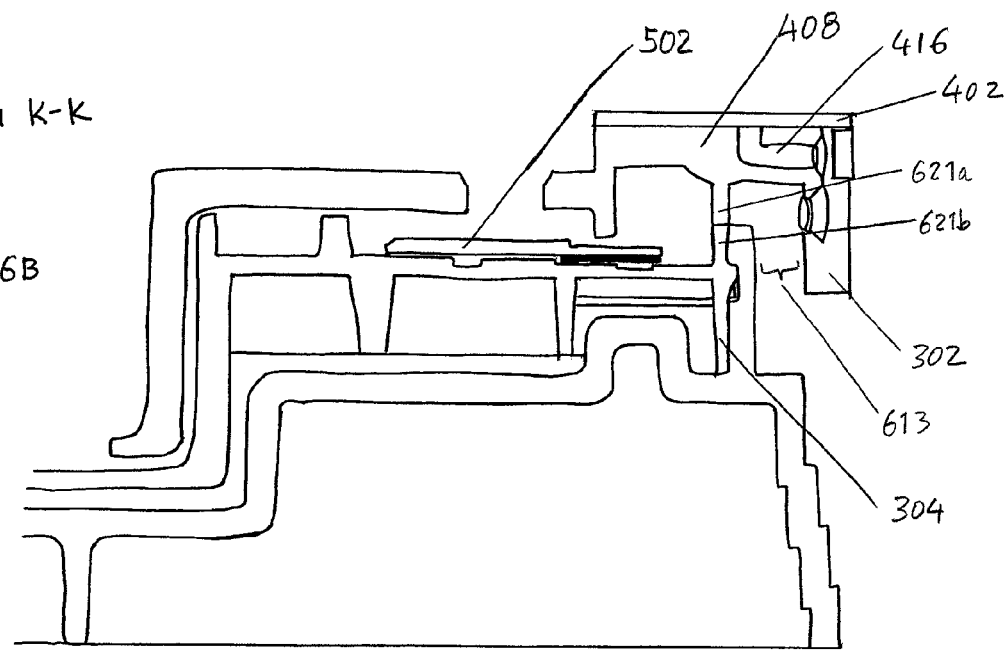
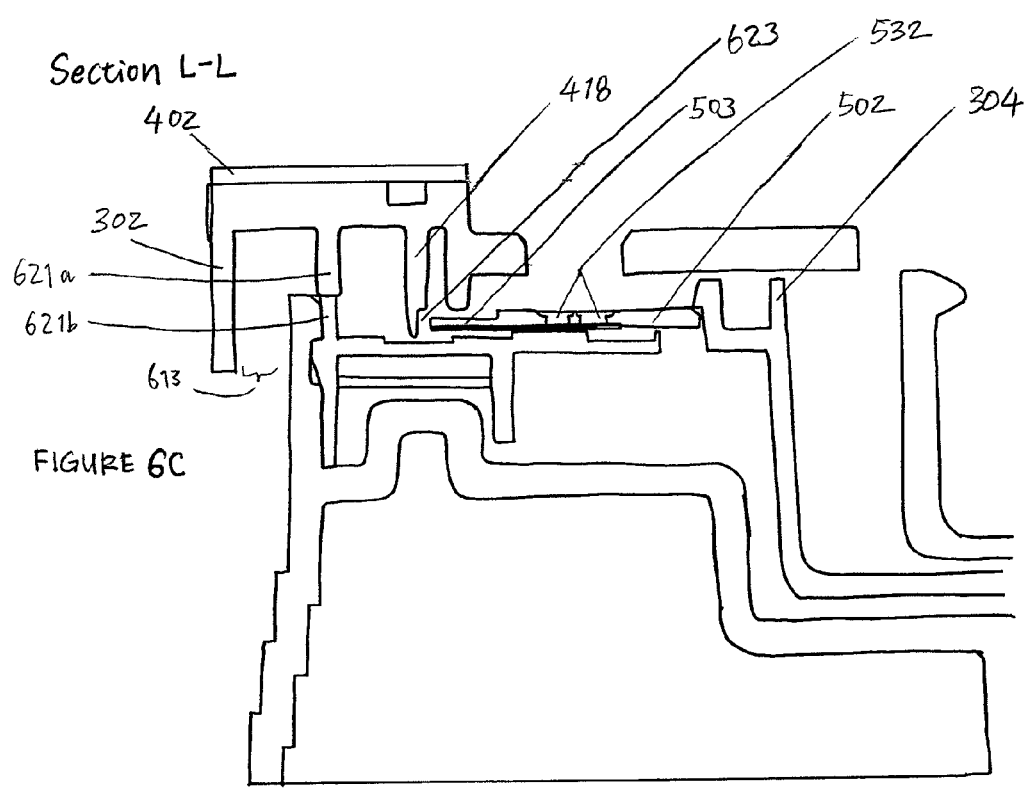

FLUID TRANSFER SYSTEM AND METHOD

CROSS-REFERENCE TO RELATED APPLICATIONS

This Application claims benefit under 35 U.S.C. §119(e) to U.S. Provisional Ser. No. 61/164,285, filed on Mar. 27, 2009, which is hereby incorporated by reference in its entirety.

BACKGROUND

In the health-care industry, diagnostic testing of physiological or biological samples, such as blood, is a routine, and often cumbersome, task, with physicians requiring a wide variety of specialized tests on patients' samples to support their diagnoses. With in-patient and critical care settings, the frequency of blood sampling places additional demands on hospital staff.

To satisfy this ever increasing demand for analytical data from samples, sophisticated chemical analyzers have been developed over the past 20 years to perform a multiplicity of physical and chemical tests on specially prepared patients' samples. Sample volume requirements have also been reduced substantially, to 100 µL or less for some tests.

BRIEF SUMMARY

Devices and methods for automatic monitoring of fluid of a patient are disclosed, comprising a patient line, a transfer disk which receives the fluid and controllably transfers the fluid to test substrates, and a sensor disk which houses the test substrates. The sterile transfer disk may be configured to maintain the sterility of the patient sampling assembly while transferring samples to non-sterile components, such as the sensor disk.

One embodiment of a fluid sensor device may comprise at least one transfer reservoir, wherein each transfer reservoir comprises an inlet, and outlet, and a cavity comprising a displaceable region and a light-reflecting structure. The transfer device may also comprise at least one alignment structure associated with each transfer reservoir.

Certain variations of a fluid sensor device may also comprise a plurality of transfer reservoirs located in a transfer structure. Other variations may comprise a plurality of test substrates that are located inside a sensor structure, and/or outside the transfer structure. In some embodiments, the sensor structure is configured to attach to the transfer structure.

One embodiment of a fluid sensor device may comprise a plurality of transfer reservoirs, where each reservoir may comprise an optically transmissive material, an inlet opening, an outlet opening, and a cavity comprising a deformable wall and a light-reflecting structure, as well as a plurality of alignment structures, wherein at least one alignment structure is associated with each transfer reservoir.

In some embodiments of a fluid transfer reservoir, the deformable walls of the plurality of transfer reservoirs are deformable membranes. Optionally, the cavities of the plurality of transfer reservoirs further comprise a fixed wall. Certain embodiments of a fluid transfer reservoir are located in a circular transfer housing wherein the inlet openings of the plurality of transfer reservoirs are located on the outer circumferential surface of the circular transfer housing. In some embodiments, the transfer housing may be a circular transfer cartridge.

Additionally, the fluid sensor device may further comprise a sensor housing interface, wherein the interface may comprise an alignment structure and at least one locking structure. The sensor housing interface may further comprise a plurality of sensor substrate access apertures. In some embodiments, the fluid sensor device may further comprise a sensor cartridge comprising a transfer cartridge interface complementary to the sensor cartridge of the transfer cartridge. Certain embodiments of the fluid sensor device also comprise a plurality of test sensors.

Some embodiments of the sensor cartridge further comprise a plurality of fluid sample receiving regions, a plurality of sensor substrates and a plurality of sensor electrode contacts. The plurality of fluid sample receiving regions are oriented to correspond to inlet openings of transfer reservoirs when the transfer cartridge and sensor cartridge are attached.

Another variation of a fluid monitoring system may comprise a patient access interface configured to receive fluid from a patient, a fluid pump configured to transfer fluid in the patient access interface, and a valve coupled to the patient access interface and the fluid pump and comprising a fluid dispensing opening, wherein the valve is configured to dispose a fluid sample at the fluid dispensing opening and a fluid inlet blocking structure adjacent to the fluid dispensing opening.

The patient access interface, fluid pump, valve, and fluid inlet blocking structure are coupled to a patient line housing. In some embodiments, the fluid monitoring system further comprises an external fluid access interface configured to receive fluid from an external fluid source.

Several methods may be employed to monitor the fluid of a patient, for example, the method may comprise withdrawing fluid from a patient into a first housing coupled to a fluid monitoring system, transferring a fluid sample from the withdrawn fluid in the first housing to a second housing, changing the orientation of the second housing relative to the first housing, pumping the fluid sample from the second housing to a test substrate. Pumping the fluid sample from the second housing to the test substrate may comprise pumping the fluid sample across an air gap between a fluid opening of the second housing and the test substrate. In other variations, pumping the fluid sample from the second housing to the test substrate may comprise pumping the fluid sample from the second housing to a third housing, wherein the test substrate is located in the third housing. The method may further comprise wiping a dispensing region of the second housing, and may comprise blocking an opening of the second housing using the first housing.

Other methods for performing fluid monitoring in a patient may comprise transferring fluid along a first fluid pathway from a patient to a fluid dispenser, transferring a fluid sample from the fluid dispenser to a transfer reservoir along a second fluid pathway, severing the second fluid pathway by displacing the transfer reservoir, and actively transferring at least a portion of the fluid sample from the transfer reservoir to a test substrate along a third fluid pathway. The method may further comprise crossing an air gap between the transfer reservoir and the test substrate with the fluid sample. In some variations, at least portion of the cross-sectional shape of the fluid sample is unrestrained in a transverse plane along a movement axis of the third fluid pathway.

An alternate method for performing blood monitoring of a patient may comprise withdrawing blood from a patient into a fluid control system, dispensing a blood sample from the sterile fluid control system to a sterile transfer reservoir, and transferring the blood sample from the sterile transfer reservoir to a non-sterile test substrate. The method may comprise moving the sterile transfer reservoir with respect to the fluid control system after dispensing the blood sample, wherein moving the sterile reservoir occurs before transferring the blood sample. Transferring the blood sample may comprise pumping the blood sample from the sterile transfer reservoir to a non-sterile test substrate.

BRIEF DESCRIPTION OF THE DRAWINGS

FIG. 2M-1 illustrates one variation of the dispense nozzle shape.

FIGS. 2N-2O depict a sequence of fluidic connections that may be used by the fluid monitoring system during initialization, sample collection, and sample dispensing.

FIGS. 5F-5J depict various aspects of the sensor disk and sensor interface.

FIGS. 6A-6D depict various aspects of the interface between a transfer disk and sensor disk.

DETAILED DESCRIPTION

Figure 1:
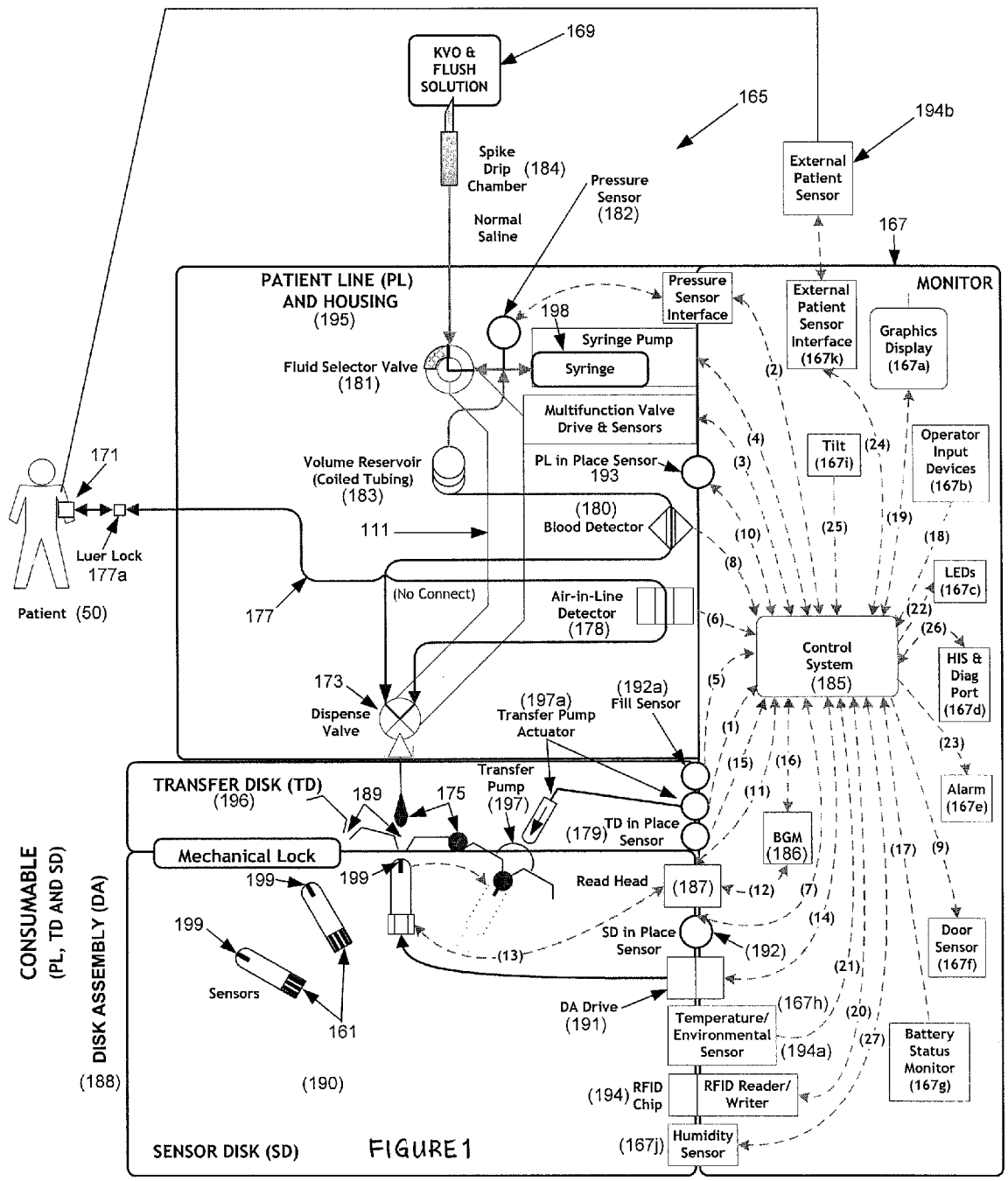
FIG. 1 depicts a fluid monitoring system used to monitor blood glucose levels in a patient.

FIG. 1 schematically depicts one embodiment of an automated fluid monitoring system. In this particular embodiment, the fluid monitoring system is a blood monitoring system (165), but in other embodiments, a fluid monitoring system may be used with other body fluids or organ systems. The blood monitoring system (165) may be organized into several components: a patient line (PL) and housing assembly (195), a monitor assembly (167), a transfer and sensor element such as disk assembly (188), and a flush and KVO ("keep vein open" or "keep vessel open") fluid system (169). The patient line and housing assembly (195), which may also be called the patient access line (PAL) and housing assembly, comprises a fluid access device (171) attachable to the patient (50) and a series of fluid channels or pathways connecting the fluid access device (171) to a fluid sample dispenser or dispense valve (173), a pump (198), fluid system and other components. The fluid access device (171) may be configured to access any of a variety of sites, including but not limited to peripheral and central vascular access sites, arterial and venous vascular sites, lymphatic sites, urinary tract sites, cerebral spinal fluid sites in the spine and cranium, intraabdominal and intrapleural fluid sites, etc.

A transfer element is a portion of the system that is configured to transfer (either directly or indirectly through an intermediary) a sample from a patient line to a sensor element. A sensor element is a portion of the system that is configured to sense at least one parameter of a transferred sample. One embodiment of a transfer and sensor element is disk assembly (188) in FIG. 1, comprising a transfer disk (196) and a sensor disk (190) which includes a plurality of test sensors (161) with test substrates (199). The transfer disk (196) may be locked into engagement with sensor disk (190) when in use. Once locked together, the transfer disk (196) and sensor disk (190) may not be separated so that they cannot be reused and are generally disposed of together after use. In other embodiments, the transfer and sensor element may be an assembly of cassettes, cartridges, or may be enclosed in a single housing. The transfer element or transfer disk, or sensor element or sensor disk may comprise a variety of shapes and/or configurations of test sensors or test substrates not limited to a disk shape.

The transfer disk (196) in FIG. 1 provides a plurality of fluid sample cavities or conduits (189) that separate and transport a fluid sample (175) from the fluid sample dispenser (173) to a test sensor substrate (199) of the sensor disk (190). The transfer disk (196) further comprises a plurality of transfer pumps (197) each corresponding to a conduit or cavity (189) and configured to pump a sample from the conduit or cavity to a corresponding test substrate. According to some embodiments, the transfer pumps comprise deformable members which communicate with the conduit or cavity (189). An enclosed cavity containing a sample opens towards a test substrate (199). Upon deformation of the transfer pump (197), the sample is pumped, displaced, transported or pushed towards a test substrate (199). A pump actuator (197a) may be separately controlled. In some embodiments, e.g., as illustrated, the pump actuator is located on the monitor (167) and may be mechanical or electrical in nature. It communicates via interface 1 with the control system (185).

By using a transfer disk (196) instead of directly dispensing a fluid sample (175) to the test substrate (199), the risk of contamination spreading or bridging back from the non sterile sensor disk (190) to the sterile (or non-contaminated) patient line and housing assembly (195) or the patient (50) may be reduced. Also, by providing sterile, single-use intermediate structures between the fluid sample dispenser (173) and the test substrates (199), the test substrates (199) do not require sterilization themselves, which may improve the shelf-life, operating range, and/or operating performance of the chemicals or reagents, if any, comprising the test substrates (199).

After transferring a fluid sample (175) to the sensor disk (190), the fluid sample (175) may react with the chemicals, reagents, or other components of a test substrate (199) and the resulting end product is produced in proportion to the analyte level in the fluid sample, which can then be analyzed by the monitor assembly (167) to determine the analyte level or other fluid parameter measurements. In the particular embodiment depicted in FIG. 1, the blood monitoring system (165) is configured to measure blood glucose using a blood glucose monitor ("BGM") assembly of the monitor assembly (167), but in other embodiments, other analyte or parameter measurement components may be provided in addition or in lieu of the BGM.

As mentioned previously, the transfer disk and/or sensor disk may comprise any of a variety of designs, including but not limited to drums, carousels, clips, cassettes, or any other module configured to interface or insert into another component. In some embodiments, the patient line and housing assembly (195), the flush and KVO fluid system (169), and/or the monitor assembly (167) may also be in a cartridge or other swappable or modular form factor. In some embodiments, two or more components may be integrated into a single chassis or structure. In some embodiments, for example, the transfer disk (196) and the sensor disk (190) may be integrated into a single cartridge (disk assembly (188)), while in other embodiments, the patient line and housing assembly (195) may be integrated with one or more components of the flush and KVO fluid system (169).

As depicted schematically in FIG. 1, the patient line and housing assembly (195) comprises a main access line (177) from which fluid may be withdrawn and/or infused with respect to the patient (50). The main access line may include a luer lock (177a) that may be connectable to a variety of types of fluid access devices (171) or catheters such as peripherally inserted venous catheters, peripherally inserted central catheters, central venous catheters, or arterial lines. Accordingly the system may be adaptable to connect to a catheter or other blood access device already positioned in the patient. In this particular embodiment, the main access line (177) includes an air in line detector (178). The air in line detector (178) may be useful for safety purposes to make sure that during any infusion or reinfusion procedures through the main access line (177), limited air is being infused. The patient line and housing assembly (195) may include a bubble removal port which can be used to manually remove air bubbles or take fluid samples from the patient line fluid circuit. The air in line detector (178) may be an optical, acoustic, chemical, or impedance-based detector, but any other detector design may also be used.

The fluid dispenser (173) is used to dispense a fluid sample or fluid droplet to the transfer disk. In the particular embodiment depicted in FIG. 1, the fluid sample dispenser (173) is a dispense valve, but in other embodiments, the fluid sample dispenser (173) may comprise a membrane or a spray nozzle, for example. The fluid sample dispenser (173) may be combined into one unit with a fluid selector valve (181) as represented by bracket (111) in FIG. 1. Fluid dispense valve (173) and fluid selector valve (181) may be combined in a way that permits certain connection configurations while prohibiting others. For example, the configuration of the dispense-selector combination valve that allows the volume reservoir (183) to be connected to the dispense valve nozzle would simultaneously prevent any fluid connections between the syringe and the KVO flush solution. The dispense-selector combination valve may be arranged in any way to permit or prohibit fluid connections as required by the operation of the fluid monitoring system.

The fluid sample dispenser (173) is connected to an optional blood detector (180). The blood detector (180) may be used by the monitor assembly (167) to determine whether blood has been adequately withdrawn from the patient (50). For example, the monitor assembly (167) may use blood detection as a pre-condition for dispensing a fluid sample from the fluid sample dispenser (173). This may be necessary to ensure that non-diluted blood has reached the fluid sample dispenser (173) because the patient line may be filled with flush solution prior to withdrawing a patient sample. Also, in some instances, flow resistance and/or clotting may reduce the blood flow in the blood monitoring system (165). By providing a blood detector (180), the action of the pump (198) may be adjusted to compensate for changes in fluid flow and/or to provide a warning signal. In some instances, the monitor assembly (167) may be configured to cease operation or initiate an unclogging or other corrective procedure when certain operating states are identified by the blood detector (180) or air in line detector (178), for example. This is described in U.S. application Ser. No. 11/386,078, which is hereby incorporated by reference in its entirety. The blood detector may be an optical blood detector, a chemical-based, acoustic-based, impedance-based, or other type of detector. The fluid sample dispenser (173) also comprises an actuator or motor for controlling the configuration or state (e.g. open or closed) of the dispenser (173), and may also include one or more sensors that may be used to detect dispenser malfunction or to provide feedback to control valve function.

The blood detector (180) is connected to a fluid selector valve (181) which is in fluid communication with a pressure sensor (182). The fluid selector valve (181) is configured to selectively provide communication between two or more of its ports. In this embodiment, the pressure sensor (182) is shown positioned between the syringe (198) and the valve (181). Various embodiments of the fluid selector valve are described in greater detail below. In the particular embodiment depicted in FIG. 1, the fluid selector valve (181) in combination with the dispense valve (as indicated by bracket (111)) comprises at least five ports. However, in other embodiments, a greater or less number of ports and/or valves may be provided and/or used. A pressure sensor (182) is positioned in the tubing that runs between the syringe (198), selector valve (181) and volume reservoir (183), but in other embodiments, one or more pressure sensors may be connected in other locations in proximity to the fluid selector valve (181), may be integrated with the syringe pump, or may be positioned in-line along other portions of the blood monitoring system (165) including but not limited to at the catheter or fluid access site (171). As depicted, the ports of the fluid selector valve (181) are connected to a pump (198) and a flush and KVO solution (169). An optional fluid reservoir (183) is also provided between the pressure sensor (182) and the blood detector (180). In some instances, the fluid reservoir (183) may be used to ensure that a sufficient volume within the patient line fluid circuit exists to ensure that samples from the patient are not able to contact the pump (198), pressure sensor (182) or fluid selector valve (181). In other instances, the fluid reservoir (183) may act as a sump which may reduce the precision needed for one or more processes. In some embodiments, an additional port may be provided for a waste disposal line or component. The waste disposal line may be used, for example, for expelling clots or bubbles in the blood monitoring system (165), and/or for clearing certain types of fluids out of the fluid lines. The waste disposal may take blood saline mixture out that is created when blood is drawn. This may be used in particularly fluid sensitive patients or to avoid infusing excess solution back into a patient. In one specific example, the blood monitoring system (165) may include a cleansing solution that is periodically infused into the system to resist biofilm buildup and/or clot formation but is preferably not infused into the patient. The waste disposal line may be used to expel the cleansing solution from the system, along with additional flush solution, from the fluid channels before restarting any KVO infusion or fluid sampling. In other embodiments, a separate waste disposal line and/or valve may be provided elsewhere along the system.

The fluid selector valve (181) and/or the fluid sample dispenser (173) may be manipulated by the monitor assembly (167) using any of a variety of actuating mechanisms. These mechanisms include but are not limited to a stepper motor, servo motor or electromagnetic motor. The motor may be electric, hydraulic, pneumatic or magnetic-based, or electromagnetic, for example.

The pump (198) connected to the fluid selector valve (181) may be any of a variety of pumps, including but not limited to a syringe pumps, piston pumps, diaphragm pumps, peristaltic pumps, and the like. The pump (198) may be bidirectional or multidirectional. The pump (198) may be disposable. The pump (198) may comprise an opening with which fluid may be withdrawn and infused. In other embodiments, however, separate inlet and openings may be provided.

In the particular embodiment illustrated in FIG. 1, a single solution source is provided, comprising a flush and KVO solution (169) to be used with the flush and KVO solution set (169). The solution source may be connected to the blood monitoring system (165) using a spike drip chamber (184) which is used with standard intravenous fluid bags, but in other embodiments, any of a variety of other fluid connectors may be used and multiple fluid sources for multiple fluids or solutions may be used. The solutions that may be used with the blood monitoring system (165) include but are not limited to distilled water, normal saline, half-normal saline, D5W, and Lactated Ringer's solution. In some embodiments, the solution may contain one or more additives, including but not limited to heparin, a heparinoid, potassium, magnesium, sodium bicarbonate, multi-vitamin solution, anti-infectives such as antibiotics and anti-fungal agents, for example, provided the solution does not significantly interfere with the analyte to be measured or provided the solution can be adequately be compensated for when the analyte is measured.

The flush and KVO solution set (169) may be used to infuse intravenous fluids into the patient (50) in between blood sampling procedures. It may also be used to open an occlusion or venous valve to improve blood draw. As noted previously, the flush and KVO solution bag or source may be accessed using a spike drip chamber (184) or other type of access device. Although characterized as a "Keep-Vein-Open" solution set, higher infusion rates may be provided also. For example, typical KVO (or TKO "To-Keep-Open") infusion rates are about 50 mL/hour or less, but infusion rates greater than 50 mL/hour may be provided. The higher rates may be about 75 mL/hour, about 100 mL/hour, about 125 mL/hour, about 150 mL/hour, or more. The infusion rate may be an average rate or may be delivered as a bolus or a plurality of boli over a period of time.

The monitor assembly (167) comprises a control system (185) or programmable logic controller that is configured to receive and process sensor information and to control and coordinate a variety of processes performed by the blood monitoring system (165). The control system (185) receives data from a blood glucose monitor ("BGM") (186) through a BGM interface (16) which receives data from read head (187) via interface (12). The BGM interface (16) and other interfaces of the system (165) may be unidirectional (e.g. input or output only, such as receiving data from the BGM) or bi-directional (e.g. receiving data and transmitting control signals to initiate a warm-up procedure or enter calibration or maintenance mode, or to transmit other data, such as control system, environmental, patient, or situational data, necessary for the user or practitioner). The BGM (186) may be configured to directly or indirectly analyze the test substrate (199). In the embodiment depicted in FIG. 1, a read head (187) which is part of the monitor (167) is positionable with respect to disk assembly (188), to read the test substrate (199) and to communicate the control system (185). According to some embodiments, an access opening is provided for positioning the read head (187) adjacent the test substrate (199). The interface (13) may be a connector or a set of electrical contacts which allows the read head to read from test substrate (199) when coupled thereto. The interface (11) allows the control system (185) to control operation of the read head (187). The BGM (186) may alternatively communicate with any other system which would provide an intermediate structure between the dispense valve (173) and the test substrates (199) or that would allow reading of the test substrate (199) and communication with the control system (185). According to some embodiments, a humidity sensor (167j) is mounted in the monitor (167) adjacent to the sensor disk (190). The humidity sensor communicates to control system (185) via interface (27) which then may adjust the blood glucose reading based on sensing humidity or humidity over time and corresponding sensor sensitivity level. The humidity sensor (167j) may also provide humidity sensor reading or readings that indicate that a sensor is no longer sufficiently sensitive or accurate thus signaling replacement of the disk assembly (188) is required. According to some embodiments, the sensor life and/or accuracy and/or precision is determined at different humidity levels. A curve is created of the life or accuracy or precision of the sensor based on humidity. Humidity at the sensor is monitored before and during use. The humidity is integrated over time where the integration is weighted depending on the sensitivity at the different humidity levels. When the integrated humidity reaches a level determined to be the limit where the sensor no longer produces acceptable results, the monitor indicates replacement is necessary. Alternatively, the monitor may adjust the output reading to compensate for the humidity effects.

A disk assembly drive (191) is provided having an actuating mechanism (e.g. a motor with a rotor) that provides movement and positioning of the disk assembly (188) with respect to the monitor (167) (including positioning of read head (187) and transfer pump actuator (197a), with respect to a transfer pump (197) of a transfer conduit or cavity (189) of the disk assembly (188)). The disk assembly drive (191) advances, rotates, pivots or otherwise manipulates the disk assembly (188) to select the desired conduit or cavity (189) of the transfer disk (196) and corresponding test substrate (199) of the sensor disk (190), into and out of a dispensing position with respect to the fluid sample dispenser (173). The disk assembly drive (191) provides for control and selection of disk assembly (188) positions for purposes including but not limited to dispensing to transfer conduit or cavity (189), wiping or blotting the dispenser (173) with a wipe positioned on the disk assembly (188), separating individual components from each other or contacting individual components with each other, or initiating a test sensor reading as well as checking test sensor use status. In some embodiments, the interface (14) may also allow the disk assembly drive (191) to transmit signals to the control system (185) indicative of various operating parameters, for example position of the disk assembly (188). The disk assembly drive may be composed of a single acting mechanism driven directly or indirectly by but not limited to a stepper motor, servo motor, or DC motor. Alternatively the drive assembly may be comprised of two or more assemblies, such as but not limited to a cam to provide pivoting action and a spindle to provide rotary motion. Such mechanism may be actuated by solenoids, DC motors, servo motors, or stepper motors.

In the embodiment depicted in FIG. 1, the monitor assembly (167) further comprises a electrical interface (4) between the control system (185) and the pump (198). The configuration of the software may vary, depending upon the desired functionality. For example, the software may be configured to control the pump (198) based upon plunger motion rate, plunger force, plunger home position, plunger end position or any position therebetween. The electrical interface may comprise any type of standardized interface, or a proprietary interface. For some components, an analog/digital converter may be provided in the component itself, the signal interface and/or the control system (185). In embodiments comprising an optional infusion pump for one or more fluid sources connected to the blood monitoring system (165), an infusion pump interface may also be provided.

The monitor assembly (167) may also comprise a distribution valve interface (3) (or interface with multifunction valve, a combination of distribution valve (181) and dispense valve (173)), which transmits control signals to the mechanical drive of the multi-port distribution valve or fluid selector valve (181), and optionally transmits valve position information back to the control system (185). A unidirectional or bidirectional interface may also be provided for the fluid sample dispenser (173) to transmit control signals and dispenser position information.

In embodiments comprising a stand-alone inline pressure sensor or a pressure sensor integrated with the multi-port distribution valve or fluid selector valve (181), a pressure sensor interface (2) is provided to transmit pressure sensor information to the control system (185). Other data input interfaces that may be provided include but are not limited to the air detector interface (6) and the blood detector interface (8).

In some embodiments, the monitor assembly (167) is configured with sensors to detect the coupling and/or proper seating of one or more components of the blood monitoring system (165). For example, a patient line in place sensor (193) may be provided to detect whether the patient line and housing assembly (195) is in place. The control system (185) may use the sensor (193) to check the status of the patient line and housing assembly (195) before proceeding with its operation, or with certain maintenance or corrective procedures. In some embodiments, a releasable PL lock between the patient line and housing assembly (195) and the monitor assembly (167) may be provided. The releasable PL lock may form a mechanical interlock with the PL and housing assembly (167) which is electronically releasable to prevent removal of the patient line and housing assembly (195) during operation or during certain procedures, and which may protect the clinician, patient (50), and/or the blood monitoring system (165) from damage. The transfer disk (196) may also be provided with a transfer disk in place sensor (179) which communicates with the control system (185) through signal interface (15). The sensor disk (190) may also be provided with a sensor disk in place sensor (192) which communicates with the control system (185) through signal interface (7). An optional sensor or communication interface may be provided between the PL and housing assembly (195) and the disk assembly to confirm alignment between the two components. Specific examples of the interface between the disk assembly (188), the patient line and housing (195), and other components are described below and also described in U.S. application Ser. No. 12/057,245, which is hereby incorporated by reference in its entirety.

In addition to detecting and identifying the placement of modules in the blood monitoring system (165), a fill sensor (192a) provided to detect when a cavity or conduit (189) has reached maximum fill level. Conduit (189) may also be a cavity, conduit, tube, well, sample reservoir, or other structure that may be used to retain or contain a fluid sample. This prevents over and under fill of the transfer conduit so that it is assured that the fluid sample from the patient does not over fill the conduit and bridge to a non-sterile component before the dispense valve (173) is withdrawn from contact with the transfer disk (196). In addition, the fill sensor may provide feedback that the well has been filled adequately by the pump so as to ensure successful transfer of fluid from the transfer disk to the test substrate or test sensor. In addition, the pressure sensor may be used prior to dispensing to determine if the fluid is at a pressure is stable and/or close to ambient pressure or offset from ambient pressure by a given amount thus providing a more controlled or reliable dispense of fluid.

A variety of sensors may be used including, e.g. an optically transmissive, optically reflective, electrically conductive or capacitive sensor. The sensors may be separate elements, a plurality of elements, and/or may be integral with the disk. The test sensor may be single use. It may be pre-calibrated, e.g. to permit ease of use. A control solution, e.g., of a known analyte concentration, may be positioned in one of the test sensor locations and may be used to determine at time of used of sensor element the efficacy of the sensors. For example, if the sensitivity of a sensor has changed during transportation, or over time, the sensor reading may be compared with sensitivity that is input into the RFID tag at time of manufacture, packaging or transport. The sensor readings may be corrected accordingly or an indication may be provided if the sensor disk should be replaced. The fill sensor (192a) may communicate via interface (15) with control system (185). The fill sensor (192a) communicates with the control system via interface (5).

In addition to detecting and identifying the placement of modules in the blood monitoring system (165), door sensors (167f) may also be provided to detect when one or more access doors of the system (165) have been opened. In some embodiments, detection of open access doors may stop or limit operation to protect against danger to the patient, the clinician, or to the equipment or warn the user to close the door to maintain the integrity of the chamber within the monitoring system (165).

In some embodiments, one or more components or modules of the blood monitoring system (165) may comprise machine readable indicia that may be relayed to the control system (185) using an indicia reader and may be used to provide information concerning the particular component or module. The indicia reader may be, for example, a barcode reader, a radiofrequency ID (RFID) chip reader (194a), and/or an electrical connection to an EPROM or other chip located on one of the consumable components (e.g., the transfer disk, sensor disk or patient line). The machine readable indicia may comprise graphical indicia such as a barcode, or intangible indicia such as an RFID chip (194). In some embodiments, the information may comprise serial numbers or arbitrary identification information that may be compared to a database within the control system (185) to confirm that the correct type of cartridge was inserted, and/or to configure the blood monitoring system (165). In other embodiments, the machine readable indicia may include configuration information, such as calibration curves or threshold values that may be used to configure the control system (185) and/or BGM (186) without utilizing a look-up database. With the latter embodiments, the software of the control system (185) does not require updating in order to utilize a new type of test substrate cartridge, because the configuration and/or calibration information may be provided through the machine readable indicia. In some embodiments, the monitoring system (165) may be configured so that the machine readable indicia of a cartridge or module may be read by the control system (185) before the cartridge is fully seated and locked into place. If the control system (185) identifies the particular cartridge or module as an incorrect module (e.g. wrong patient, incompatible with the particular PL and housing assembly (195) or with the selected monitoring function), in some embodiments, the control system (185) may control the module locks to block their seating or insertion into the monitoring system (165), or by rejecting via a screen alarm is detected after seating in place. In some embodiments, the control system (185) may comprise a separate indicia writer, or a writing function may be integrated into the indicia reader. The writing function may permit, for example, an RFID chip to be programmed to flag the cartridge as having been used, with or without patient information or for patient-specific, operational use, or error information to be written to the RFID chip for later analysis, documentation, or troubleshooting by the user or manufacturer. The writing function may also prevent inadvertent use of an incorrect cartridge or module. In other embodiments, the writing function may be provided by barcode printer which prints and applies printing, e.g. inkjetting, a new barcode on the cartridge or module.

In addition to the interfacing with other components of the blood monitoring system (165), the monitor assembly (167) may further comprise one or more subcomponents for interfacing with medical staff, medical information systems or other extrinsic systems. In the embodiment depicted in FIG. 1, these subcomponents may include a graphics display of text (167*a*) and/or pictorial information (e.g. graphical plots) of patient related information and/or system status information, other types of indicator lights (167*c*) (e.g. LEDs), operator input devices (167*b*) (e.g. keyboard, touch screen, joystick, mouse, buttons, dials, bar code reader), a hospital information system port (167*d*) (e.g. for transmitting information to a remote patient monitor at a nursing station and/or for storing results in an electronic medical record), one or more external patient sensors (194*b*) communicating with an external sensor interface (167*k*) (e.g. wirelessly or through a connection or other intermediate communication device), a diagnostic port to perform maintenance updates or diagnostic checks of the system or software, environmental sensors (167*h*) (e.g. temperature, barometric pressure detectors), auditory/visual/tactile alarms for patient/environmental/system-related warnings/fault states (167*e*), and power/battery status monitors or sensors (167*g*). Data interfaces (9, 10, 17, 18, 19, 20, 21, 22, 23, 24, 25 and 26) may be provided for the respective components. The data interfaces for these components may be unidirectional or bidirectional. The data interface (26) for the hospital information system port, for example, may transmit patient and/or system data out of the port, but may also receive data from the external information system (e.g. signal to change system function, or to alter the type or presentation of patient and/or system data). The external patient sensor may include a sensor apparatus that is configured to sense or determine one or more parameter corresponding to a patient or patient treatment, such as, e.g., patient temperature or limb temperature, heart rate, pulse, EKG, blood pressure, respiration rate, blood gas level (e.g., oxygen or carbon dioxide, e.g., via pulse oximetry or an indwelling catheter), Hematocrit, blood viscosity, drug type, drug dosing or infusion rates, or other parameters. The sensed patient parameter and/or environmental, room temperature, humidity information may be used to adjust patient draw parameters, adjust glucose or other measurements made at sensor disk or to improve accuracy or precision of readings by the blood glucose or other analyte monitor.

In some embodiments, one or more of the subcomponents may provide instructions or instructional indicia to a person, for example, to perform a check or other procedure (e.g. check for a clog or air in the fluid line, replace empty IV bag or test sensor cartridge). In some embodiments of the blood monitoring system where the manipulation of fluid samples or fluid droplets is gravity dependent, the monitor assembly (167) may comprise a tilt detector (167*i*) which may provide a warning when the system (165) is not adequately level, or may even provide specific auditory and/or visual instructions to adjust specific feet, or supports of the system, up or down to achieve the desired leveling. In other embodiments, the control system may comprise motors or other mechanisms to automate procedures such as leveling, cartridge change or IV bag change, for example.

Patient Line and Housing

Figure 2A:
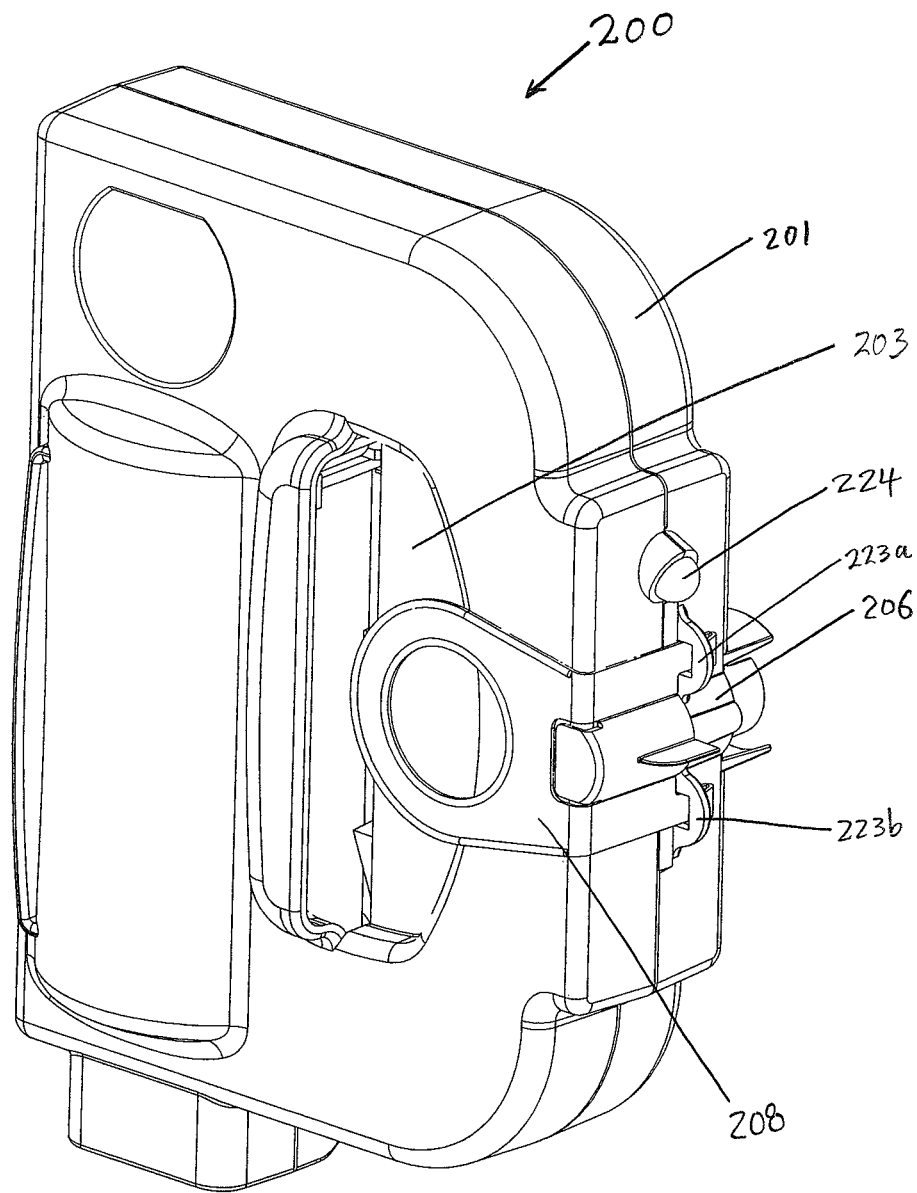
FIGS. 2A-2C depict one embodiment of the housing of a patient line (PL) cartridge.
Figure 2B:
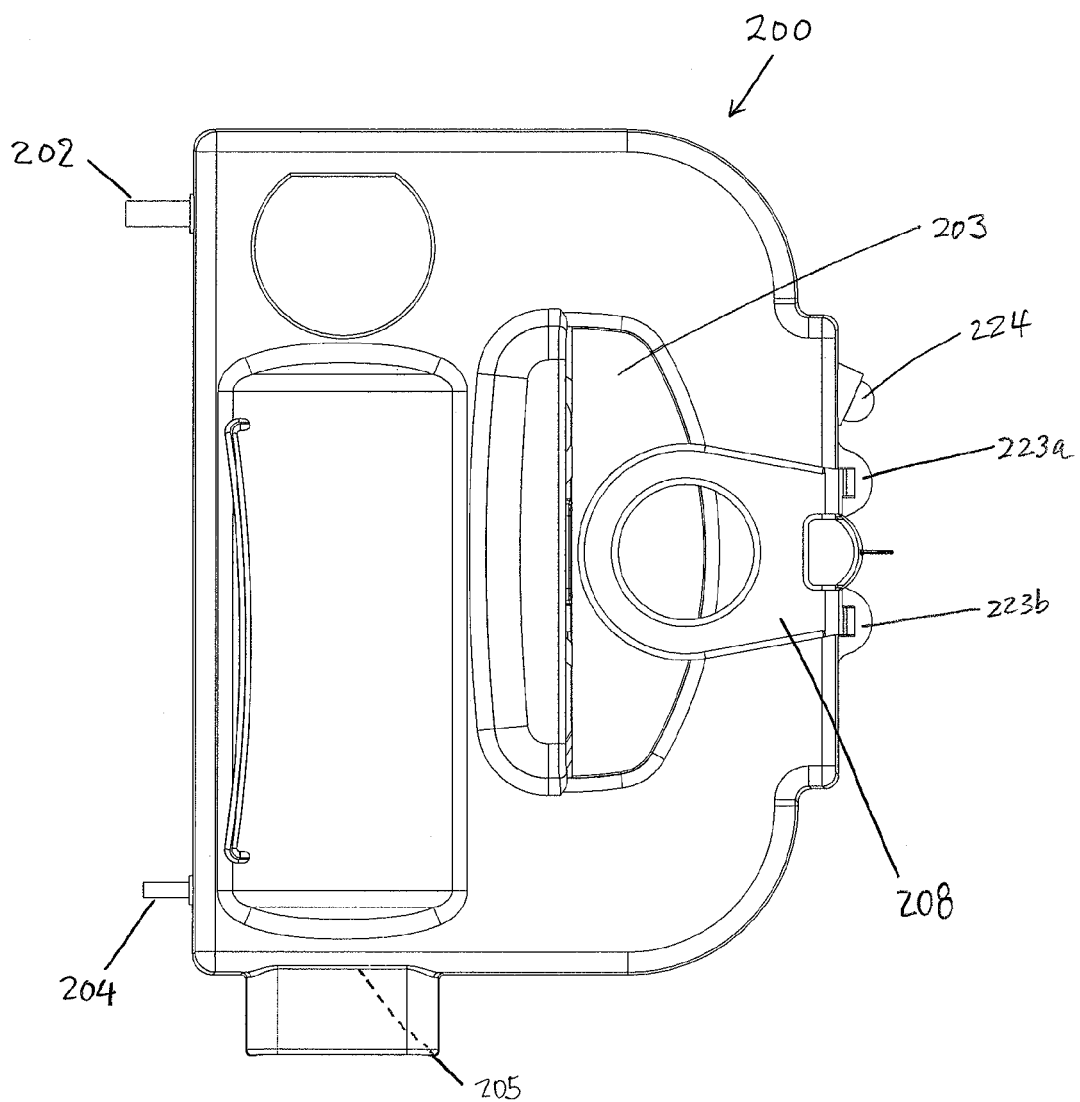

As mentioned previously, certain components of the fluid monitoring system may be provided in removable housings and/or cartridges, which may facilitate replacement of disposable components and/or sterilization of reusable components. A cartridge may refer to any unit, cassette, drum, or assembly of parts, which may be enclosed in a housing. Some variations of the patient line and housing (195) in FIG. 1 may comprise a number of system components found between the patient and the sensor substrate. One specific embodiment of a PL and housing (200) is shown in FIGS. 2A and 2B. The housing (201) is made of a co-polyester blend, but may be made of any material with similar properties, such as polycarbonate or acrylic. PL cartridge (200) may comprise one or more connectors that transfer fluid in and/or out of the cartridge. Here, fluid connectors (202) and (204) are provided to connect PL cartridge (200) to components of the fluid monitoring system, such as the KVO and flush solution reservoir (169), or the fluid access device (171), which is attached to the patient (50). In other embodiments, additional connectors may be provided for additional fluid lines, separate flush solutions, optional waste circuits, and/or intravascular hemodynamic monitoring sensors, for example. A dispensing valve (206) transfers fluid samples obtained from the patient (50) to the other components of system, such as the transfer cartridge or sensor cartridge that are described in greater detail below. The PL cartridge (200) may also comprise other structures which may facilitate or coordinate fluid transfer to the other components or between other components, such as the fluid channel plug (224), which is described in greater detail below.

PL cartridge (200) may comprise several alignment features. These alignment features may be used to ensure correction positioning and alignment with respect to other system components. For example, alignment protrusions (207*b*) and (207*d*) may be used to mechanically align the PL cartridge to the monitor during installation and use. In some embodiments, mechanical interlock features may be temporary, so that the PL cartridge may be removed and/or disposed after use. Apertures may also be provided for alignment, which are described in detail below.

Figure 2C:
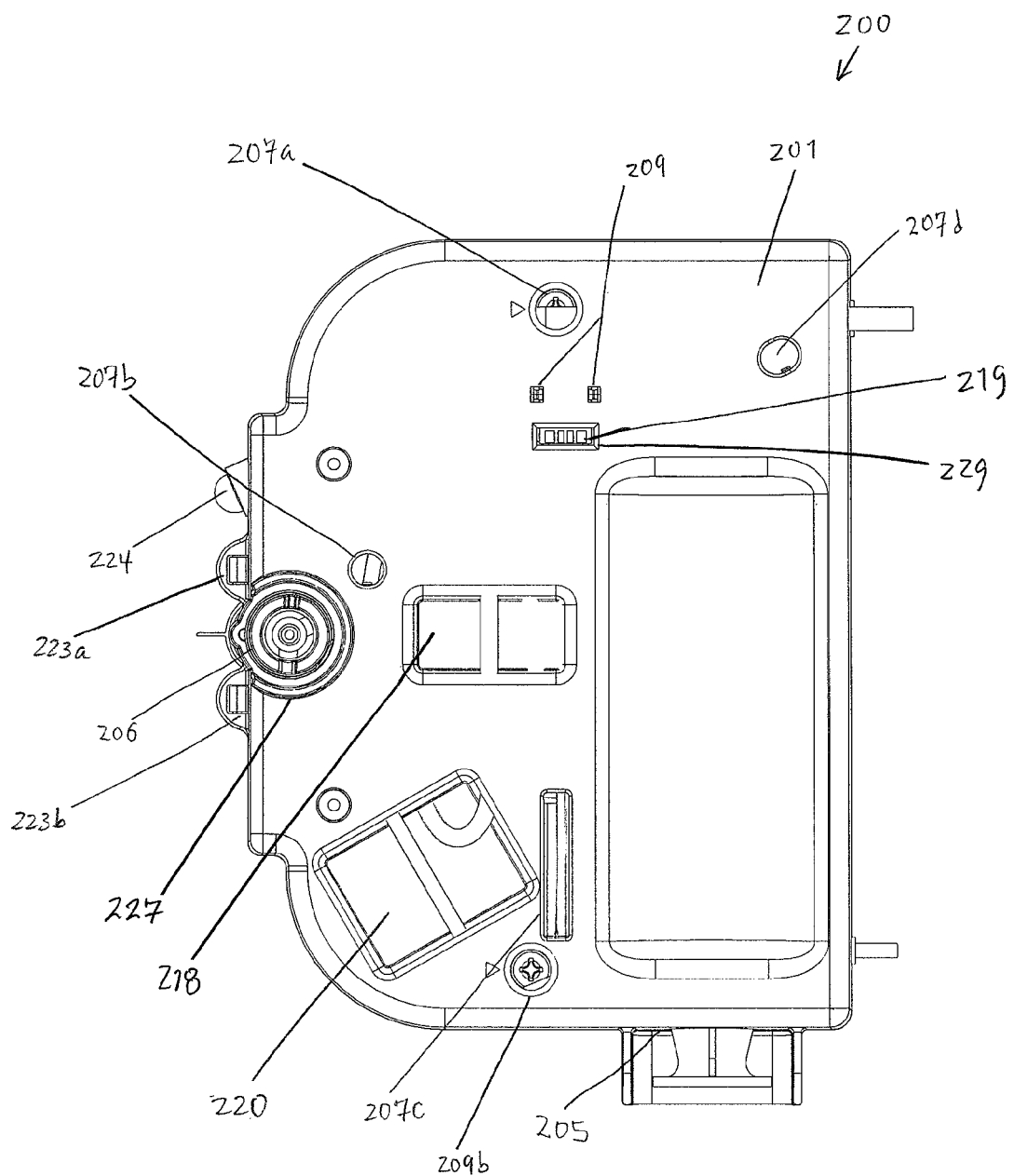

PL cartridge (200) may comprise mechanical and electrical interfaces that allow the fluid monitoring system to control and acquire data from certain components within the PL cartridge (200) and acquire data from the cartridge (200). There may be various apertures in the housing (201), for example, aperture (203) which may facilitate the handling of the PL cartridge (200). Aperture (205) may be sized and shaped to permit the insertion and actuation of a pump, for example, a syringe pump. Additional apertures may be included to allow actuators to manipulate the components of PL cartridge (200) for example, as described in some variations herein. In some variations, there may be apertures that allow mechanical sub components within the PL cartridge to manipulate external structures. Some variations of the PL cartridge may comprise apertures in the back of the housing (201), as shown in FIG. 2C. These apertures (227, 218, 220, 229) may provide access to the internal components of the PL cartridge, as well as engage with alignment protrusions. For example, apertures (227, 218, 220, 229) may allow sensors (e.g. optical sensors) to access the contents of the fluid channels in the housing (201). In some variations, access apertures (227, 218, 220, 229) may be located in the front of the housing (201). Apertures (207b) and (207d) may form a mechanical interface with protrusions on the fluid monitoring system, to align and secure the PL cartridge within the system. Access apertures (227, 218, 220, 229) may also be used to aid in debugging the PL cartridge (200) if a malfunction occurs. Assembly apertures, for example, holes (207a) and (209b), may be provided as junction points to secure multiple components together. Holes (207a) and (209b) may be sized and shaped to accommodate screws and connectors to secure the components of PL cartridge (200).

The PL cartridge (200) may also comprise an electrical interface that provides power to the components in the cartridge. This electrical interface may also allow commands to be issued from the control system (185) to the PL cartridge, and for data readings (e.g. from various sensors) to be transmitted back to the control system. For example, control system (185) may probe an internal sensor (e.g. a pressure sensor) using an electrical interface (219), as shown in FIG. 2C. Different sensors may use a variety of interfaces, e.g., any standard or proprietary interface, electrical or otherwise, to communicate between the PL cartridge and the control system, as shown in FIG. 1.

The connectors, apertures, and electrical interfaces described above may be covered prior to their installation and use within the fluid monitoring system. For example, cover (208) may be locked onto the PL cartridge prior to installation by attaching to retention features (223a) and (223b), and may only be unlocked when properly installed in the fluid monitoring system. Covers may also be temporarily attached to the housing (201) by adhesives, hook-and-loop fasteners, static cling, or any suitable bonding method. The covers may be rigid or flexible, depending on its material composition. Covers (e.g. cover (208)) may optionally be used to align the PL cartridge during assembly and installation. Some variations of the PL cartridge (200) may include such covers to reduce contaminants from entering the apertures, protect connectors and other protruding features from damage, and to guard against device tampering. Other fluid monitoring system components, such as the disposable elements, may also comprise such covers.

Figure 2D:
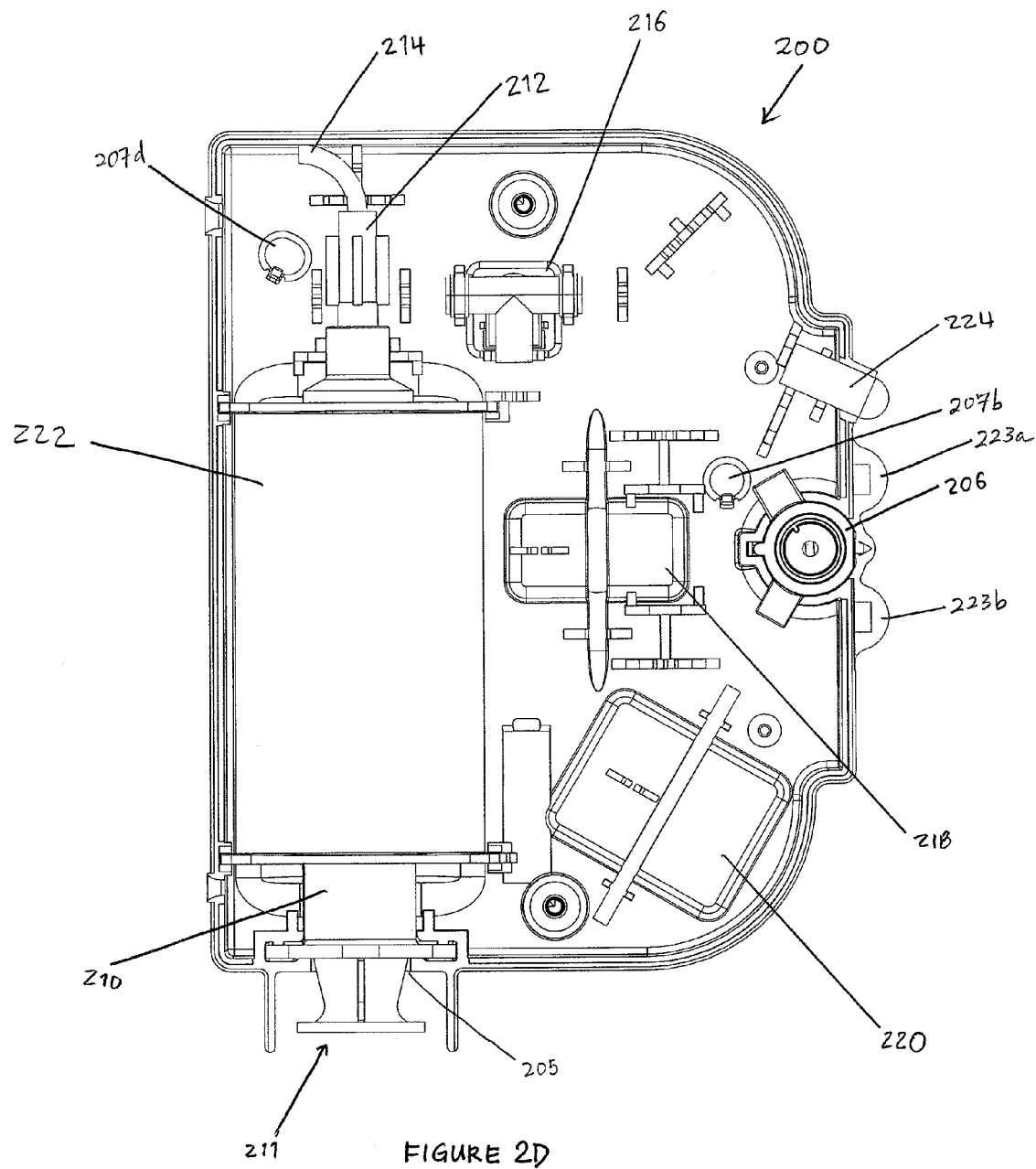
FIGS. 2D-2F depict the arrangement of fluidic devices in the PL cartridge of FIGS. 2A-2C.
Figure 2E:
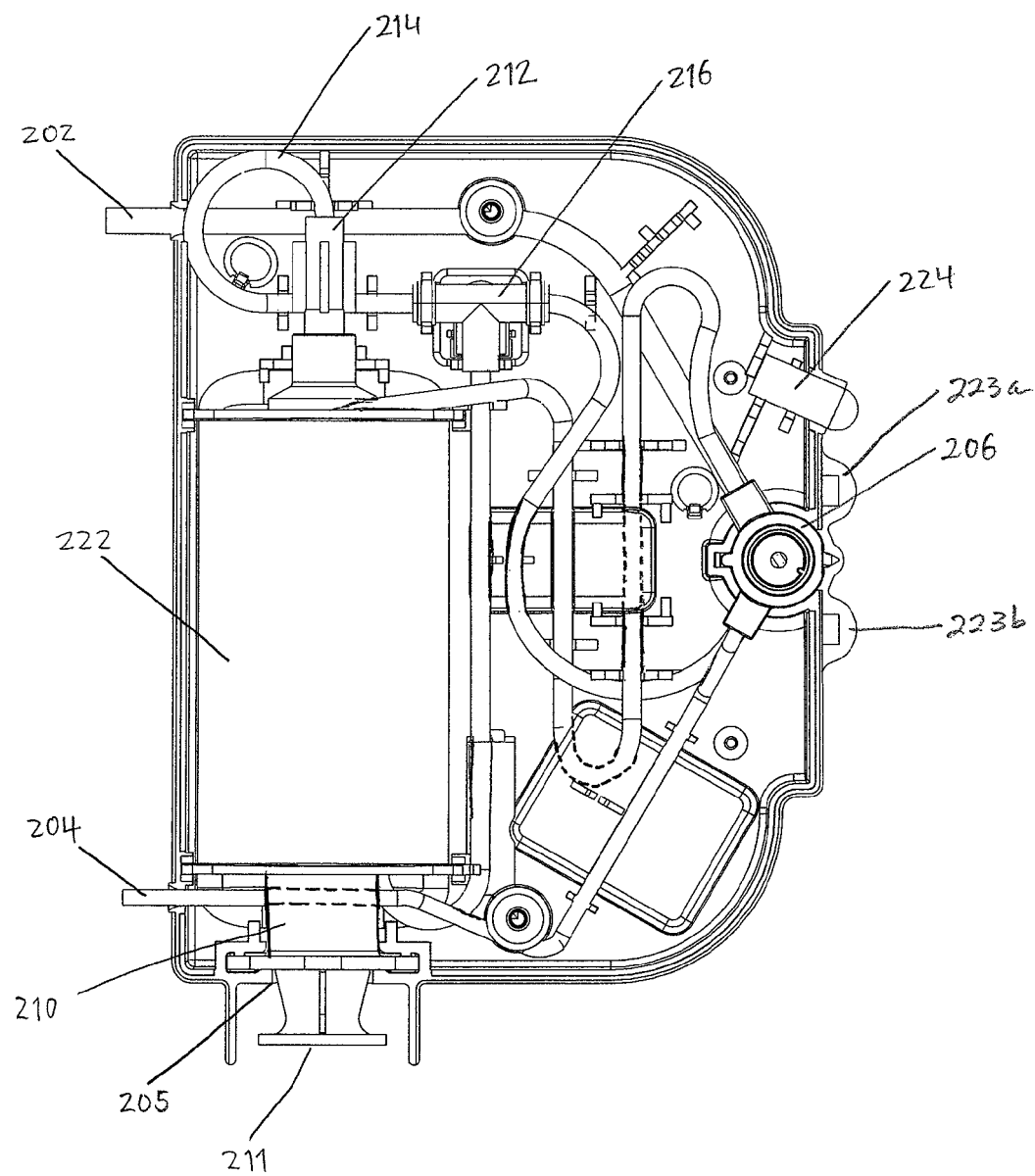
Figure 2F:
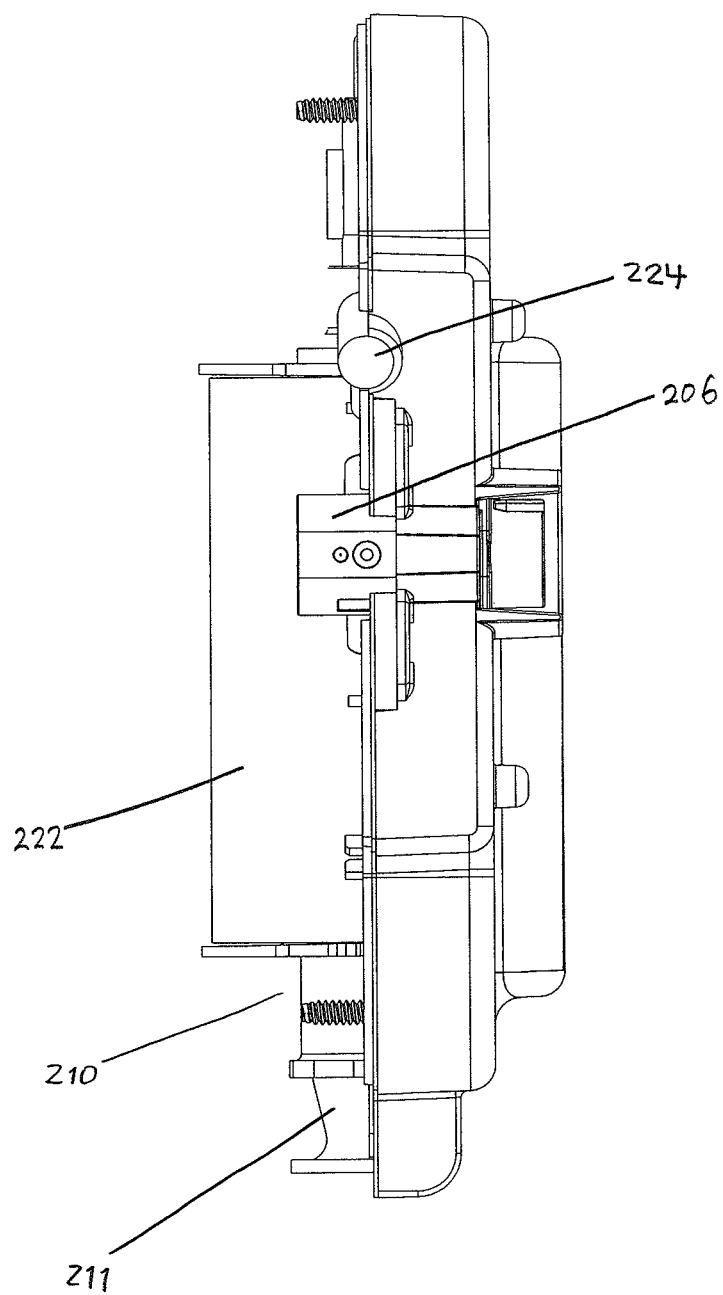

Referring to FIGS. 2C and 2D, the fluid flow between the patient and the sensor substrate may be managed using any number of tubes, valves, connectors, and pumps arranged in any suitable configuration. In PL cartridge (200), the fluid-regulating system comprises a pump (210), tubing (214), a pressure sensor (216), fluid reservoir (222), and fluid dispensing or multiplexing valve (206). These fluidic devices may be placed in any suitable position in the PL cartridge, an example of which is shown in FIG. 2D. These devices may also be interconnected by a tubing assembly (214) in any suitable configuration, as shown in FIG. 2E. In certain variations, connector (202) and the tubing running from it may connect the KVO and/or flush solution (169) to the multiplexing valve (206). Connector (204) and the associated tubing may connector the patient device (171) to the multiplexing valve (206). The tubing assembly (214) may also provide connectivity between the pump (210) and the fluid reservoir (222) and multiplexing valve (206). Tubing assembly (214) may also provide connectivity between the fluid reservoir (222) and the multiplexing valve (206). While the tubing assembly (214) provides general connectivity between these fluidic devices, the fluid connections may change during the use of the monitoring system and is managed by the control system (185). The control system may actuate the multiplexing valve (206) to select for certain fluid connections, and may also actuate the pump (210) to encourage fluid flow to or from the connected components.

Syringe Pump

The fluid flow through the PL cartridge (200) may be controlled by a variety of pumps, for example, infusion pumps, centrifugal pumps, piston pumps, diaphragm pumps, syringe pumps, peristaltic pumps, and the like. In one variation of a PL cartridge, a syringe pump (210) is used to regulate fluid flow, as shown in FIG. 2D. The plunger (211) of the syringe pump may extend out of the housing through aperture (205) and may be actuated by either an external or internal component, such as a lever or motor, which is controlled by the control system (185). The size of the syringe (210) may vary as needed. For example, a syringe pump in a blood monitoring system that monitors one blood analyte may need to regulate 5-10 mL of blood. A syringe pump in a blood monitoring system that monitors multiple blood analytes or process several fluids may need to regulate more than 10 mL of blood. The pressure gradient created by the syringe (210) may be used to move fluid into, out of, and within the tubing assembly (214). For example, the pressure gradient created by the syringe pump (210) may be used to draw fluid from (or pump fluid to) an external fluid source, such as the patient (50) or the KVO solution (169). The syringe pump (210) may also be used to move fluid from the fluid reservoir (222) to the multiplexing valve (206). In certain variations, the syringe pump may be sterilized prior to installation and use, and made of materials that can withstand the sterilization procedure, such that reliability is not compromised. The interface between the pump and the fluid tubing may vary depending on the pump type. For example, a luer lock (212) may act as the junction between syringe pump (210) and PL cartridge tubing assembly (214), however any locking interface that is fluid-tight (either through a locking mechanism or by bonding) may be used. In the variation of the PL cartridge shown in FIGS. 2D and 2E, the body of the syringe pump (210) is enclosed by the fluid reservoir (222), however, the pump (210) may be positioned elsewhere, and not necessarily enclosed by the fluid reservoir (222).

Fluid Reservoir

Certain variations may have a fluid reservoir (222). In some instances, the fluid reservoir (222) is used to ensure that sufficient volume within the PL fluid circuit exists to ensure that samples from the patient are not able to contact the pump (210), pressure sensor (216), or other components. Alternatively, fluid reservoir (222) may act as a sump and reduce the precision needed for one or more processes. The fluid reservoir may be of any suitable configuration such that an excess of fluid may be stored therein and readily drawn for testing. In some variations, the fluid reservoir may be a container, and in other variations, the fluid reservoir may be an extension of tubing assembly (214), for example, a coil of tubing. As shown in FIG. 2E, the fluid reservoir is connected by the tubing assembly (214) to the multiplexing valve (206) and the pressure sensor (216), however in other variations, the fluid reservoir may be connected to any number of PL cartridge components in any suitable way. Fluid reservoir (222) and PL cartridge tubing (214) may be manufactured from any of a variety of biocompatible material, such as a variety of polymers (e.g. PVC, polycarbonate, polyethylene, polypropylene, polyurethane, silicone, etc) and/or metal alloys (e.g. stainless steel, Nitinol, cobalt chrome, etc), and may optionally be medical grade and sterile. In some variations, tubing assembly (214) and/or reservoir (222) may be pre-molded from polymeric or metallic materials. The interior of tubing assembly (214) and reservoir (222) may be formed to facilitate fluid flow. For example, the interior of the tubing and the reservoir may contain microstructures that reduce fluid resistance and drag. The interior may also be coated with an agent (e.g. an anti-thrombotic agent) to reduce the likelihood of tube obstructions, and/or reduce the friction of the internal surface of the tube.

Blood Sensor, Air-in-Line Sensor and Humidity Sensor

In some variations, several types of sensors may be used with the PL cartridge, including but not limited to optical sensors. As described previously and shown in FIG. 1, a fluid monitoring system may include sensors that detect the presence of fluid or air in the tubing, or sensors that may discern one fluid from another. For example, in a blood monitoring system, there may be blood detectors (180) and air-in-line sensors (178). In other variations, there may be a sensor that detects specific analytes in the blood and can detect blood hematocrit. Furthermore, there may be a sensor that determines when whole, undiluted blood has reached a specific point in the fluid circuit. In some embodiments, this sensor may be an optical blood sensor, though alternate devices and methods may be used to detect whole, undiluted blood. These sensors are accommodated either within the PL or in the fluid monitoring system external to the cartridge. External sensors (such as optical sensors) may access the environment in PL cartridge and the fluid sample through access apertures, such as the ones described in FIG. 2C (apertures (218), (220), and (229)). Non-optical sensors that detect temperature, humidity, and the like may also be used to measure any number of conditions in the PL cartridge. The data from these sensors may be transmitted to the control system (185) so that the appropriate parameters may be adjusted according to the changing conditions.

Pressure Sensor

Figure 2G:
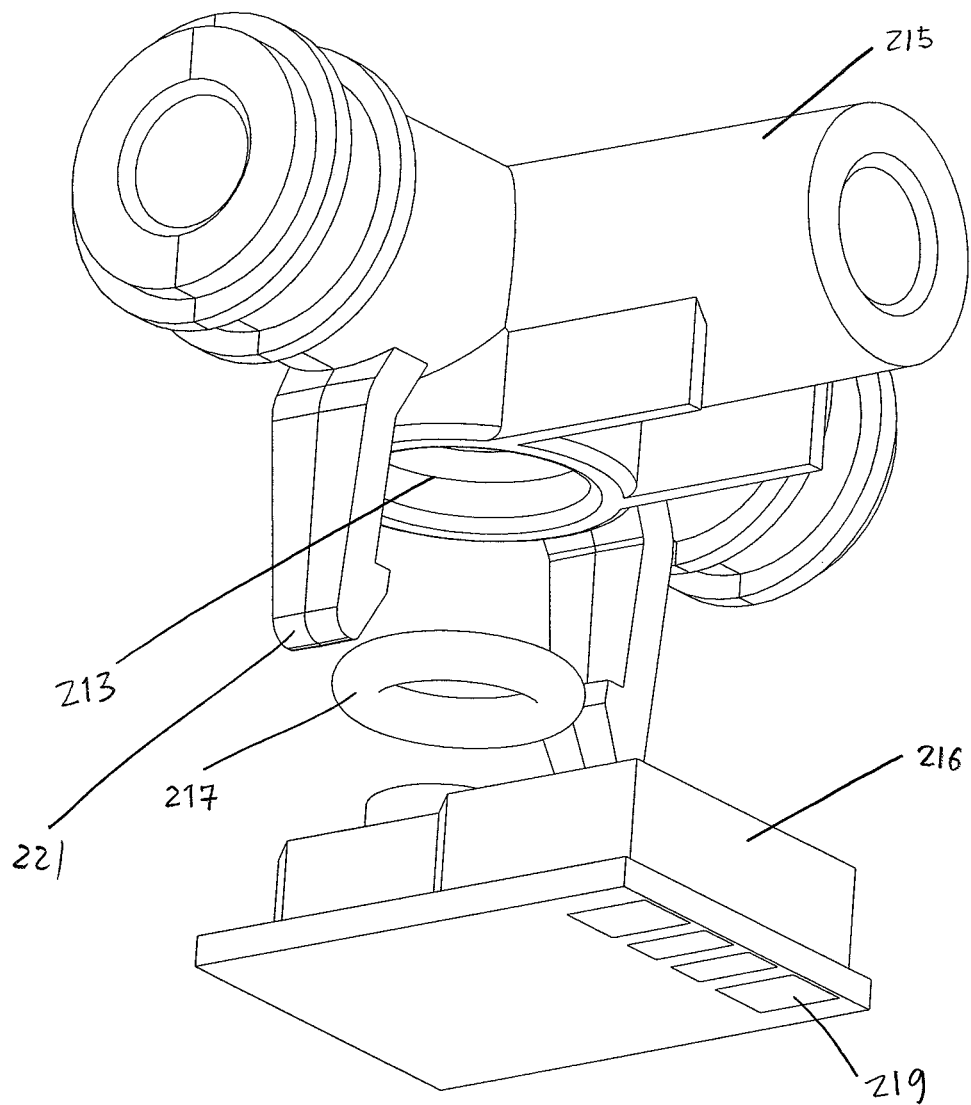
FIGS. 2G-H depict one embodiment of a pressure sensor used in the PL cartridge.
Figure 2H:
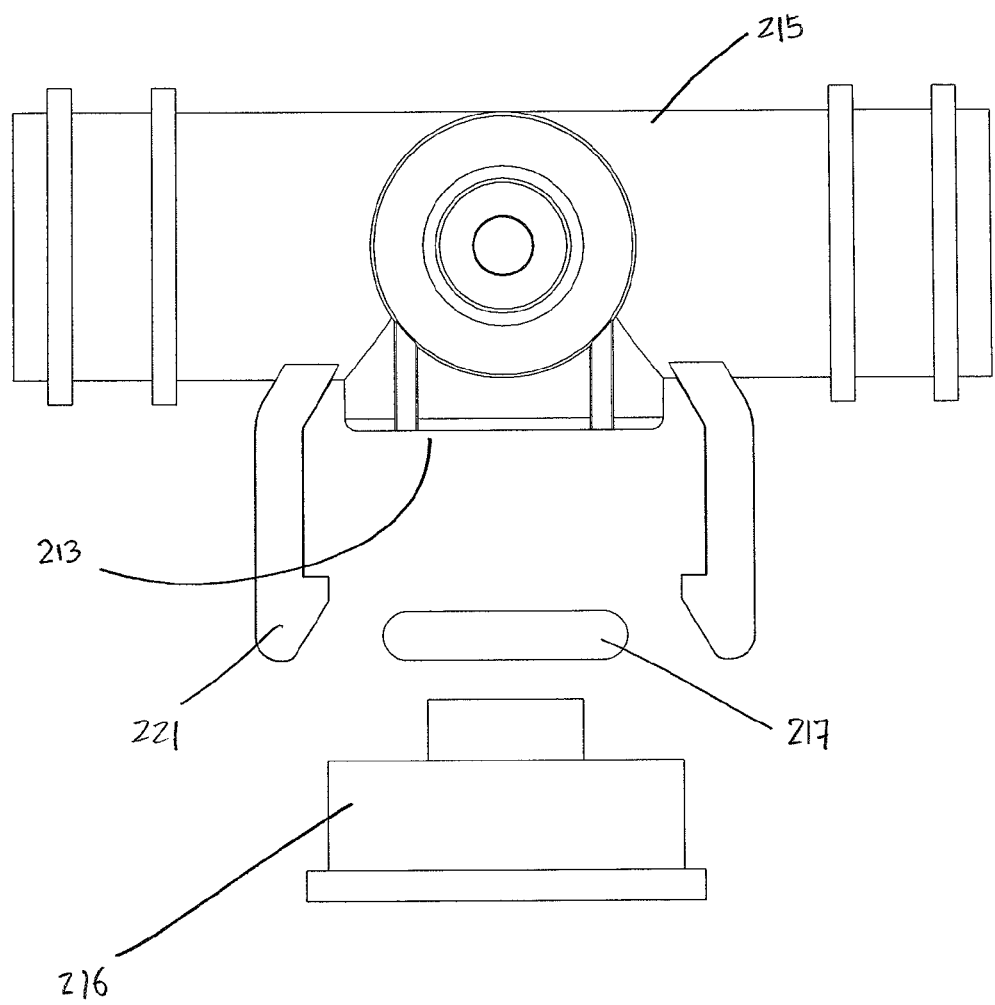

The PL cartridge (200) may also comprise at least one sensor that is in direct contact with the fluid in tubing assembly (214), for example, a pressure sensor (216). As shown in FIGS. 2G and 2H, pressure sensor (216) contacts the fluid sample via an aperture (213) of a T-shape tubing connector (215). An O-ring (217) is used to secure the junction between tubing connector (215) and pressure sensor (216) to prevent fluid leakage. Latches (221) may be used to connect or couple the T-shape tubing connector (215), O-ring (217) and pressure sensor (216) together, though other methods of secure attachment may be used. Other methods of providing fluid access to a pressure sensor may be used, such as bonding the tubing directly to the pressure sensor, or using a pressure sensor that may be placed in-line with the tubing. The pressure sensor (216) in FIG. 2G also has an electrical interface (219) that allows the control system (185) to read an electrical measurement from the pressure sensor. The electrical measurement is then correlated to a known pressure value, by means of the monitor (167), to determine a pressure measurement from the PL cartridge. Any interface, mechanical or electrical, may be used to send a signal that indicates system pressure to the control system. In other variations of the PL cartridge, other types of sensors may also utilize direct contact with the fluid in the tubing assembly, for example, electrochemical, pH, and temperature sensors.

Dispense/Selector Valve

The connectivity between the components of the PL cartridge may be regulated by at least one multiplexing valve. As previously described, the multiplexing valve may be a combination (111) of the fluid selector valve (181) and dispense valve (173) shown in FIG. 1. A multiplexing valve may be adjusted to different configurations to allow the application of positive or negative pressure from a pump to distribute fluid to various regions of the tubing assembly. In some variations, there may be a plurality of multiplexing valves. One example of a multiplexing valve (206) is illustrated in FIGS. 2I-2M.

Figure 2I:
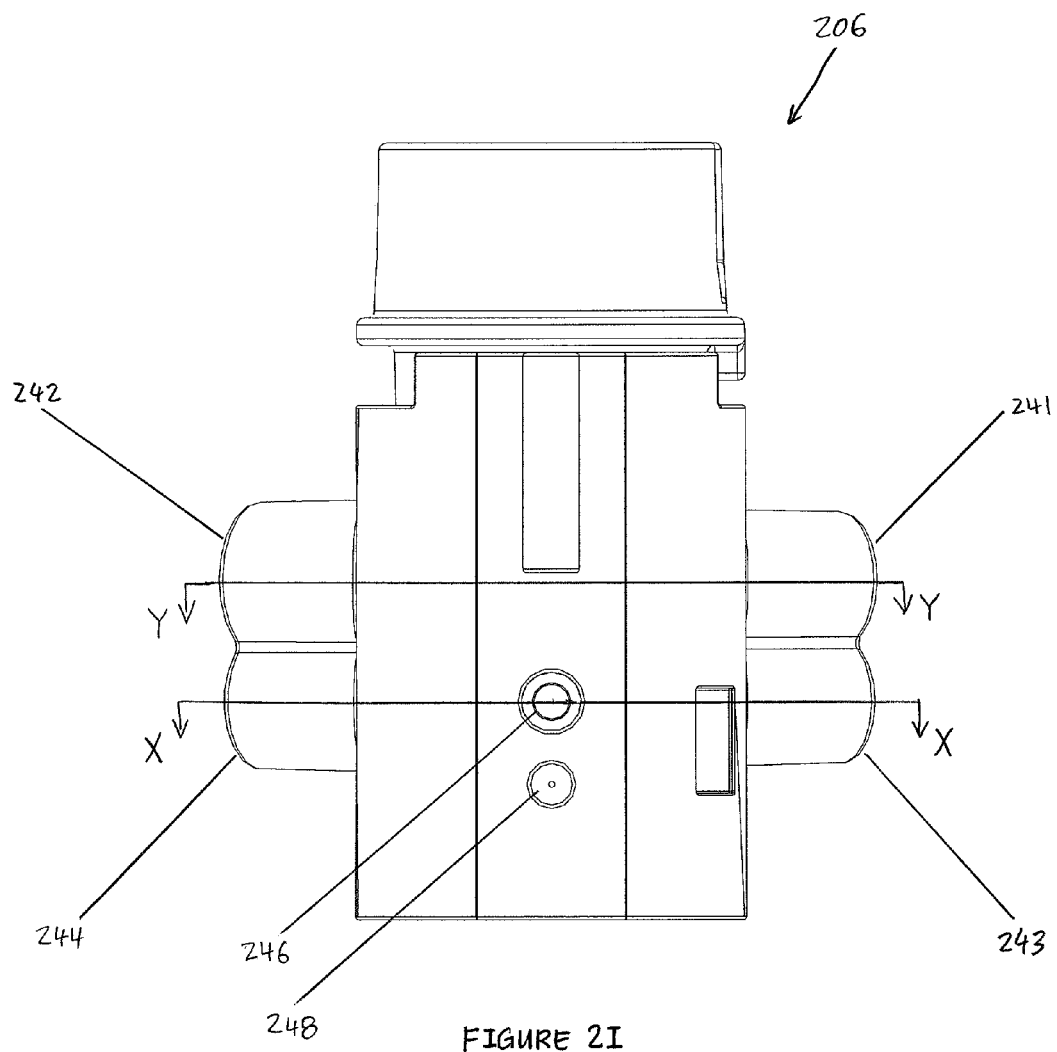
FIGS. 2I-2M depict one embodiment of a multiplexing valve used in the PL cartridge.
Figure 2J:
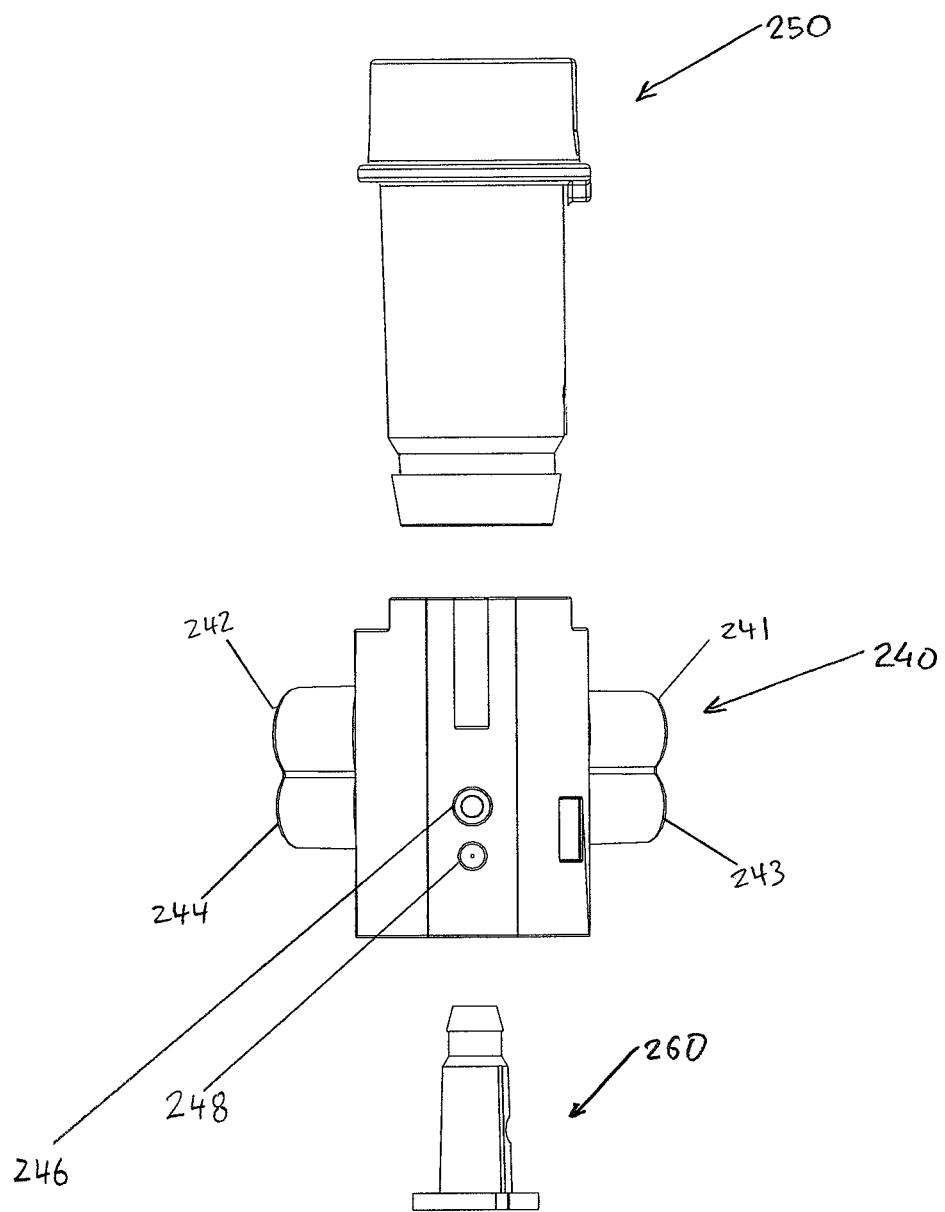
Figure 2K:
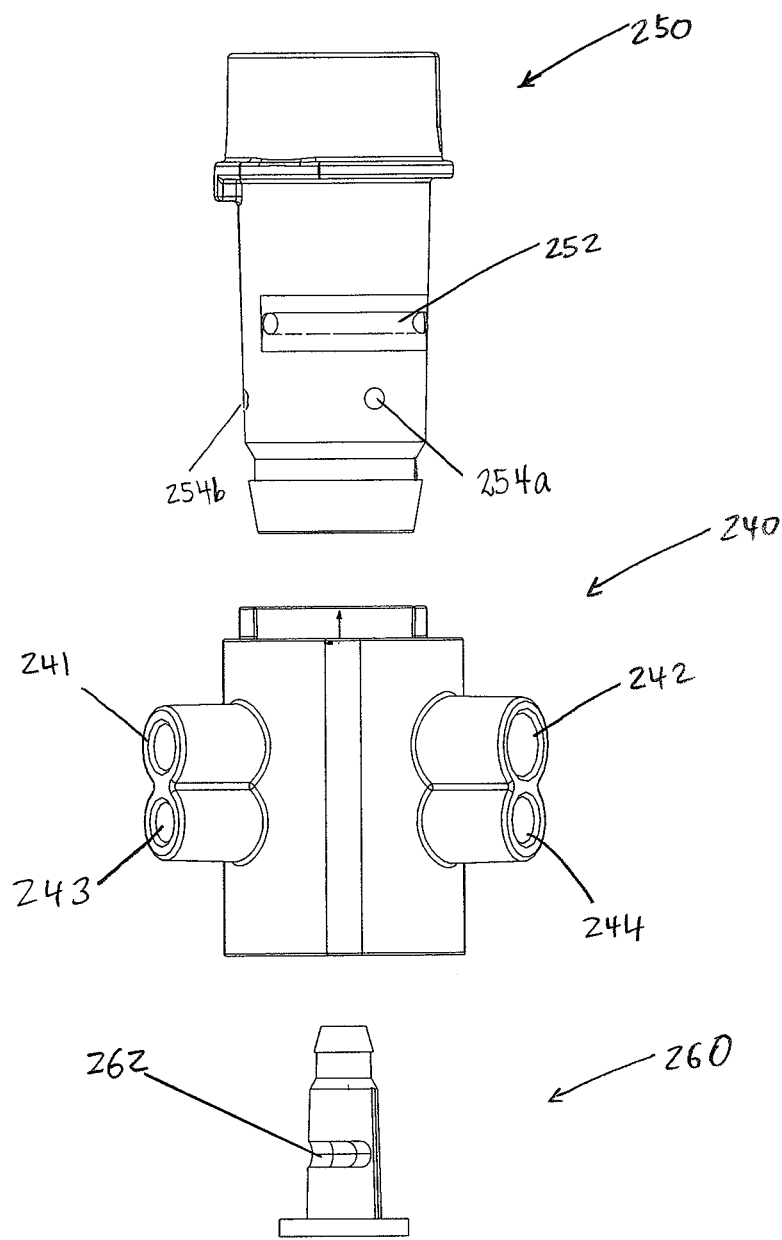

Some variations of a multiplexing valve are formed from an assembly of components. For example, multiplexing valve (206) in FIG. 2J comprises a valve body (240), valve core (250), and valve plug (260). The valve body (240) has plurality of ports that may interface with tubing, for example, inlet ports (241), (242), (243), and (244), a dispense nozzle (246). Some variations may have an alignment protrusion (248) to precisely position the valve body with respect to other components of the fluid monitoring system. Valve body (240) in FIGS. 2I and 2J is tubular, and contains the valve core (250) within its lumen. The valve core (250) is tubular, and contains a valve plug (260) within its lumen. In some variations of a multiplexing valve assembly, the valve plug (260) is not rotatable within the lumen of the valve core (250), but the valve core (250) is rotatable within the lumen of the valve body (240). The rotation of the valve core (250) within the valve body determines the connectivity between the inlets (241), (242), (243), (244), and dispense nozzle (246).

In certain variations, grooves or conduits on the valve core (250) and/or valve plug (260) form conduits that connected the inlets on the valve body. For example, in FIG. 2K, groove (252) on the valve core forms the conduit between inlets (241) and (242). Bores (254a) and (254b) of valve core (250) are aligned in a fixed position with groove (262) on the valve plug (260) and form a conduit between inlets (243) and (244). The orientation of groove (252) is offset with respect to the conduit formed by bores (254a), (254b), and groove (262) so that only one fluid connection is made at a time (e.g. either inlets (241) and (242) are connected, or inlets (243) and (244) are connected). However, in other variations of a valve assembly, the orientation of the plurality of conduits with respect to each other may vary such that one or more connections may be made at a time depending on the particular embodiment of fluid transfer system.

Figure 2L:
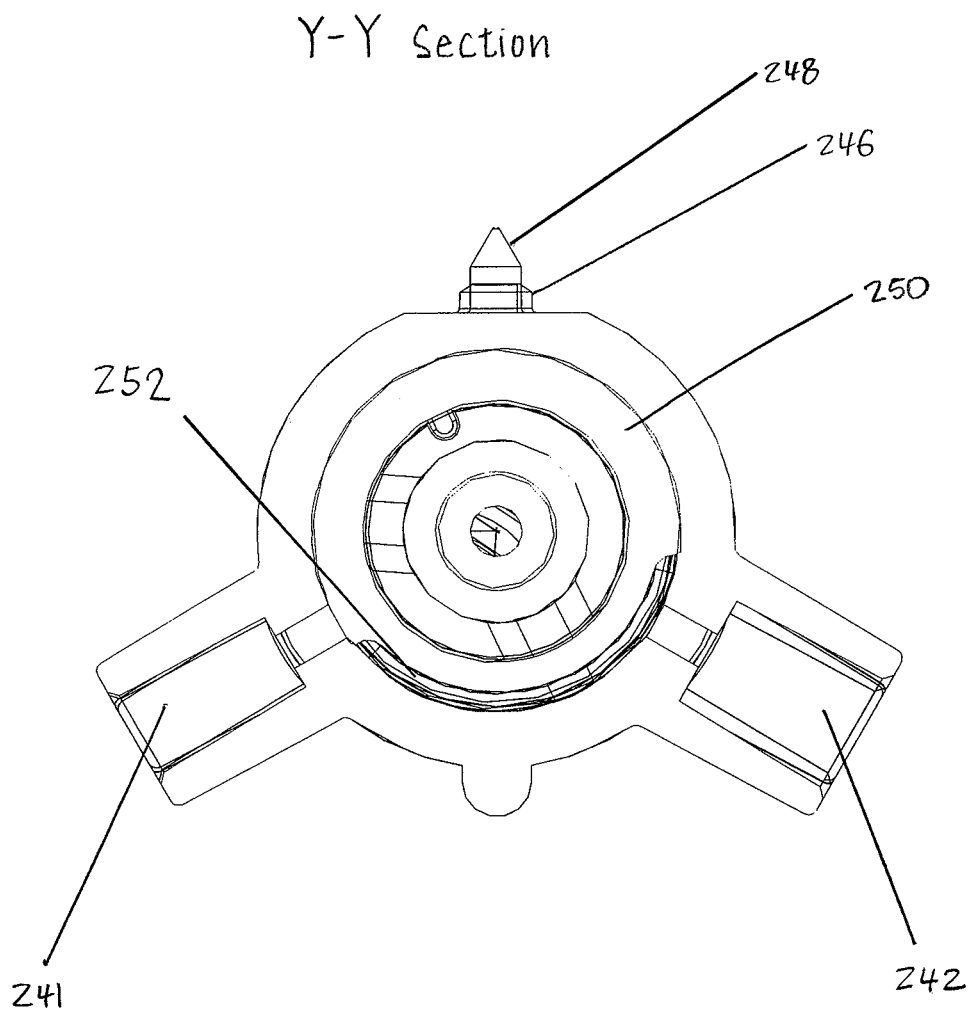

The connectivity between inlets (241) and (242) may be adjusted by rotating the valve core (250), as shown in the Y-Y cross-section of the valve assembly (250) in FIG. 2L. Inlets (241) and (242) are connected when groove (252) on valve core (250) is positioned to contact both inlets, such that the groove space is continuous with the inlets. When the groove (252) is in a position where only one or none of the inlets are contacted, then the inlets are not connected. In this variation, inlet (241) is connected to the syringe pump (211), and inlet (242) is connected to the KVO and flush solution (169), as shown in FIG. 2E. When inlets (241) and (242) are connected via groove (252), the syringe pump is connected to the KVO and flush solution reservoir. In other variations of the PL cartridge, the inlets may be connected to fluidic components as appropriate.

Figure 2M:
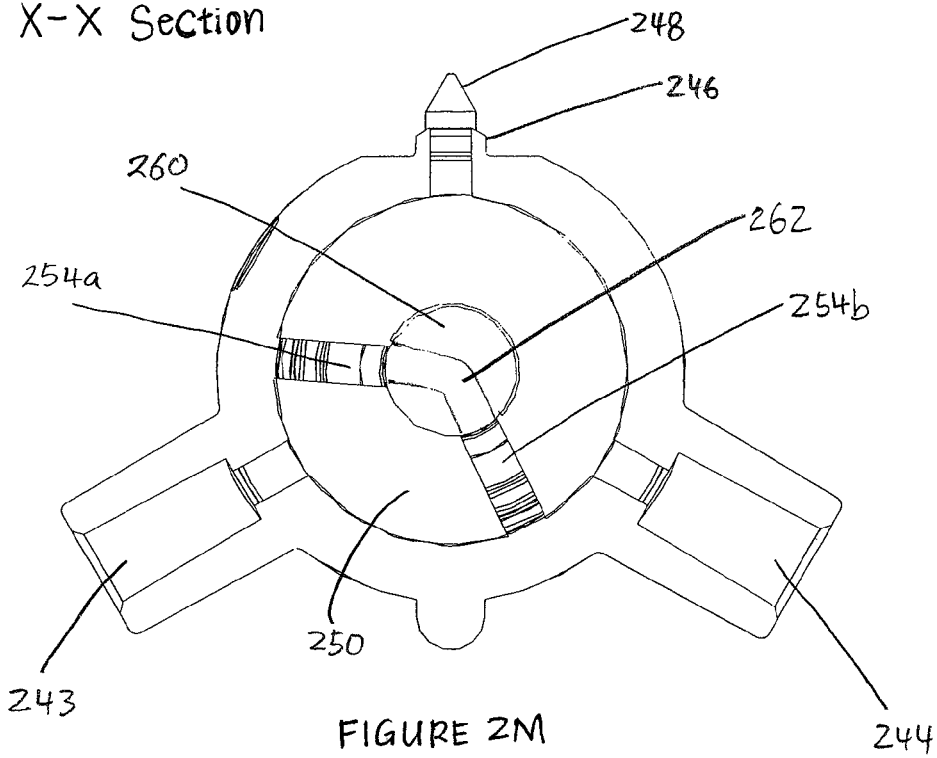
Figures 1, 2M:
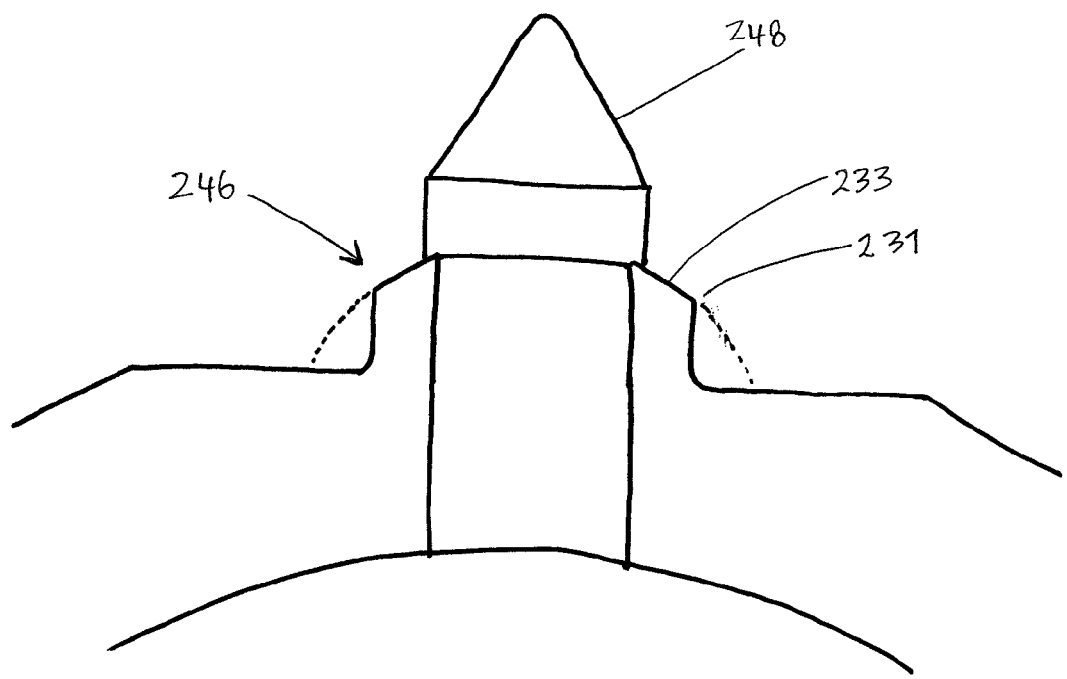

The connectivity between inlets (243), (244), and dispense nozzle (246) may be adjusted by rotating the valve core (250), as shown in the X-X cross-section in FIG. 2M. There are three connection states for this multiplexing function: inlet (243) and inlet (244) are connected, or inlet (243) and dispense nozzle (246) are connected, or none of them are connected. Note that in this variation of the multiplexing valve (206), during operation, the dispense nozzle (246) may not be connected to inlet (244), however, in other variations, this connection state may be used. The connection state is adjusted by rotating the valve core (250) so that the bores (254a) and (254b) (which are aligned with groove (262) in the valve plug) contact the desired inlets. In this variation, inlet (243) is connected to fluid reservoir (222) and inlet (244) is connected to the fluid access device (171), and the dispense nozzle (246) transfers fluid to the disk assembly. In alternate variations, other fluidic components may be connected to the inlets.

The tip of a dispense nozzle may be any suitable geometry that is configured to limit fluid sample adhesion to the dispense nozzle surface. The tip of the nozzle may be configured to reduce wetting of the outside of the nozzle and/or to maintain a sterile fluid path with the patient or avoid contamination of one or more components of the system. FIG. 2M-1 is an enlarged view of the dispense nozzle (246) shown in FIG. 2M. In this variation, the tip (233) of the nozzle (246) is hemispheric, intersecting with a straight edge to form an abrupt sharp edge (231). The sharp edge (231) may break the fluid tension relative to the hemispheric surface, which may provide a controlled delivery of fluid, and reduce loss of fluid or sterility by wetting out. Optionally, the dispense valve and/or nozzle may be coated with an anti-adhesion agent, e.g. an anti-coagulant agent, to ensure effective throughput of the fluid sample.

Figure 2N:
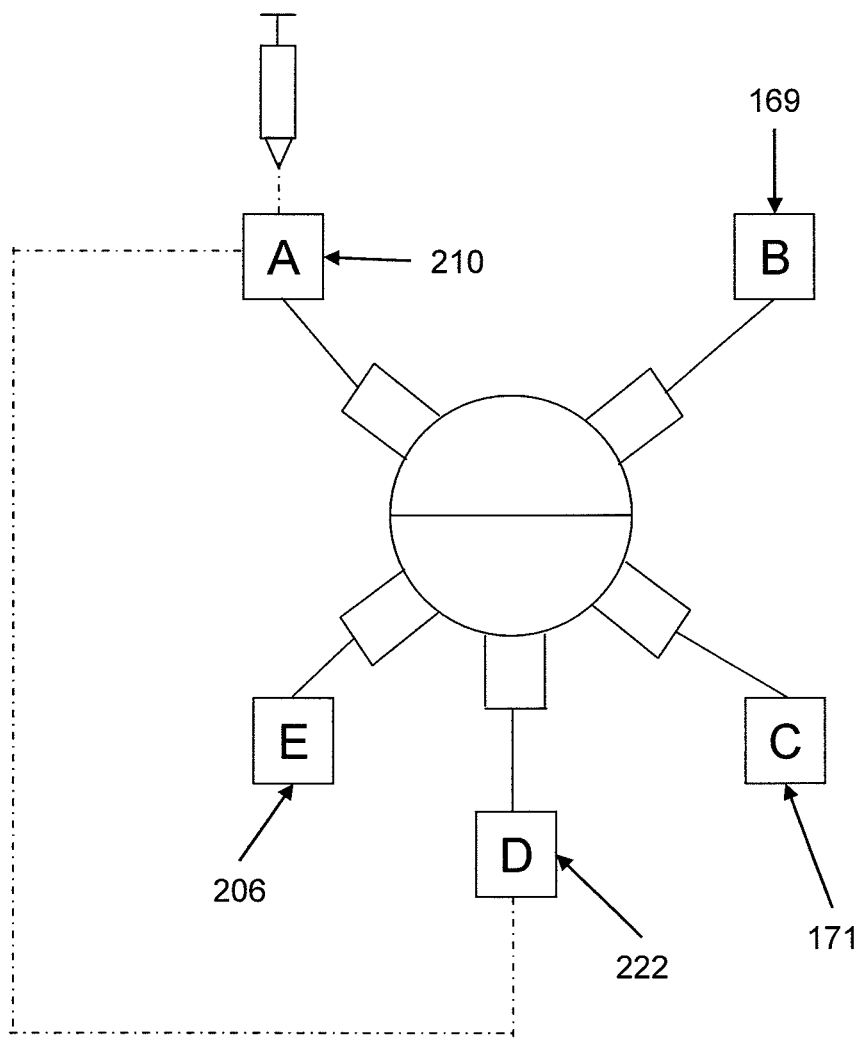
Figure 20:
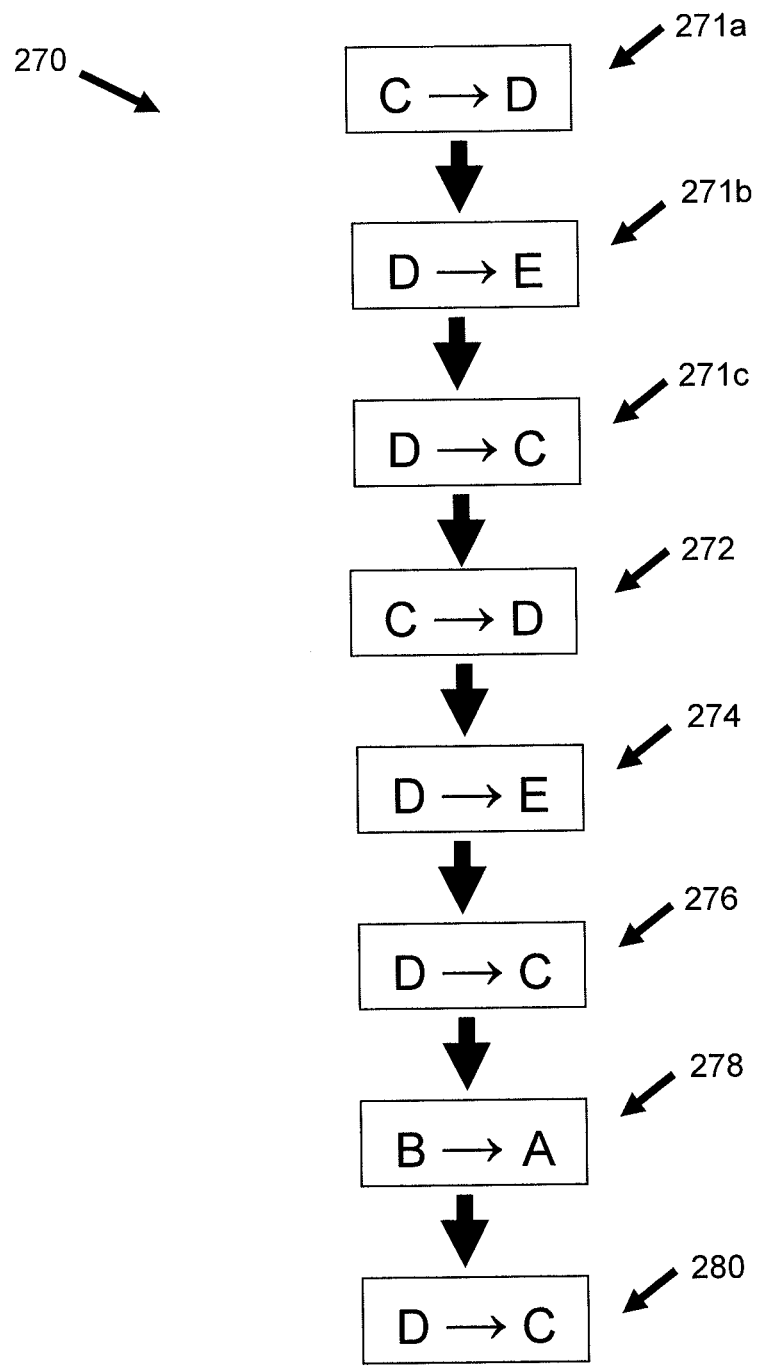

In this variation of the PL cartridge and several of its components shown in FIGS. 2E-2M, the multiplexing valve (206) regulates the connection between the syringe pump (210), KVO and flush solution (169), fluid access device (171), fluid reservoir (222), and dispense nozzle (246), as schematically represented in FIG. 2N. FIG. 2O illustrates an example of a series of connections (270) that may be made to obtain a blood sample from a patient via fluid access device (171) for glucose testing. In step (271a), the system is primed by drawing KVO solution (169) into the syringe (210). Then at step (271b), the fluid is pumped from the syringe (210) through the reservoir (222) to the patient access interface of the tubing. These steps (271a) and (271b) be may be repeated until the system is primed. At step (271c), the KVO solution is drawn into the syringe. In step (272), the fluid access device (171) and syringe are connected through reservoir (222), and a blood sample is drawn from the patient towards and some times into the reservoir (222). In this connection configuration, the monitoring system may poll the blood detector to determine if the fluid in the tubing assembly (214) is undiluted blood. If not, then the system may draw more blood from the patient until the blood detector indicates that the blood sample in the fluid circuit is an undiluted sample. If so, then the monitoring system may proceed to step (274). At step (274), the syringe (210) is connected to the dispense valve through the reservoir (222), and the blood sample is dispensed for testing by pumping KVO solution towards the reservoir (222) to move the blood sample out of the dispense nozzle. In step (276), the syringe (210) is coupled to the fluid access device (171) through the reservoir (222) and any excess blood and solution mixed with blood that may be in the reservoir is returned to the patient (or alternatively or in part, moved to a waste port through a valve in the tubing path (not shown)). At step (278), more saline fluid is pulled into the syringe. At step (280), the fluid is pushed from the syringe (210) through the reservoir (222) to the fluid access device at a selected KVO rate until blood is to be drawn again. When blood is to be drawn again, the system may return to step (272). Other connection and pump sequences may also be used to perform analogous tasks.

Some variations of the multiplexing valve may be rotated to a load configuration after it is manufactured, but before it is used in a fluid monitoring system for the first time. The load configuration is a valve configuration that is not used (and not rotated through) in normal operation of the fluid monitoring system. During the manufacturing process, the multiplexing valve may be imposed into this load configuration using hard stops molded into the valve components. In some variations of a fluid monitoring system, the PL cartridge may be loaded only if the multiplexing valve is in the load configuration. In the absence of a PL cartridge, the fluid monitoring system will transition to a load state, which is a pre-programmed and known configuration that will only interlock with a PL cartridge where the multiplexing valve is also in a load configuration. If the multiplexing valve of the PL cartridge is not a load configuration, then the cartridge cannot be installed in the system. Such a mechanical interlock between the multiplexing valve and the fluid monitoring system in the load state may act to prevent inappropriate installation of the PL cartridge. For example, this feature may prevent the reuse of a PL cartridge, since the multiplexing valve of a used PL cartridge is not in a load configuration. In some variations, the multiplexing valve may contain a "lock-out" feature which prevents the valve from inappropriately being rotated back to the load configuration after it has been removed from the fluid monitoring device.

Fluid Channel Plug

Some variations of a PL cartridge may also comprise a mechanism that ensures that the fluid sample transferred from the dispense nozzle to the input port of the disk assembly proceeds towards the test substrate in the disk assembly, and does not flow back through the fluid channel in the transfer disk. One variation of such a mechanism is a fluid channel plug (224), shown in FIGS. 2A-2F, which is sized and shaped to obstruct the input port of the transfer disk. The fluid channel plug (224) may be made of any fluid impermeable material, and may be actuated in any suitable direction. Other mechanisms may also be used to obstruct the input port of the disk assembly. For example, the input port may be sealed off with an impermeable membrane, pinched shut with a clip, blocked with a rigid cover, or occluded with an inflatable member. Obstruction of the input port may prevent the spread of any contaminants between the disk assembly and PL cartridge, and may acts to urge the blood sample towards the test substrate.

Disk Assembly

Figure 3:
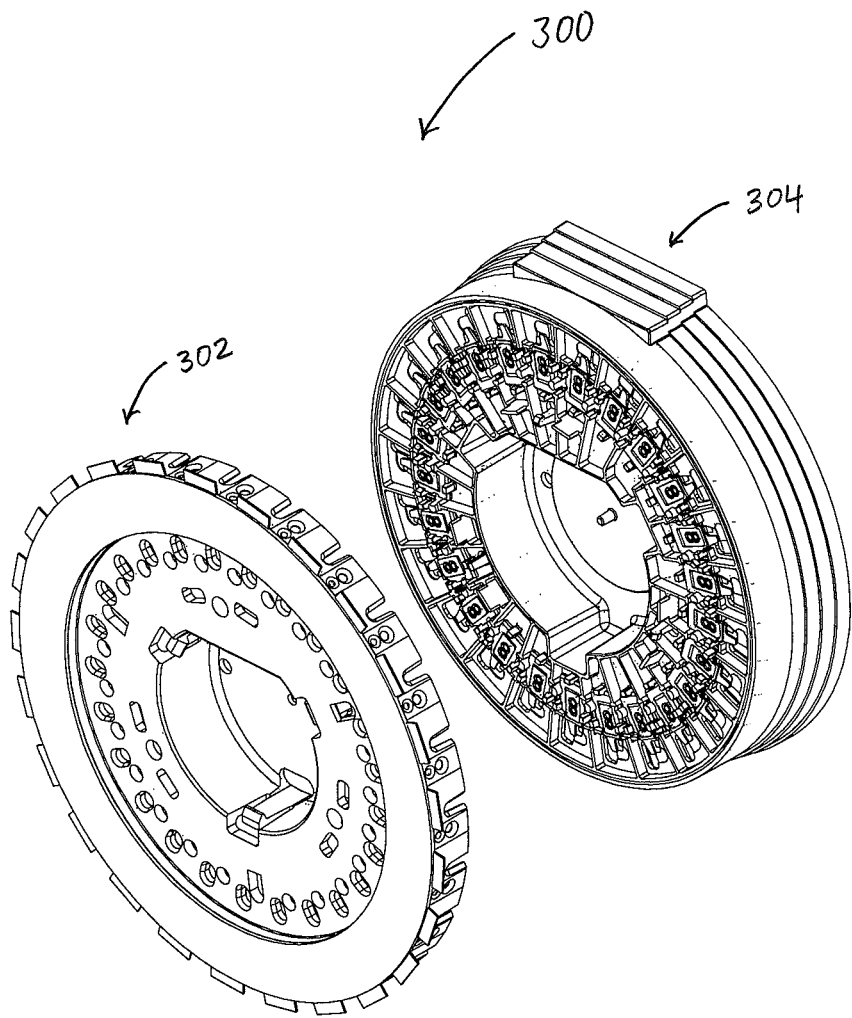
FIG. 3 depicts one embodiment of a multi-component disk assembly.

As shown in FIG. 1, some variations of the automated fluid monitoring system may comprise a transfer and sensor element, such as disk assembly (188) that receives the fluid sample from the PL cartridge and directs the fluid to sensors (161) which may be provided in the disk assembly (188). Disk assembly (188) may contain any number of functional modules that perform some or all of the tasks used to receive the sample for testing. For example, the disk assembly may comprise a single cartridge or housing that receives the sample from the PL cartridge and channels it to the test substrate, which may have an interface suitable for the control system to read out the test result. In some variations, the disk assembly may comprise two or more functional elements, such as individual cassettes, drums, cartridges, or disks. Multiple functional elements may be provided to house and separate components undergoing sterilization or those with other different handling requirements, for example. Thus, individual components that require sterilization may be sterilized, without sterilizing the entire disk assembly. For example, a portion of the disk assembly that may be momentarily in fluid contact with a patient's circulatory system may be sterilized, but other components of the disk assembly that do not come into fluid contact with a patient may or may not be sterilized. In some examples, limiting or avoiding sterilization of the sensors (or other components) may prolong the shelf-life or maintain the accuracy of a sensor or a test substrate. A multi-disk assembly may maintain test substrate and/or sensor sensitivity while reducing the risk of contamination to the patient. An example of such a disk assembly is illustrated in FIG. 3. In certain variations, as depicted in FIG. 3, the disk assembly (300) may comprise at least two components, such as a fluid transfer disk (302) and a test sensor disk (304). The transfer disk (302) and the sensor disk (304) are configured to work in concert to receive a sample for testing. The transfer disk (302) receives the fluid sample from the PL cartridge, and transfers it to the sensor disk (304) for testing.

Transfer Disk

Figure 4A:
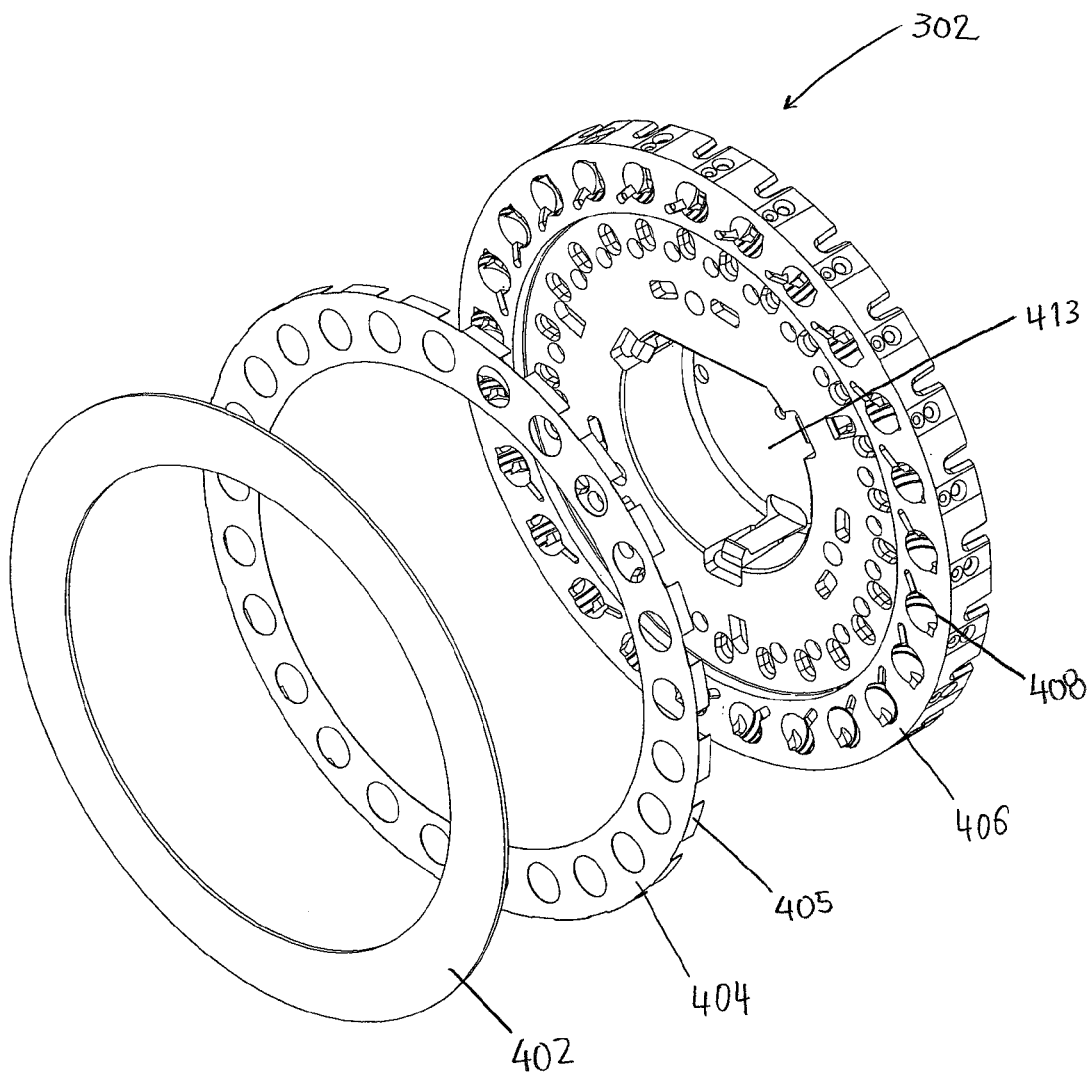
FIGS. 4A-4B depict one embodiment of the transfer disk that may be used in a multi-component disk assembly.
Figure 4B:
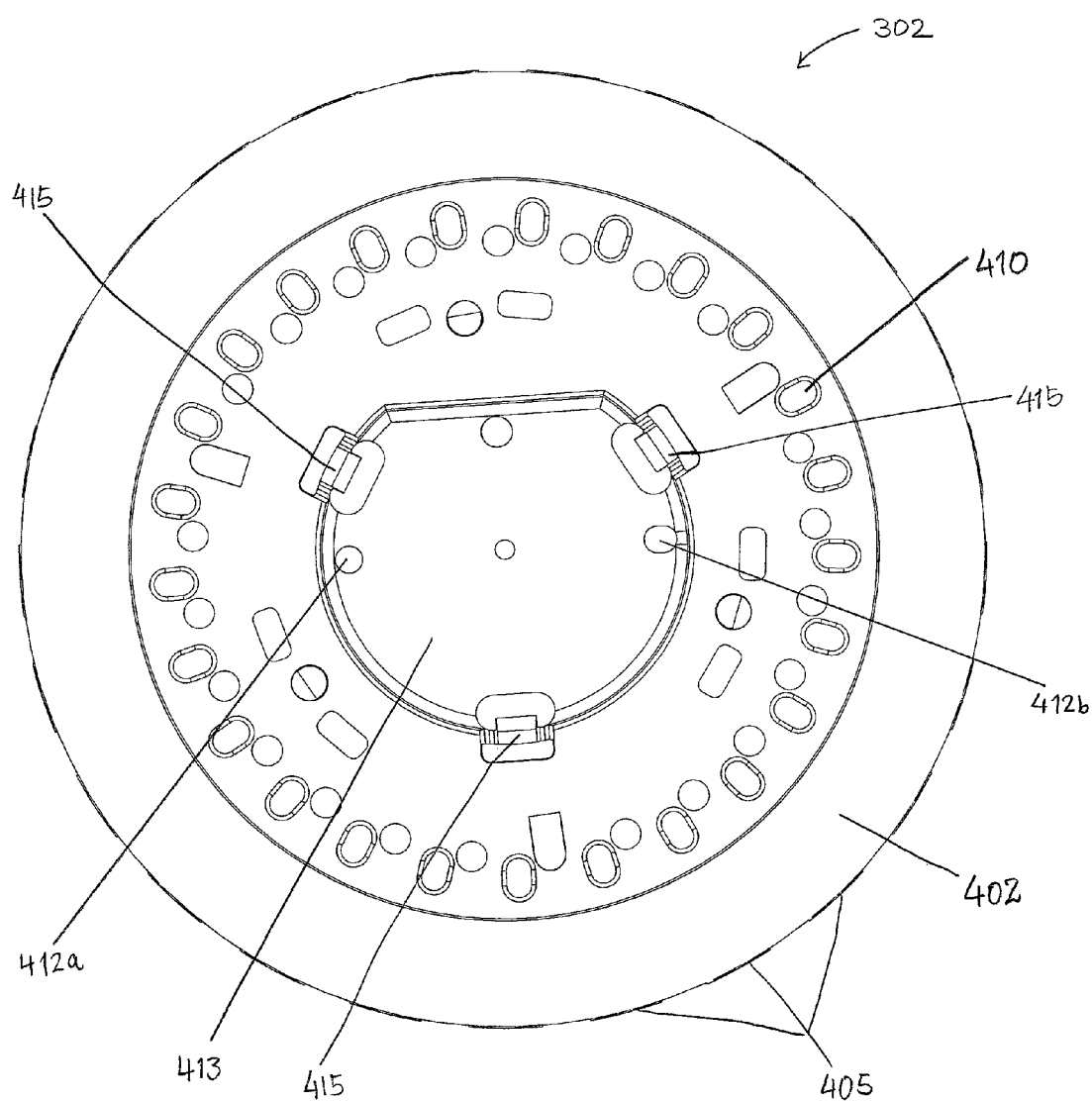

As shown in FIG. 1, the transfer disk (196) may be a separate component of the disk assembly (188). A fluid transfer component of the disk assembly, such as the transfer disk (302) shown in FIGS. 4A and 4B, is configured to receive the fluid sample from the PL cartridge, and may be particularly configured to transfer fluid from a sterile source to a non sterile environment without contaminating the sterile source. In other embodiments of the disk assembly, the transfer component may also be a cassette or cartridge. The transfer disk may comprise a pump and pump actuator that may be a deformable member. As depicted in FIG. 4A, the transfer disk (302) comprises a deformable membrane (402), a wipe assembly (404), and a transfer disk structure (406). These three components may be bonded together with an adhesive, where the wipes (405) may be bonded to the outer perimeter of the transfer disk structure (406). Alternatively, the three components may be bonded together by means such as welding or vulcanizing one or more materials to the other materials. The deformable membrane (402) is overlaid in a way to provide a fluid-tight seal to the transfer reservoirs (408), and may be made of any fluid impermeable, compliant material, such as silicone, latex, urethane, and/or thinly hammered metal alloy or polymer. In some variations, the transfer reservoirs (408) are arranged around the outer circumference of the transfer disk structure (406), and the membrane is sized and shaped to cover the open side of the transfer reservoirs (408), which may form individual fluid displacement elements operatively coupled to each reservoir (408). The transfer disk structure (406) is made of molded acrylic, but may be made of any material with similar structural and optical properties. Wipes (405) may be evenly spaced around the outer edge of transfer disk structure (406), and arranged to contact the dispense nozzle (246) during use. The transfer disk structure (406) may comprise an interface that allows the control system to read out from the test sensors of the sensor disk, for example, apertures (410) may be sized and positioned according to the size and positions of the test sensors on the sensor disk, which may be adjacent to the transfer disk. Apertures (412a-b), indentation (413), and latches (415) are structures that may be used to align the transfer disk to the other components of the fluid monitoring system, and to secure and lock the transfer disk in place for use. These features will be described in detail below.

Figure 4C:
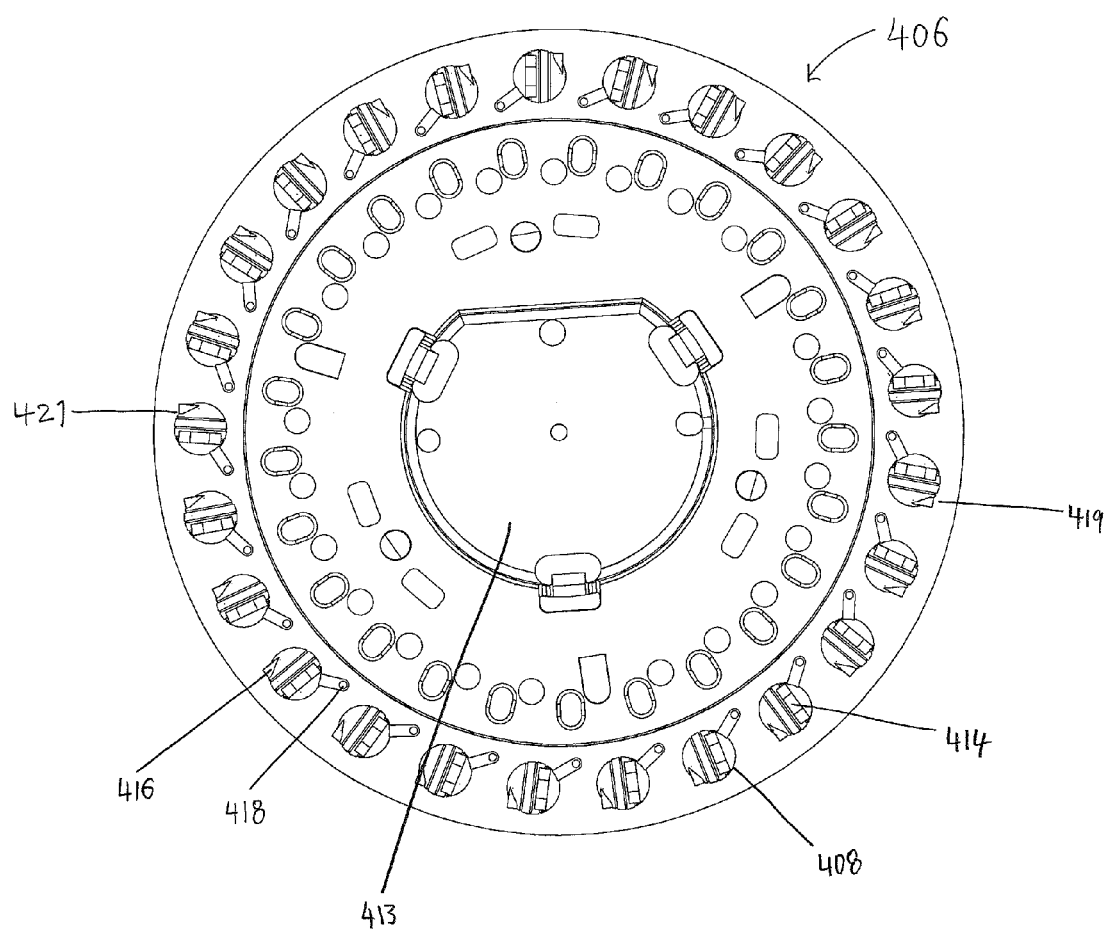
FIGS. 4C-4E depict one embodiment of the transfer disk structure.
Figure 4D:
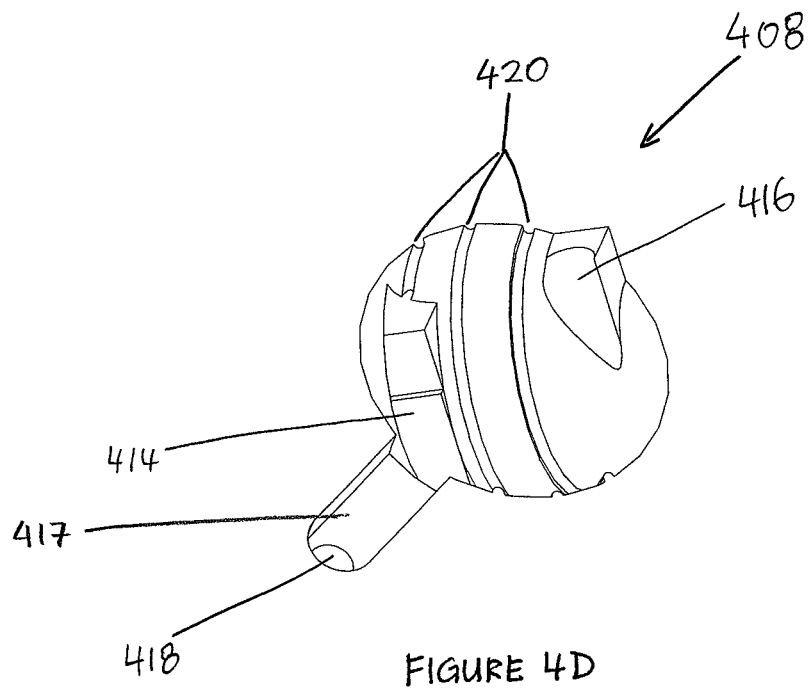
Figure 4E:
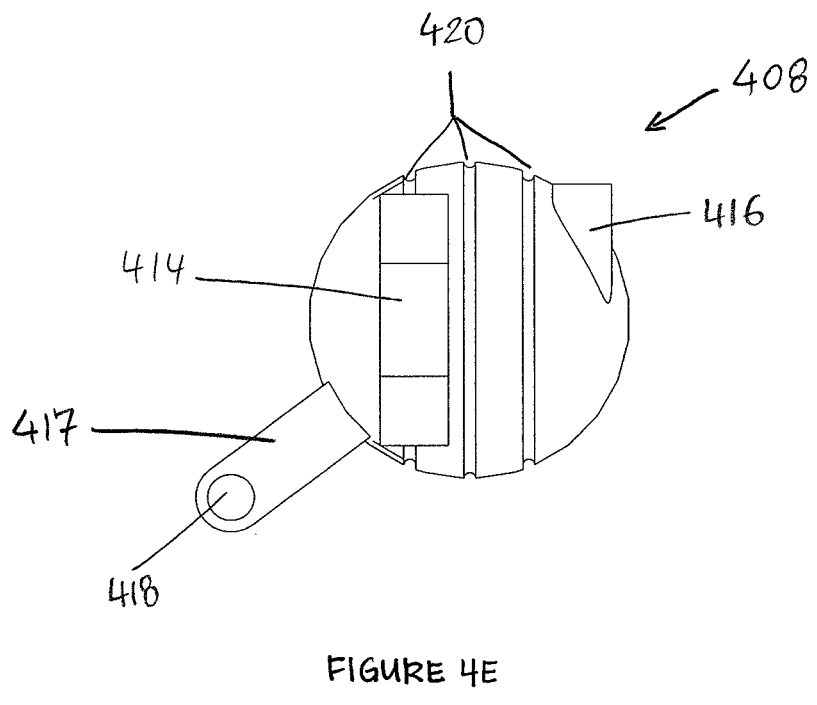

As shown in FIG. 1, transfer disk (196) may comprise a plurality of fluid sample cavities (189) that separate and transport a fluid sample. One variation of a transfer disk comprises a transfer disk structure (406) as shown in FIG. 4C. Transfer disk structure (406) may comprise a plurality of transfer reservoirs (408), such as the 25 transfer reservoirs, but in other variations, any other number of transfer reservoirs may be provided, including but not limited to at least (or no more than) about 5, about 10, about 15, about 20, or about 30 transfer reservoirs. Reservoirs may be disposed in a circular pattern on the disk or may be disposed in 2 or more coaxial circular patterns so that multiple reservoirs exist at 2 or more radial positions along each radius line, thus increasing the capacity of reservoirs on the disk by two fold or three fold. Each transfer reservoir (408) may have an inlet (416), which receives the fluid sample from the PL cartridge dispense nozzle (246), and an outlet (418) which allows the sample to be transferred to the sensor disk for testing, as shown in FIGS. 4D and 4E. Inlet (416) and outlet (418) may be openings or channels. In some variations, the transfer reservoir may also comprise an outlet neck (417), which may be a shallow channel from the transfer reservoir to the outlet. Optionally, transfer reservoir (408) may comprise a plurality of ridges (420) that discourages fluid adhesion to the surface of the transfer reservoir, thus facilitating the movement of the fluid from inlet (416) to outlet (418). The ridges (420) may be arranged in series (in any orientation) along the fluid flow from the inlet (416) to the outlet (418). For example, the ridges (420) may be oriented parallel to the fluid flow into the reservoir. The fluid flow from the inlet to the outlet may vary depending on the orientation of the transfer disk. For example, in some variations of a fluid monitoring device, the transfer disk may be mounted vertically, i.e. on its side. In this variation, if the fluid sample is dispensed to a transfer reservoir at location (419) shown in FIG. 4C, the fluid sample entering the inlet would need to be urged upward towards the outlet. Alternatively, if the fluid sample is dispensed to a transfer reservoir at location (421), the fluid sample entering the inlet would flow downward towards the outlet due to gravity. In some variations, the transfer disk may be mounted horizontally. In some variations of a horizontally mounted disk, the reservoir and fluid channels would be positioned so that fluid entering the inlet would need to be urged across the transfer reservoir in order to exit through the outlet.

Figure 4F:
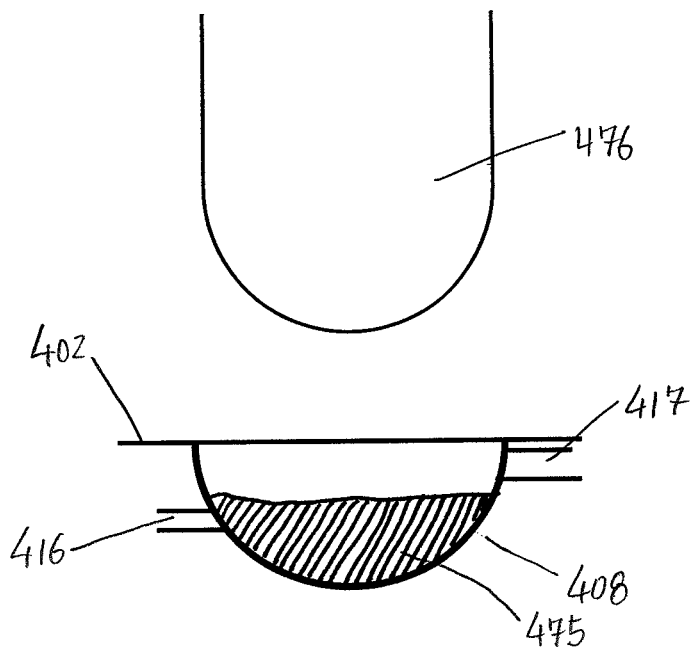
FIGS. 4F-4G depict a pump mechanism that may be used to urge a fluid sample in a transfer reservoir.
Figure 4G:
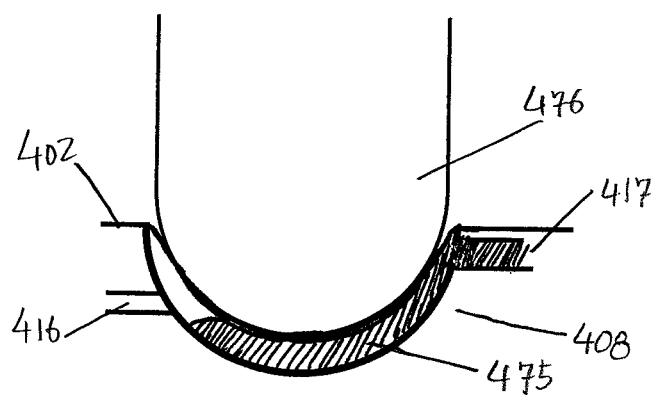

The fluid sample may be transferred from the inlet (416) to the outlet (418) in various ways. In some variations, the transfer may not take place until after the dispensing of the fluid ceases entirely, i.e. there is no fluid that connects the PL cartridge and/or dispense nozzle to the disk assembly. A number of variations may be used to help move a sample from inlet (416) into the transfer reservoir. For example, the transfer reservoir (408) (or the portion of the disk assembly) that contains the fluid sample may be tilted, allowing the sample is directed to the outlet (418) by gravity feed. Alternatively, the transfer reservoir (408) may be made of a material that facilitates capillary action. The direction of the capillary action may be configured by machining different micro patterns on the surface of the transfer reservoir that allows fluid migration in one direction but not in the opposite direction. In some variations, this material may be substantially contacted with the test substrate, allowing the fluid to be conveyed by capillary action entirely within the material. Fluid may also be drawn towards the outlet (418) by setting up a pressure gradient across the transfer reservoir (408), such that the outlet (418) is in a region of lower pressure. Pressure gradients may be created through the use of a vacuum bulb, drawing the fluid into the transfer reservoir, and expelling the fluid towards the outlet. For example, it may urge, push, or direct the fluid towards the outlet with a fluid displacing element or fluid directing element. Other methods of directing the fluid sample to the transfer reservoir outlet may utilize deformable or displaceable structures. For example, the transfer reservoirs made be made of a deformable material, such as silicone or a sheet of malleable metal alloy, and tubular shaped, so once the fluid has been dispensed and dissociated from the PL cartridge, the tubular transfer reservoir is pinched shut, and the pinching mechanism gradually moves towards the outlet, essentially "squeezing" the fluid sample to the outlet (418). In other embodiments, the fluid may be urged through the transfer reservoir by a slidable seal or piston, which may act to pressurize the transfer reservoir cavity. In another variation, the volume of the transfer reservoir (408) may be adjusted, e.g. from large to small, to displace the sample fluid towards the outlet neck (417). The volume of a transfer reservoir may be changed by constricting or dilating the transfer reservoir lumen and/or introducing an external element that displaces a sufficient volume in the transfer reservoir that forces the fluid sample to move towards the outlet. One example is shown in FIGS. 4F and 4G. The deformable membrane (402) is sealed across the transfer reservoir (408) which creates a liquid-tight enclosure. Once a desired quantity of fluid is deposited into the transfer reservoir (408), the membrane (402) is deformed with a piston (476). The deformation in the membrane (402) created by the piston (476) acts to displace the fluid into the outlet (418). The initial volume of the transfer reservoir (408) may be of any suitable quantity, for example, between approximately 1.2-10.0 µL, or approximately 1.0-100 µL, or approximately 1.0 µL to more than 100 µL, however, when the membrane (402) is deformed, the volume of the transfer reservoir is reduced from the initial volume. The volume of the transfer reservoir before and during membrane deformation may vary widely. This method of fluid transfer may allow for a greater degree of flow control (as compared to gravity feed or capillary action) and may be done more rapidly (as compared to "squeezing" the fluid in a tubular transfer reservoir). In alternate embodiments, a displaceable seal or piston with a generally fixed configuration may be provided to push the fluid sample out of the transfer reservoir. Furthermore, positioning the outlet neck (417) at a higher plane than the inlet (416) buffers the downstream sensor substrate from fluid overflow, which allows the control system (185) additional time to remedy the overflow condition. The inlet (416) may be occluded, covered, sealed or blocked to prevent the fluid sample contained in the transfer reservoir from flowing backwards when the piston (476) acts on the membrane (402). For instance, the fluid transfer plug (224) shown in FIGS. 2A-2E may be used to block the inlet (416). Other suitable means of occluding the inlet may also be used, for example, the inlet may be constricted by a clip, or sealed off with a thin film material or flap.

The membrane (402) may be shaped such that a deformation in the membrane (402) will displace the fluid sample within the transfer reservoir (408). In some configurations, the membrane (402) may have a plurality of folds and/or creases, which may allow for a greater degree of membrane compression and fluid displacement. For example, the folds may be evenly formed in a pleated configuration, but may also assume any suitable geometry. In other variations, the membrane (402) is stretched over the transfer reservoir (408) with a certain degree of tension, with few if any folds or creases. This configuration may reduce or minimize the surface area of the membrane that contacts the fluid sample, which may increase the quantity of fluid that is transferred to the sensor substrate. Each portion of the membrane is isolated from each other by chemical bonds, mechanical bonds, or a combination thereof, or interference plastic fit parts to ensure that the fluid within each reservoir is maintained within that reservoir without leaking or transferring to other reservoir. These features may act to isolate the sample to one and only one transfer reservoir. This may reduce or eliminate cross contamination between samples.

The fluid input channel to transfer reservoir (408) may be any shape or size that efficiently accepts a fluid sample. A variation of fluid input channel is shown in FIGS. 4I and 4K. The fluid input channel comprises an input aperture (424) that is connected to a bore (423) shown in FIG. 4I. Some variations of a fluid input channel may have a tapered input aperture (424) to better mate with the shape of the dispense nozzle of the PL cartridge, which may funnel fluid into the transfer reservoir (408) more efficiently, however the shape and size of the input aperture (424) may be varied according to the characteristics of the system and/or fluid viscosity. The size and shape of the input aperture (424) may also facilitate the dissociation of the fluid from the dispense nozzle from the fluid in bore (423). Breaking the fluid connection between the dispense nozzle and the fluid input channel may reduce the risk that contamination which may have entered the transfer disk from other sources is then transferred to the patient. Optionally, the surface of the input aperture (424) and bore (423) may be coated to prevent the fluid from adhering to the surface. The coating may be an anti-coagulant agent, surfactant, or charge-neutral coating that may reduce the influence of electrostatic forces on fluid flow.

Figure 4H:
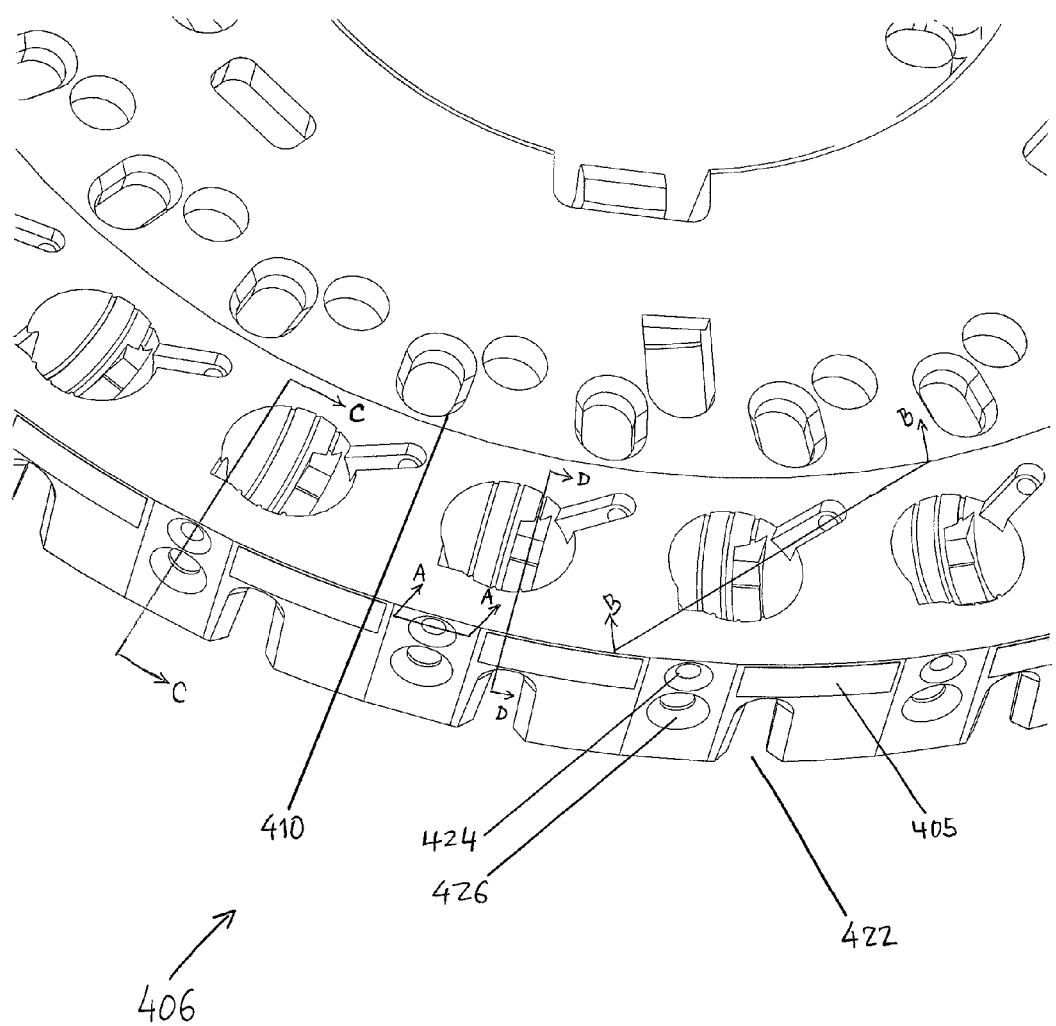
FIGS. 4H-4L depict various aspects and components of the transfer disk structure, including the transfer reservoir, inlets and outlets, and the total internal reflection mirrors and light path for optical sensing of a fluid sample (e.g. blood).
Figure 4I:
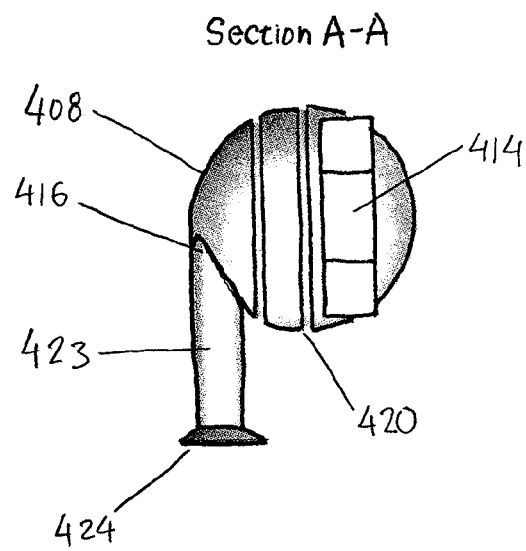
Figure 4J:
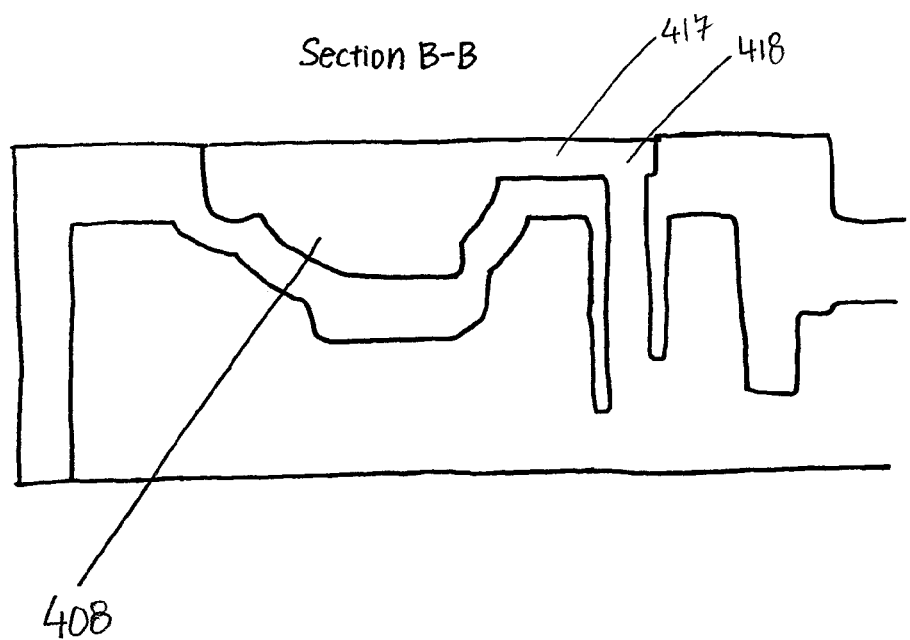
Figure 4K:
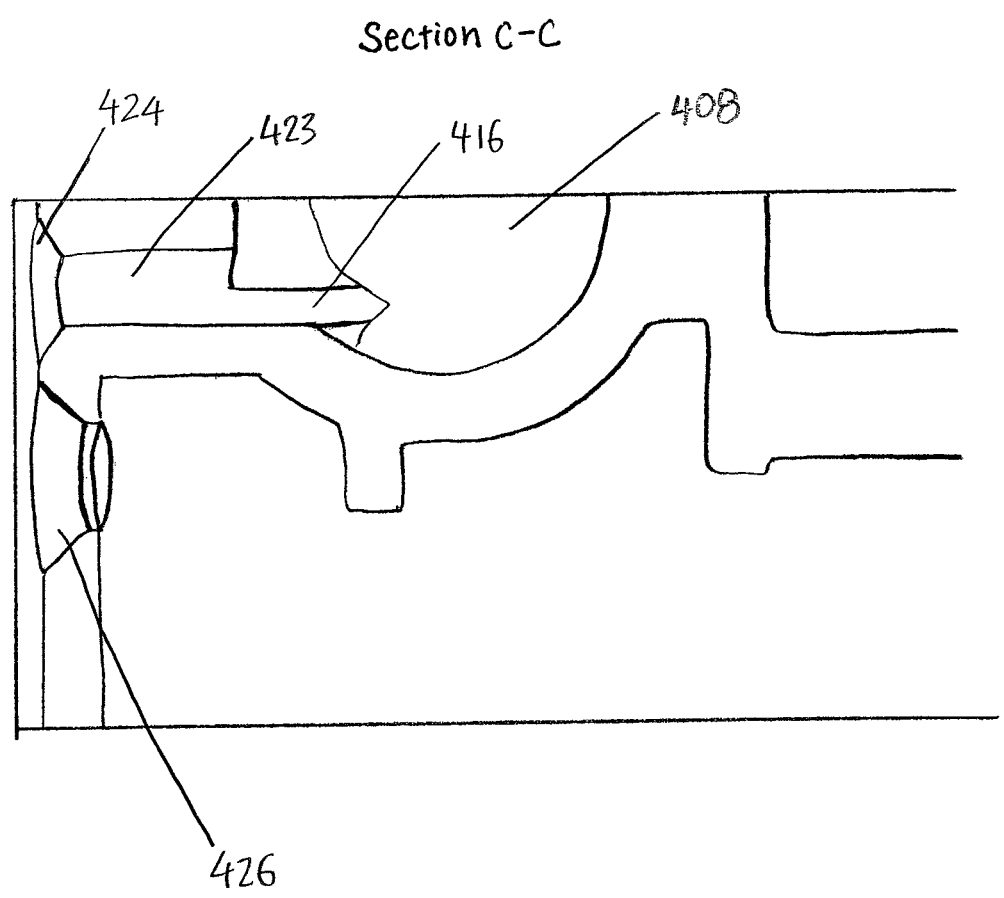

FIG. 4J depicts section B-B taken across the transfer reservoir (408) and outlet neck (417) shown in FIG. 4H. In a horizontal position (such as the orientation shown in FIG. 4J), the outlet neck and outlet of the transfer reservoir (408) may be located at a higher plane than the inlet (416). Such an arrangement may prevent a direct and immediate fluid flow-through from the inlet to the outlet. In a vertical position, where the outlet neck (417) points up and the inlet (416) points down, a fluid sample entering the inlet would be prevented from directly and immediately flowing through to the outlet (418). In these arrangements, the transfer reservoir acts as a buffer intermediate between the inlet and outlet, and may allow for increased control of fluid flow between the transfer disk and sensor disk. Features that allow for precise regulation of the fluid flow may reduce the possibility of a continuous fluid connection from the sensor disk to the transfer disk to the patient. This may safeguard the patient against contamination from any non-sterile components of the disk assembly.

Figure 4L:
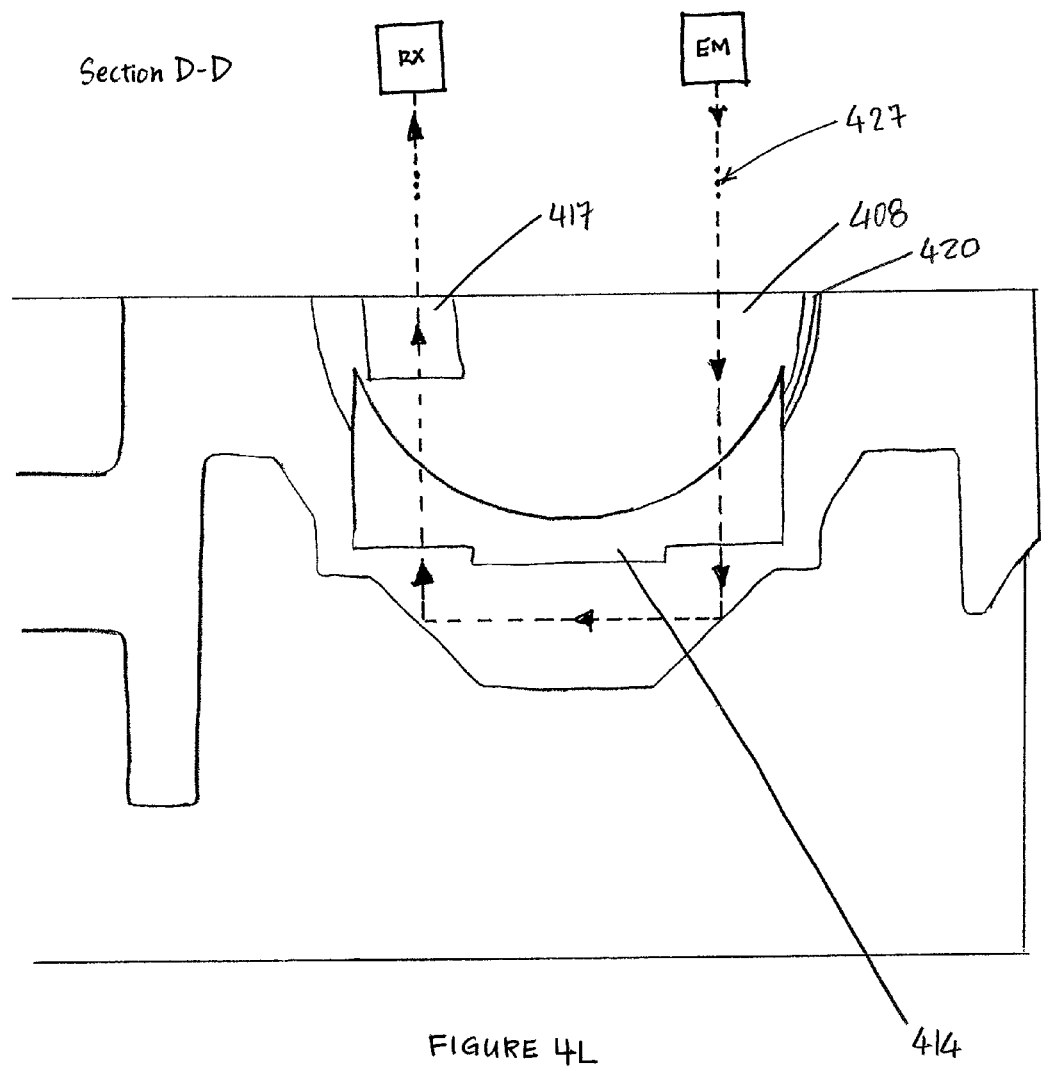

Transfer reservoirs may also comprise a fluid detector to indicate when the transfer reservoir has reached a maximum or minimum fill level. A variety of sensors may be used, such as optically reflective, electrically conductive, or capacitive sensors. Certain variations of transfer reservoirs (408) are formed of molded acrylic, which allows sensors optical access to the contents within the transfer reservoir. For example, as shown in FIGS. 4I and 4L, total internal reflection minors (414) are molded into the transfer disk structure, and may channel the optical characteristics of the transfer reservoir contents to a sensor that detects for the presence or absence of fluids. In some variations, an infrared beam enters into the transfer disk and is reflected back to the transfer reservoir along a light path, for example light path (427), until a fluid (such as blood) interferes with the beam. In this embodiment, as shown in FIG. 4L, the infrared beam emitter and receiver may be located on the fluid monitoring system, directly across from the total internal reflection mirrors in the transfer reservoir, configured to transmit and receive light, e.g. infrared, along light path (427). Some embodiments of an infrared sensor can detect quantities of fluid between about 50 µL to about 80 µL, but sensors with other ranges of fluid sensitivity may also be used. Fluid sensor output may be used as a feedback signal to the control system (185) to regulate various aspects of the fluid monitoring system, such as adjusting the fluid flow and quantity (e.g. to prevent under fill and overfill conditions), and to signal if fluid is unexpectedly in the transfer reservoir.

As shown in FIGS. 4B and 4H, the transfer disk structure (406) may comprise a number of alignment features, such as notches, interlocking structures, apertures, and protrusions. Appropriate alignment of the transfer disk with respect to the other components of the fluid monitoring system may ensure precise fluid transfer from one component to the other. Such alignment features may also be used to provide clearance between the individual components of the disk assembly, and may include locking mechanisms to secure one component to another. For example, apertures (412a) and (412b) shown in FIG. 4B on the transfer disk (302) may be aligned to protrusions on other parts of the fluid monitoring system, so that the monitoring system can precisely dispense the fluid sample, locate the sensor outputs, and correctly index the individual transfer reservoir units on the transfer disk. Indentation (413) may be sized and shaped to mate with other components of the monitoring system to ensure consistent and precise alignment. Latches (415) may be mechanically interlocked with complementary structures, e.g. notches, on the monitoring system, to secure and lock the transfer disk to the overall system. Transfer disk structure (406) may also comprise alignment aperture (426) that mates with the alignment protrusion (248) to ensure precise positioning of the dispense nozzle (246) into input aperture (424). The transfer disk structure (406) may also have an alignment notch (422) to mate with an alignment protrusion on the PL cartridge to precisely position dispense nozzle (246) in contact with wipe (405) in between dispense cycles. The transfer disk (302) may have any number and variety of alignment features to precisely position and secure it to the fluid monitoring system.

The transfer disk (302) may comprise cleaning pads or wipes (405) similar to those shown in FIG. 4H to wick away excess fluid from the dispense nozzle (246) in between dispense cycles. The wipes (405) may be made of any absorbent material, for example, a polyester/cellulose non-woven blend, which has a high affinity for the fluid that is being monitored so that the fluid may be wicked away quickly and evenly. The wipes (405) may be positioned or shaped in any way that optimizes its contact with the dispense nozzle (246). For example, some wipes (405) may comprise protrusions and/or micro structures to increase surface area contact with the dispense nozzle, the protrusions may be shaped to be complementary to the shape of the dispense nozzle. In some variations, the wipe (405) may be positioned on a mechanism that can be actuated to wipe the dispense nozzle, for example, the wipe may be moved laterally across the dispense nozzle, or plunged into and out of the lumen of the nozzle to absorb excess fluid. In other variations, wipes may contact the dispense nozzle without any lateral movement, i.e. the wipe may "blot" the dispense nozzle to wick away excess fluid. Excess fluid may contaminate any sterile components in the PL cartridge or transfer disk, as well as possibly skewing the test results of later fluid samples. In the case where blood is the fluid that is monitored, excess blood on the dispense nozzle (246) may clot and occlude the transfer of latter blood samples for testing, and may contaminate the latter samples which may result in an inaccurate test result.

Sensor Disk

Figure 5A:
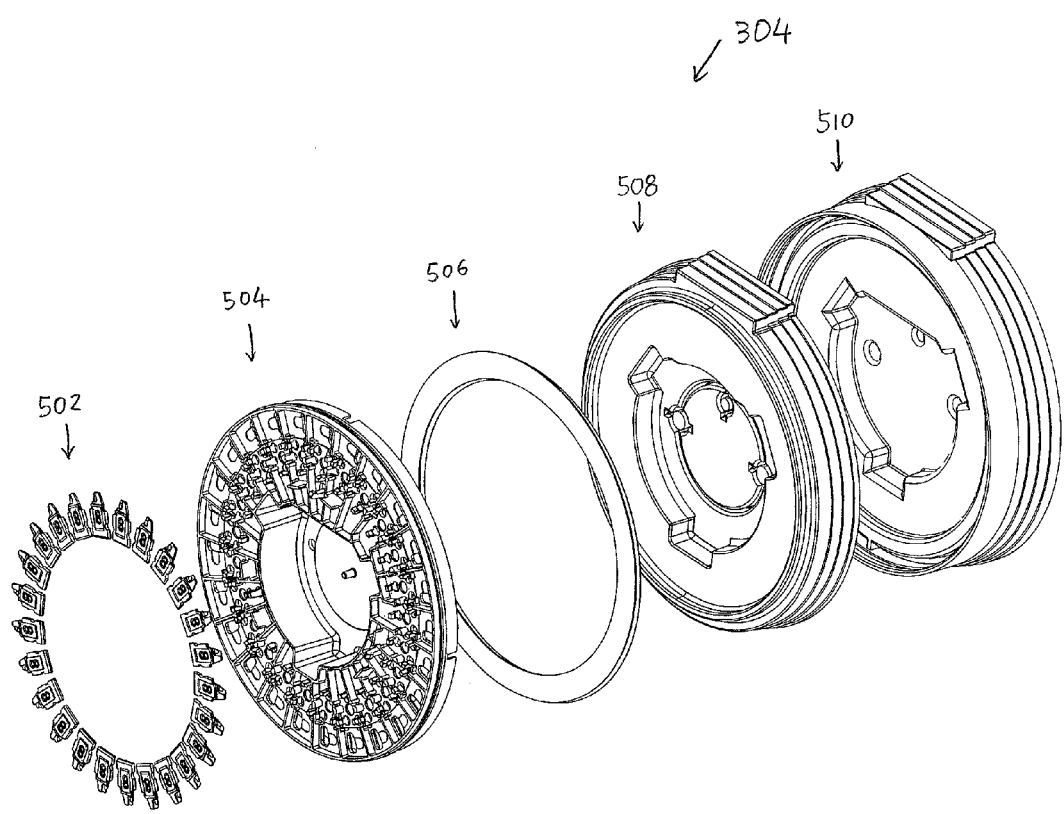
FIGS. 5A-5B depict the components of one embodiment of a sensor disk.

As described in FIG. 1, sensor disk (190) may be a separate component from the transfer disk (196), but configured to interface with the transfer disk (196) via a mechanical lock. Some variations of the disk assembly (300) shown in FIG. 3 may comprise a sensor element, such as sensor disk (304). In other embodiments of the disk assembly, the sensor component may also be any assembly enclosed in a housing, or may be an assembly of multiple cassettes, cartridges, or disks. FIG. 5A depicts one variation of a sensor disk (304). Sensor disk (304) includes a plurality of test substrates (each configured to receive a sample) and/or test sensors (each configured and analyze a fluid when it mixes with chemicals, reagents or interacts with other components of a test sensor or test substrate). The sensor may be electrical, electrochemical, optical, or optoelectronic, for example. In some variations, sensor disk retains an array of test sensors such that each test sensor is configured to receive a fluid sample from a single transfer reservoir. A sensor disk (304) may comprise test sensors (502), a sensor disk structure (504), and an absorbent lamina (506). The sensor disk structure (504) is made of molded acrylic, but may be made of any material with similar structural and optical properties. Some or all components of the sensor disk (304) may be sterilized, however, in some variations, the test sensors (502) may not be able to be sterilized without compromising shelf-life, reliability, and/or accuracy. Some variations of the sensor disk (304) may comprise absorbent lamina (506) to retain any excess fluid that may be transferred from the transfer reservoir to the sensor disk. This may prevent cross-contamination between test sensors (502). The absorbent lamina (506) may be comprised of any absorbent material (505), for example a polyester/cellulose nonwoven blend, and be secured by a rigid structure (507) that is sized and shaped to fit with the sensor disk structure (504). The sensor disk structure (504) comprises apertures that allow the fluid sample to contact the absorbent material (505), for quick and even absorption, without contacting the transfer reservoir outlet or test substrate of other test sensors (502).

Certain types of test sensors (502) may be maintained in a relatively moisture-free environment to extend shelf-life and test accuracy. Some variations of a sensor disk (304) may comprise desiccating features, for example, a desiccating material (508) and a desiccant cap (510) to maintain a moisture-free environment in the sensor disk. The desiccant material, such as molecular sieve, silica gel, or any clay-based granular desiccant, may be contained in the airspace between the desiccant sieve (508) and desiccant cap (510). The quantity and type of desiccant to include may be determined by the anticipated moisture influx that the sensor disk may be expose to during its course of its shelf-life and use. Some variations of the sensor disk (304) may also comprise a humidity sensor (167j), as depicted in FIG. 1, that communicates humidity data to the control system (185) so that the test sensor reading may be adjusted according to the humidity in the sensor disk (304). For example, the readings from glucose test sensors may need to be adjusted according to the humidity level over time. Excessively humid or excessively dry sensor disk environments may render the test sensors (502) inaccurate, and the control system (185) may instruct the user to replace the sensor disk (304).

RFID Feature

Figure 5B:
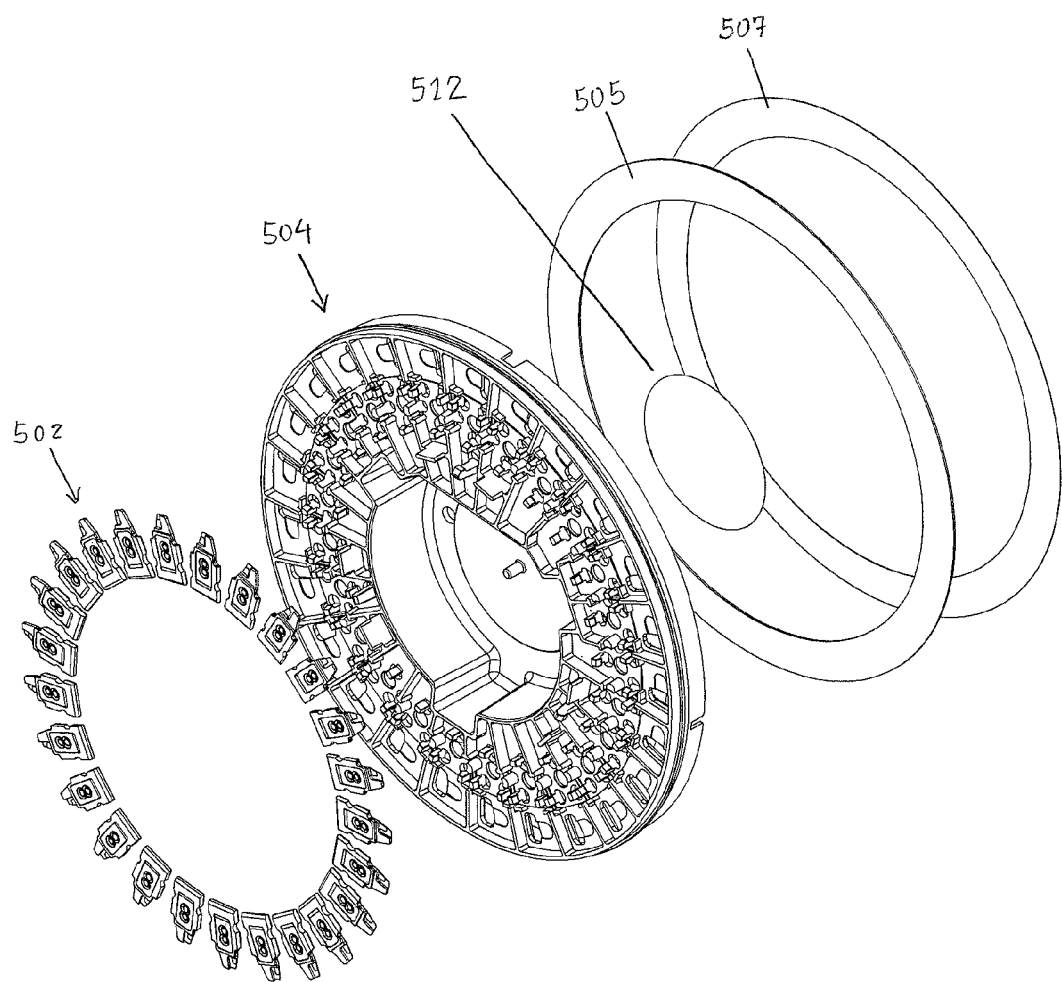

As described previously, some variations of the sensor disk (304) may also comprise machine readable indicia that may be relayed to the control system (185) using an indicia reader. The indicia reader may be, for example, a barcode reader, a radiofrequency identification (RFID) reader, and/or an electrical connection to an EPROM or other chip located on the sensor disk (304). For example, as shown in FIG. 5B, the sensor disk may comprise an RFID chip (512) that communicates with the control system through an RFID serial interface. The RFID chip may contain information, such as the disk type, manufacturing date and time (including batch tracking numbers, factory and operation data), test sensor codes (indicating test sensor quantity, type and expiration date), calibration codes, and sensor disk expiration date. Data may also be written to the RFID. In some embodiments, the RFID may be secured so that it can only be written to by a specific type of fluid monitoring system, and may only be written to once, and optionally encrypted. The types of data that may be written to an RFID by the monitoring system may be the first time of use, any indicators and identifiers of malfunctioning or adverse events (e.g. damage sustained during use), temperature and humidity conditions under which the sensor disk was used. Patient data may also be written to the RFID. In some cases, the data on the RFID may indicate to the fluid monitoring system that the sensor disk is defective or error-prone, and should be replaced. The RFID (512) may also indicate to the control system if the sensor disk is properly installed, aligned, and locked into place. The RFID may also be used to relay calibration curves and other analysis or configuration data to the controller in multiple analyte systems. For example, the rotational/axial position of different analyte sensors may be stored in the RFID so the monitoring system can coordinate the application of appropriate firmware, analytical algorithms, or calibration data to each type of sensor.

Sensor Disk Structure

Figure 5C:
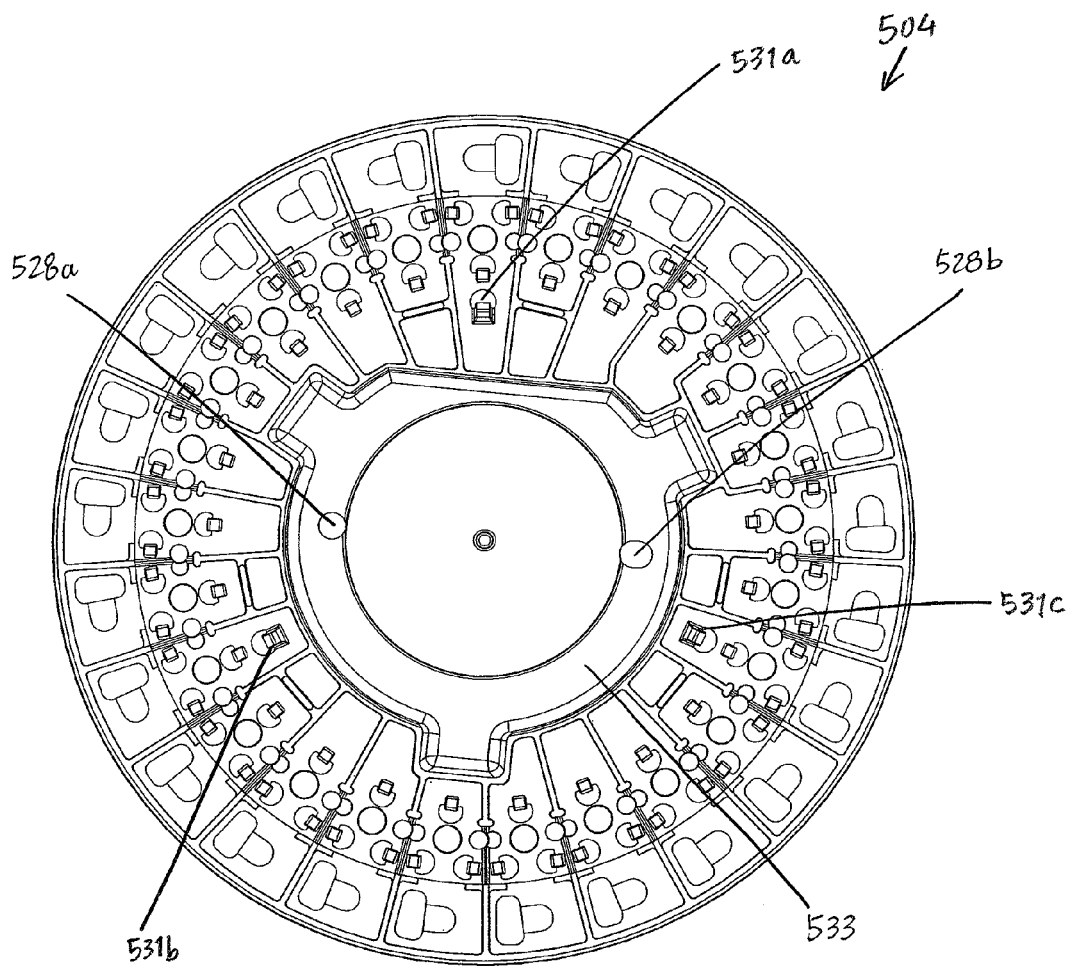
FIGS. 5C-5E depict one embodiment of the sensor disk structure.

Some variations of the sensor disk structure (504) may comprise several alignment features as shown in FIG. 5C. Protrusions or pins may pass through apertures (528a) and (528b) to align components of the sensor disk (304) to the fluid monitoring system. The sensor disk structure (504) may also comprise a protrusion (533) that may engage the sensor disk (304) with other disk components, e.g. the transfer disk. To engage with other disk assembly components, such as the transfer disk, the protrusion (533) for each disk must be sized and shaped to mate with the grooves and protrusions of the other disks. Additionally, these alignment features may also comprise locking features, such as hooks or snap locks (531a-c), which secure the sensor disk (304) to the transfer disk. These locking features may reversibly or irreversibly engage other disk assembly components.

Figure 5D:
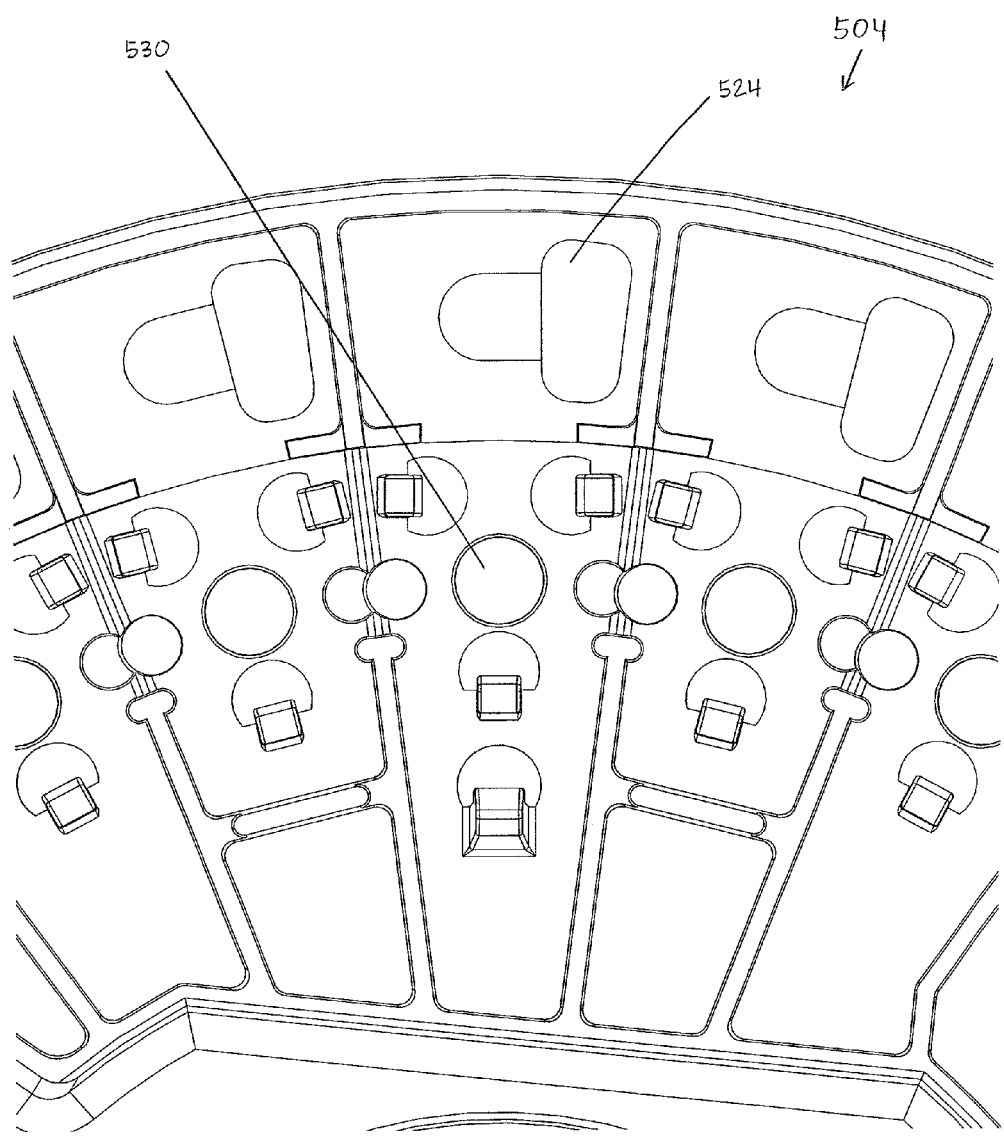
Figure 5E:
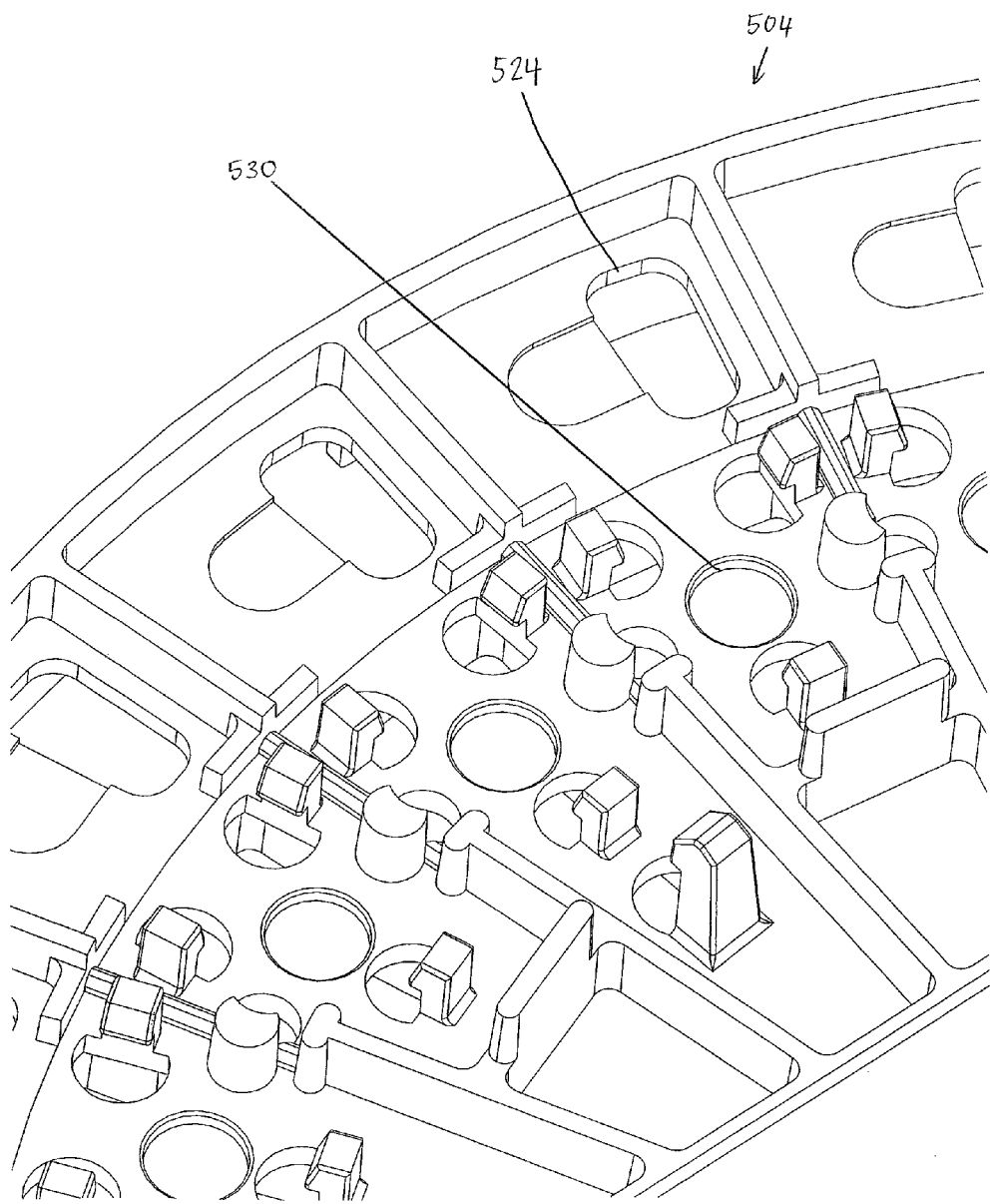

The sensor disk structure (504) may comprise additional apertures for purposes other than alignment, as shown in FIGS. 5D and 5E. For example, aperture (530) is arrayed throughout the sensor disk structure (504) to provide ventilation to facilitate the capillary of the test sensor. Apertures of other sizes and shapes may aid in the precise manufacturing of the sensor disk structure (504), the loading of sensors (502), and may also provide exposure to a desiccant. For example, aperture (524) may expose underlying layers of the sensor disk (304), such as the absorbent material (505), so that the absorbent material (505) may be contacted by fluid that is present in aperture (524).

Figure 5F:
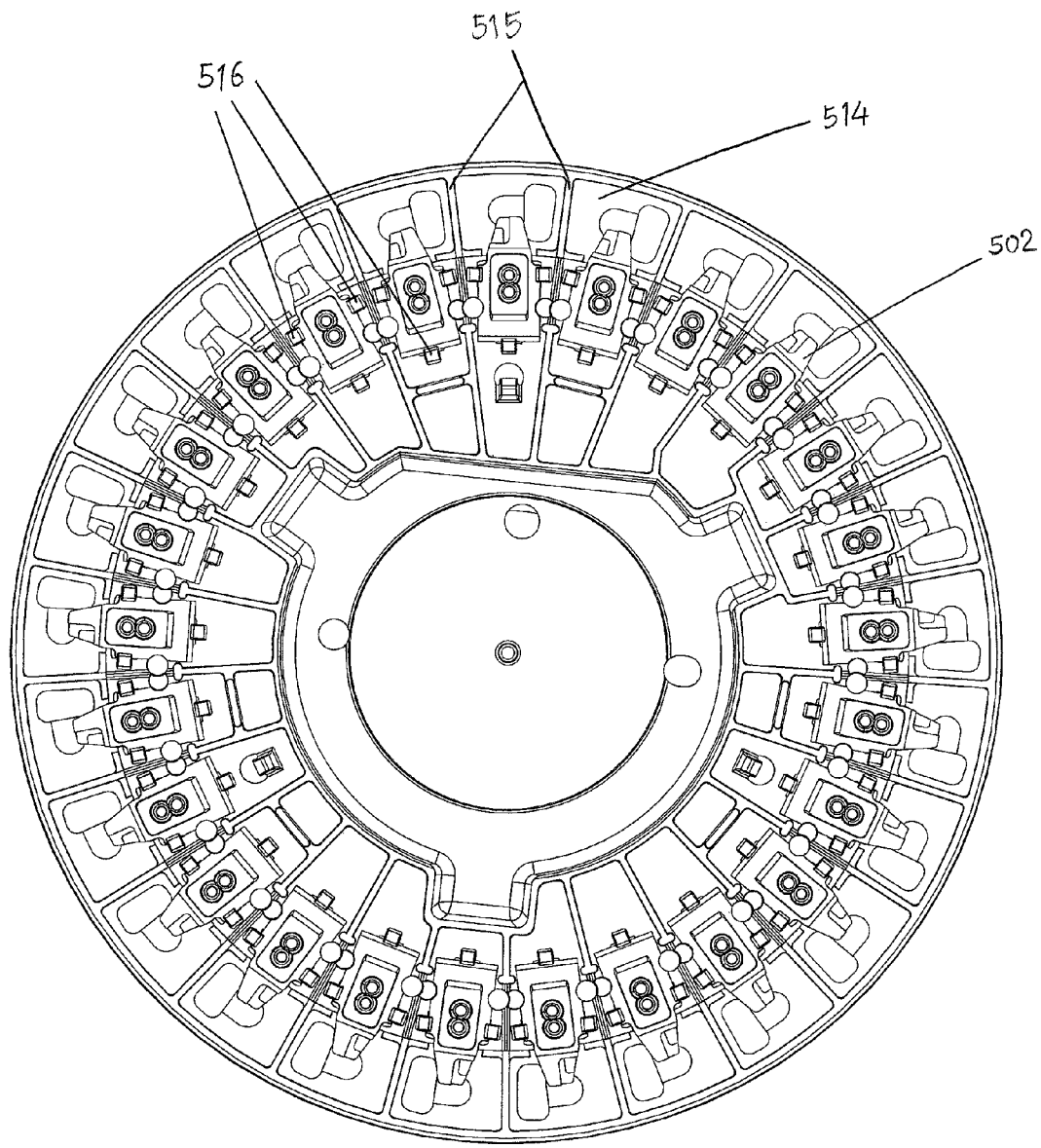
Figure 5G:
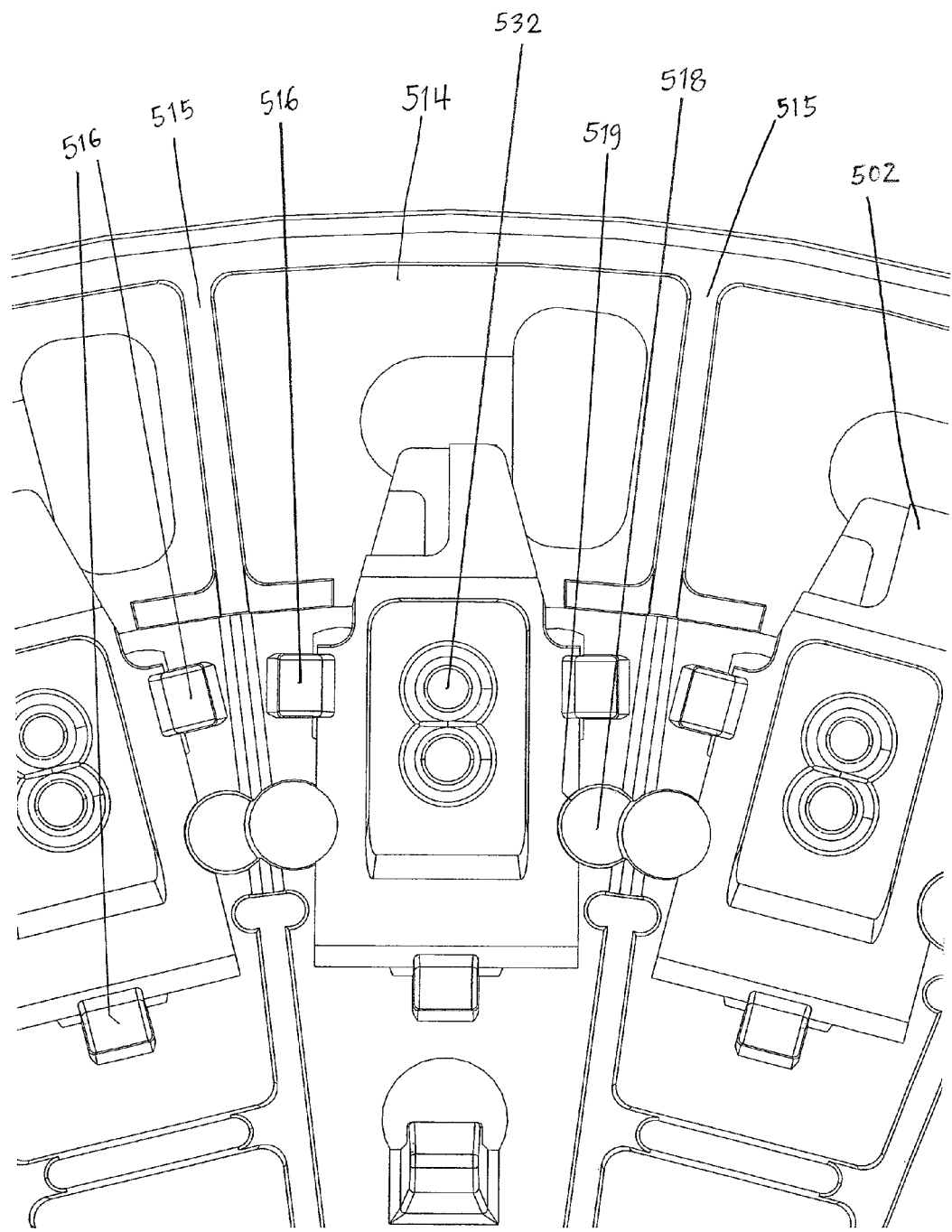
Figure 5H:
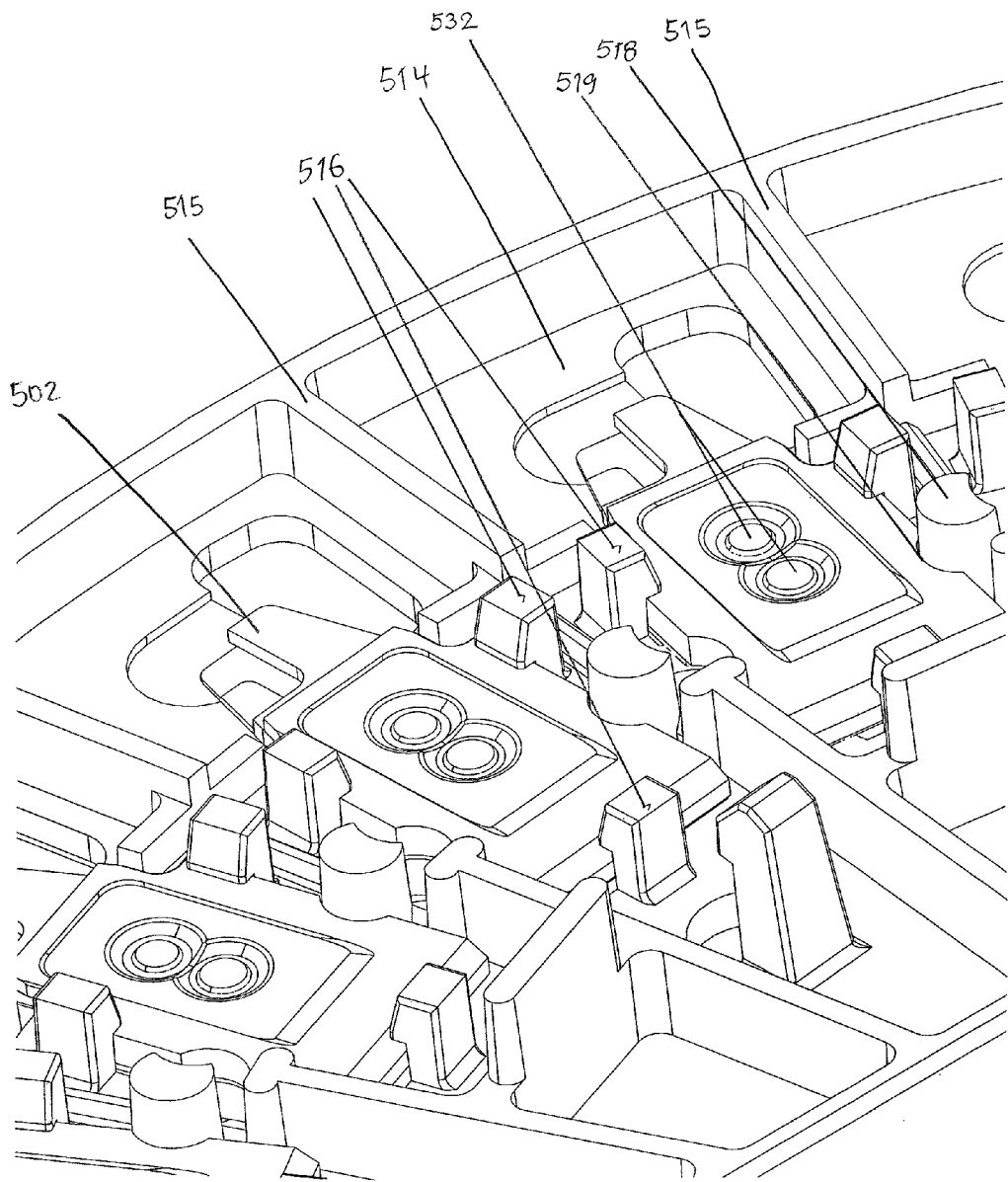
Figure 51:
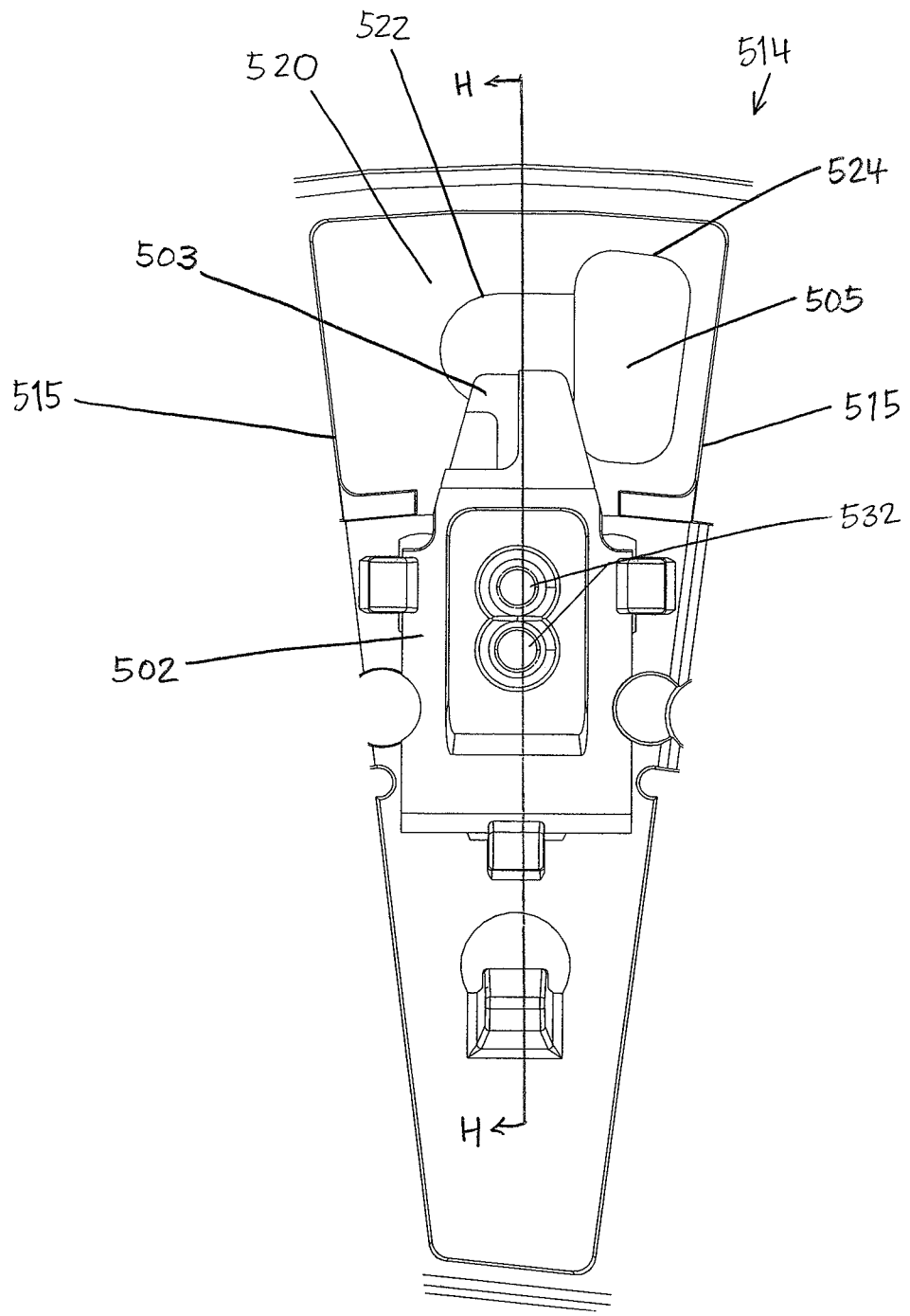

The sensor disk (304) may be configured to retain 25 test sensors (502) as shown in FIG. 5F, but in other embodiments, any other number of sensors may be retained, include but not limited to at least (or no more than) about 5, about 10, about 15, about 20, or about 30 test sensors (502). Additionally, test sensors may be disposed on the sensor disk in multiple coaxial circular patters to double or triple the number of sensors to match a higher density transfer disk as described above. Each test sensor (502) is retained in a semi-enclosed subunit (514) of the sensor disk structure (504). Each sensor disk subunit (514) is separated from the adjacent subunit by a wall (515), which may be of sufficient height to prevent fluid transfer (cross-contamination) between subunits, as shown in FIG. 5H. The test sensors (502) are secured within each sensor disk subunit (514) by several retainer protrusions (516). As shown in FIG. 5G, there are also alignment protrusions (518) that ensure the position of the test sensor (502). In some variations, the alignment protrusion (518) may be sized and shaped to fit a complementary groove (519) in the test sensor (502). For example, a cylindrical alignment protrusion (518) may be used to align a sensor (502) with a semi-circular groove (519).

Figure 5J:
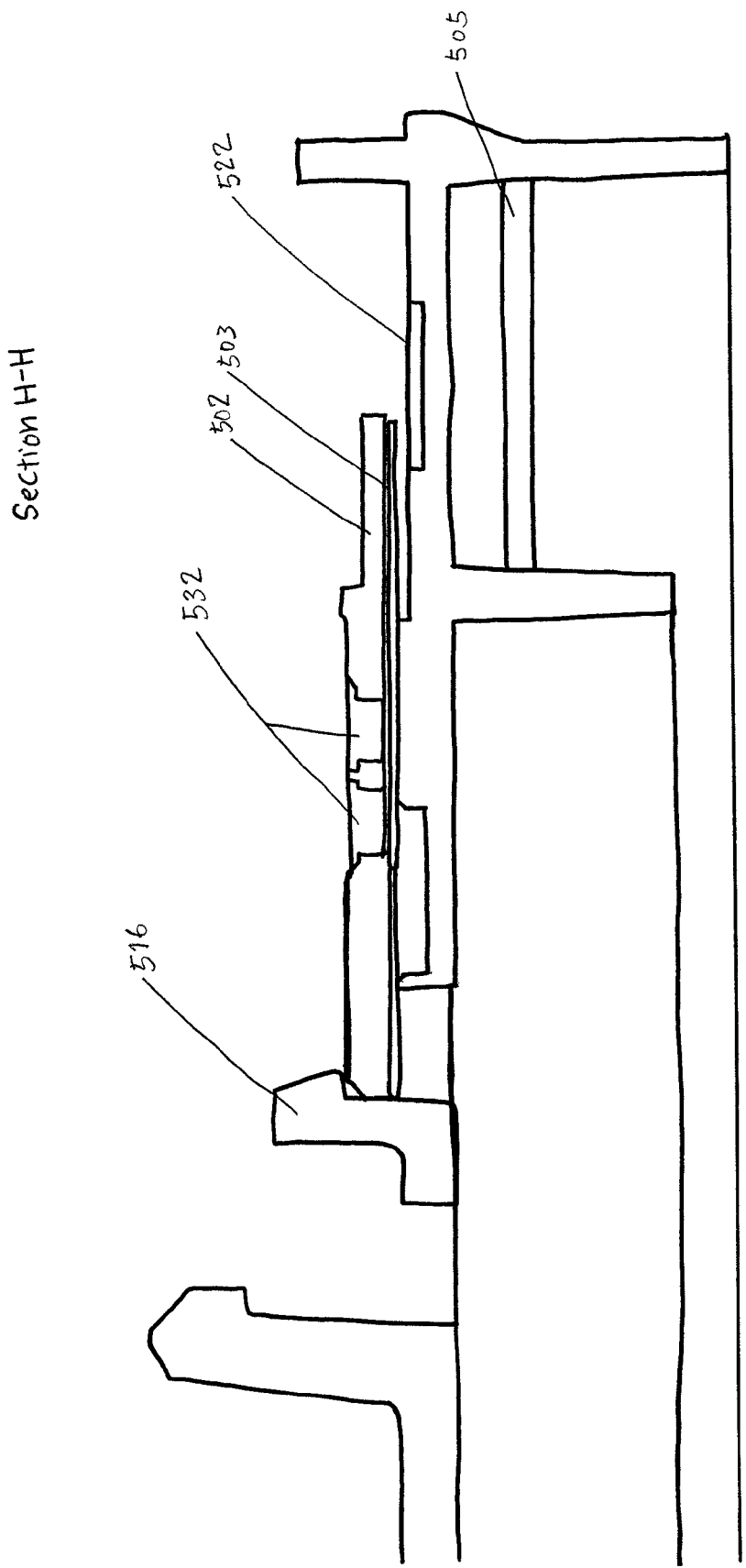

Test sensors (502) may comprise a sensor substrate (503) and electrode contacts (532), depicted in FIGS. 5I and 5J. The sensor substrate (503) reacts with the fluid sample, which forms an end product that is indicative of the quantity of the analyte in the sample. This measurement may be communicated to the control system via electrode contacts (532). For example, blood glucose sensors may receive blood which reacts with the sensor substrate (503) reagent, and the monitoring system may analyze the glucose content in the blood sample via the electrodes (532). Sensors that detect different analytes may have different test substrates and electrode configurations, and the sensor disk structure (504) may be modified to accommodate the different location of the sensor substrate (503) and electrodes (532). Some variations of sensors, such as certain glucose sensors, may provide additional data to the control system. For example, it may comprise an under-fill or over-fill detection unit that indicates to the control system if a sufficient fluid sample has been received by the substrate.

Each sensor disk structure subunit (514) comprises a fluid sample receiving area (520), depicted in FIG. 5I. Receiving area (520) comprises a groove (522) and an aperture (524). Aperture (524) may open to expose absorbent material (505). In FIG. 5I, the sensor substrate (503) is oriented over the groove (502), however the sensor substrate may be oriented in any way that is suitable for receiving blood from the transfer disk. In some variations of the sensor disk structure (504), groove (522) may be a drain that captures a portion of the fluid sample from the transfer disk outlet, and aperture (524) which exposes absorbent material (505) may wick up any overflow fluid from the groove (522). Positioning the sensor substrate (503) over the groove (522) may permit immediate access to the transferred fluid sample, before the fluid sample is absorbed by material (505). In some variations, the test sensor substrate (503) is not in direct contact with groove (522), and takes up the dispensed fluid sample by capillary action.

Figure 5K:
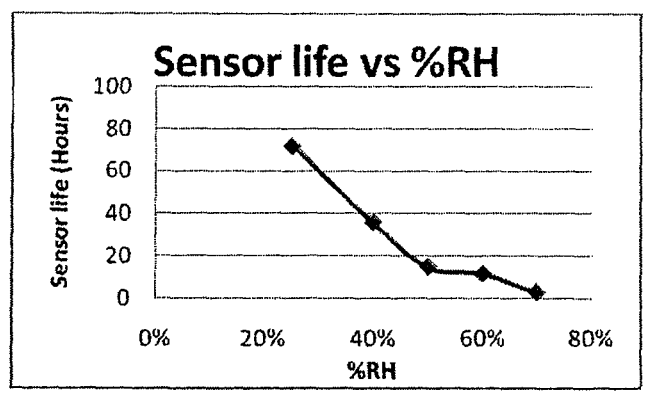
FIG. 5K depicts an example of a shelf-life vs. humidity curve.
Figure 5L:
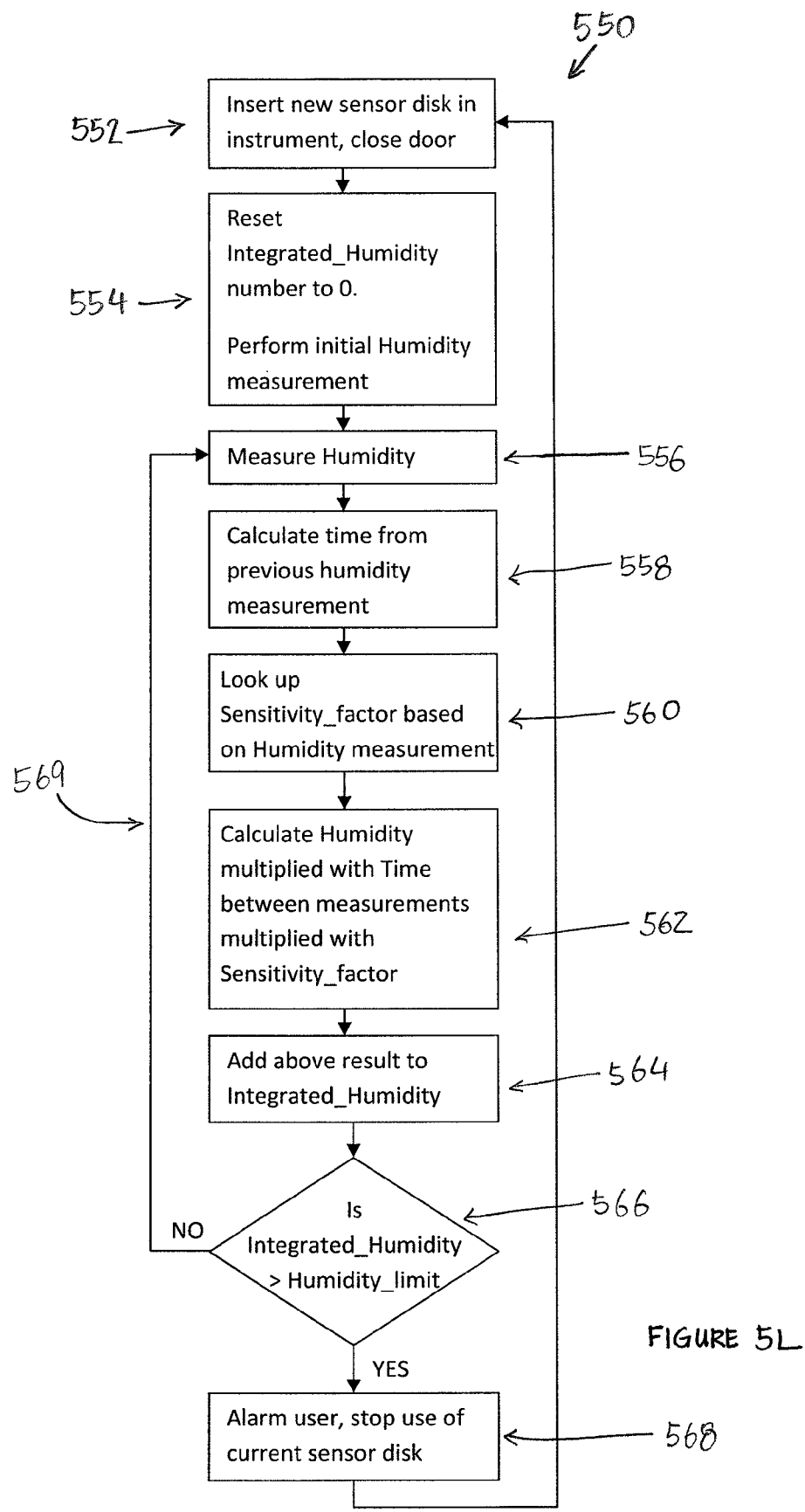
FIG. 5L depicts an integration routine that may be used to estimate the shelf-life of test sensors under changing humidity conditions.

The shelf-life of some types of test sensor substrates are sensitive to humidity and/or temperature. Some variations of a fluid monitoring system may comprise at least one humidity sensor, as shown in FIG. 1 (for example, humidity sensor (167j)), near the installation site of the sensor disk. However, in other variations of a fluid monitoring system, the humidity sensor(s) may be located anywhere in the system, for example, away from the installation site of the sensor disk. Humidity sensors may be optionally provided along the walls of the sensor disk or the transfer disk. A variety of humidity sensors may be used, for example, chemical, capacitive, resistive, or thermal conductivity humidity sensors. The humidity sensors may measure absolute humidity, relative humidity, or dew point, and may integrate any such measurements over time to evaluate the moisture content in the air. For example, a chemical humidity indicator, such as a silica gel desiccant, may indicate the cumulative quantity of moisture in the air by changing color. Other humidity sensors may communicate the moisture measurement to the control system (185) through an electrical interface, where the control system may compute the expected test sensor life based on the humidity measurement. In some cases where the humidity measurement may be affected by temperature, a temperature indicator may also be included in the system, or integrated with the humidity sensor. In certain embodiments, sensor life can be plotted against relative humidity (% RH) integrated over time, as shown in FIG. 5K. Temperature may also impact a sensor's shelf-life, and plots similar to that shown in FIG. 5K may be generated at different temperatures. The control system may monitor the humidity of the sensor disk before use, and integrate the humidity level over time, where the integration is weighted depending on the sensitivity at the different humidity levels. At a given humidity, the rate of sensor life degradation may be determined according to the plot in FIG. 5K. For example, as each hour passes (or any time unit), the control system may poll (at any suitable frequency) the humidity measurement, and adjust its evaluation of sensor life based on the current humidity measurement. In some cases, the relationship between % RH and sensor life may be linear, while in other cases, it is non-linear (e.g. may contain a series of linear regions where the linearity coefficient varies with relative humidity, or may be non-linear across the entire range of % RH). For example, the shelf-life of a sensor at 70% relative humidity (% RH) may be about 20 times shorter than at 25% RH. If there is a non-negligible temperature shift in the course of the use of the sensors, the relationship between sensor life and % RH may be altered, e.g. % RH axis shift, and/or linearity coefficient shift, etc, and the computation for the expected shelf-life may incorporate this temperature effect. An example of a humidity integration routine (550) the system may perform to evaluate test sensor life is depicted in FIG. 5L. After the sensor disk is installed in the system (552), the integrated humidity level is reset to zero and the first humidity measurement is taken (554, 556). Another humidity measurement is performed after a certain period of time. The control system then determines how much time has elapsed since the previous humidity measurement (558). Based on the humidity measurement, the sensitivity factor is computed based on a plot of sensor life as a function of humidity, shown in FIG. 5K. The sensitivity factor at a given % RH is 100% divided by total sensor life at that % RH. The routine (550) then computes the product of current humidity measurement, elapsed time, and sensitivity factor (562). This result is added to the integrated humidity level (which is initially zero) in step (564). At that point, the routine will compare the integrated humidity level against the maximum limit, e.g. at or around 100% (566). If the integrated humidity is below the maximum limit, then the routine will loops back to step (556) and iterate at a pre-determined frequency, e.g. once per minute, once per 10 minutes, etc, until the sensor life expires due to elapsed time or increased humidity. If the integrated humidity is near 100%, the system may issue a warning signal to the user. When the integrated humidity is at or exceeds 100%, then the sensor will be considered inaccurate and/or unfit for use, since the expected shelf-life has been exceeded (which may be due to, for example, elapsed time, or changes in humidity or temperature). Once the sensors have exceeded their shelf-life, the system may issue an alert or alarm to remove or discard the sensor disk. Other computational methods and routines may be used to dynamically update the expected shelf-life of the sensors. The control system may poll the humidity sensor when the sensor disk is installed and determine if the sensor disk is suitable for use, given the measured humidity (and temperature, for certain embodiments). If the sensor disk is determined to be unsuitable for use, the system may issue an alarm to remove the sensor disk. The relative humidity may also be plotted against other sensor factors, such as sensitivity, accuracy, and/or precision. For example, a plot similar to FIG. 5K may be generated that relates % RH to sensor sensitivity, which may be used to adjust the readings from the sensors to compensate for shifts in humidity and/or temperature. In certain embodiments, humidity sensors as described above are provided in a plurality of locations throughout the fluid monitoring system, such as the PL cartridge, the transfer disk, the sensor disk, etc. If excessive humidity is a result of moisture that originates from within the system, a plurality of humidity sensors in the system may provide sufficient information to the control system to localize the source of humidity and flag an indicator to remove the moisture source.

Interface Between Transfer Disk and Sensor Disk

Figure 6A:
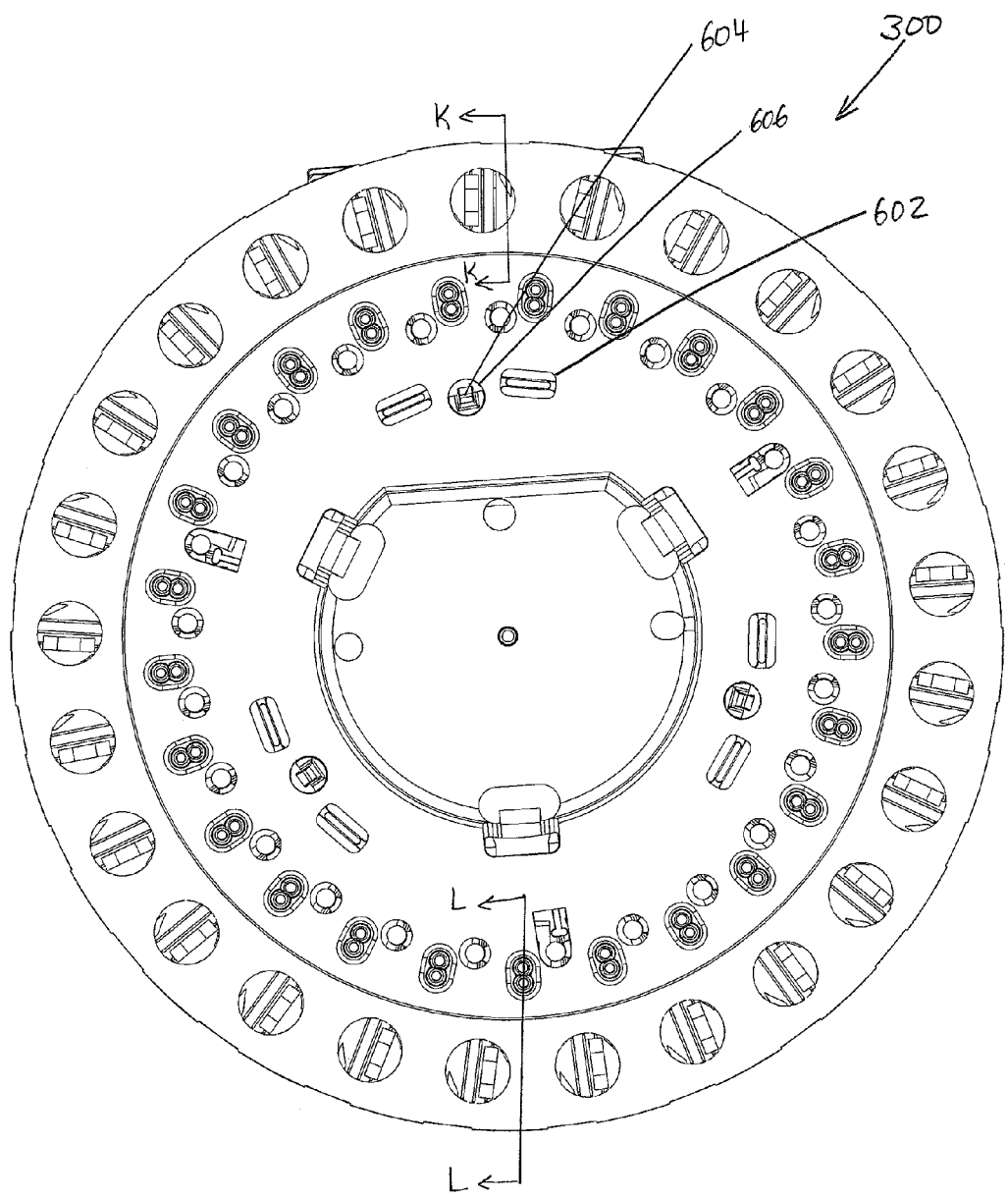

As described previously, in some variations of a fluid monitoring device, the disk assembly may comprise a transfer element and a sensor element, either enclosed in a single housing, or separated as individual cassettes, cartridges, or disks. The variation of disk assembly shown in FIG. 6A comprises a transfer disk and a sensor disk which are secured and actuated together. FIG. 6A depicts features such as slots (602), apertures (606), and protrusions (604) that are configured to secure the transfer disk and sensor disk together. Either or both the transfer disk and sensor disk may be sterilized individually or in combination. The transfer disk and the sensor disk may be permanently secured together, and may be removed from the system and disposed between patients. The sensor disk may be disposed of when the sensors have expired (i.e. exceeded their shelf-life) or all of the sensors have been used. Either the sensor disk or transfer disk may be disposed of (individually or together) if contaminated or previously used.

Figure 6D:
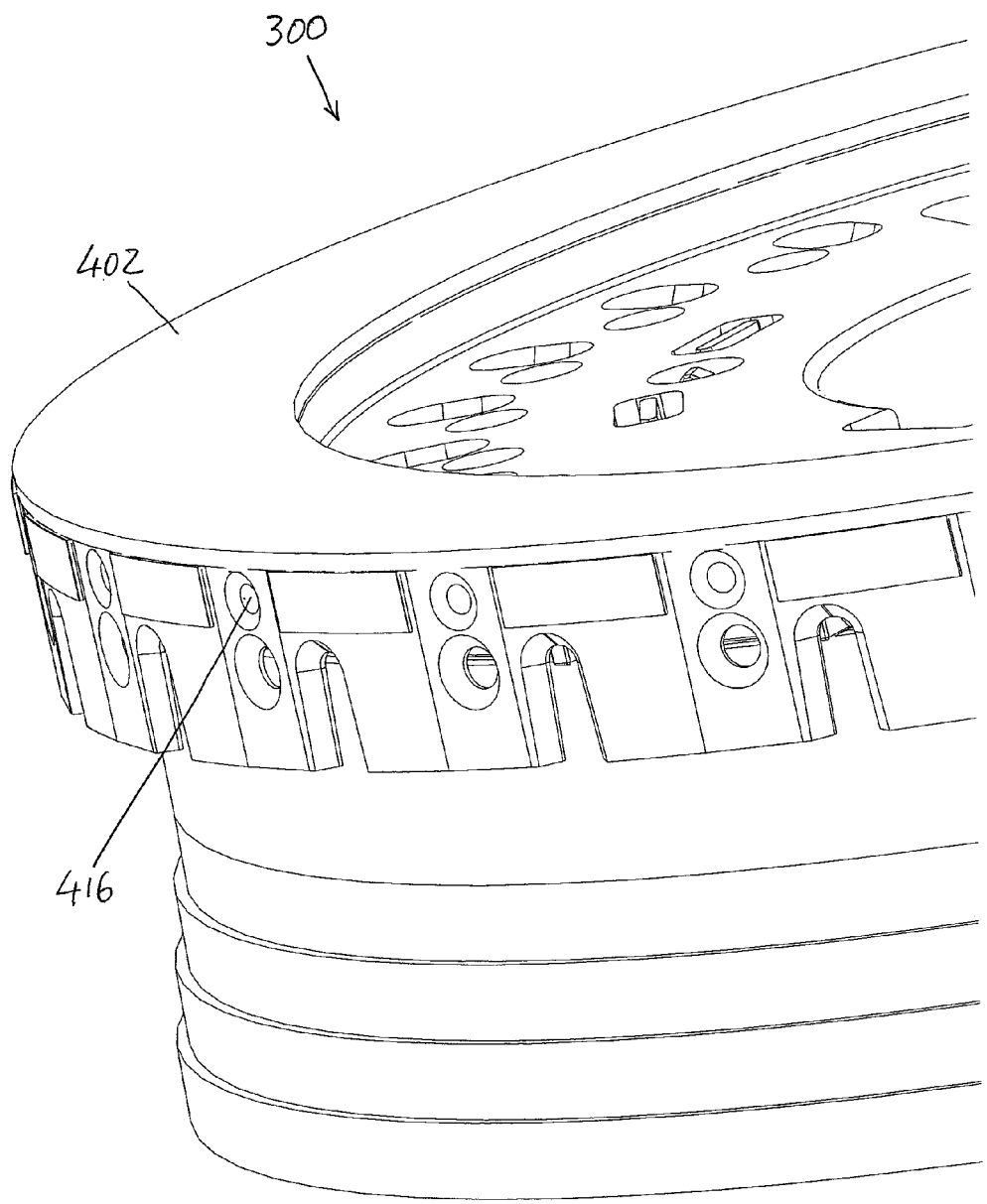

In certain variations of the disk assembly (300) as shown in FIG. 6B, the outer edge of the transfer disk (302) juts out or protrudes from the sensor disk (304). The gap (613) provides clearance for alignment features. Edge (621*a*) on the transfer disk articulates with edge (621*b*) on the sensor disk, which aligns the two disks and ensures that there is adequate clearance between the two disks. In the variation shown in FIGS. 6B and 6C, there is sufficient clearance such that no portion of the transfer disk contacts the test sensors (502). In FIG. 6C, the outlet (418) from the transfer disk (302) is positioned directly over, but not touching, the sensor substrate (503), separated by gap (623). The gap (623) may be between the transfer disk and the sensor disk for a portion of the fluid path to a test location of the test substrate or test sensor. The disk assembly (300) may also include an access interface for the system to contact the test sensor electrodes (532). In some variations, an aperture is provided for external reading elements to access electrodes (532), while in other variations, the electrode reading elements may remain entirely internal to the disk assembly (300). As shown in FIGS. 6B and 6C, the test sensor (502) is not in contact with the transfer disk (302). The disk assembly (300) may comprise a membrane (402) depicted in FIGS. 6B-6D. In some variations, the membrane (402) is silicone, and stretched over the perimeter of the disk assembly (300) such that the membrane forms a fluid-tight seal with the transfer disk transfer reservoir (408), however, the membrane (402) may be made of any other material with similar properties, such as a malleable metal alloy. The membrane (402) may have varying degrees of elasticity and may be stretched over the transfer reservoir (408) with varying degrees of tension.

Interface Between Disk Assembly and Patient Line Cartridge

Figure 7:
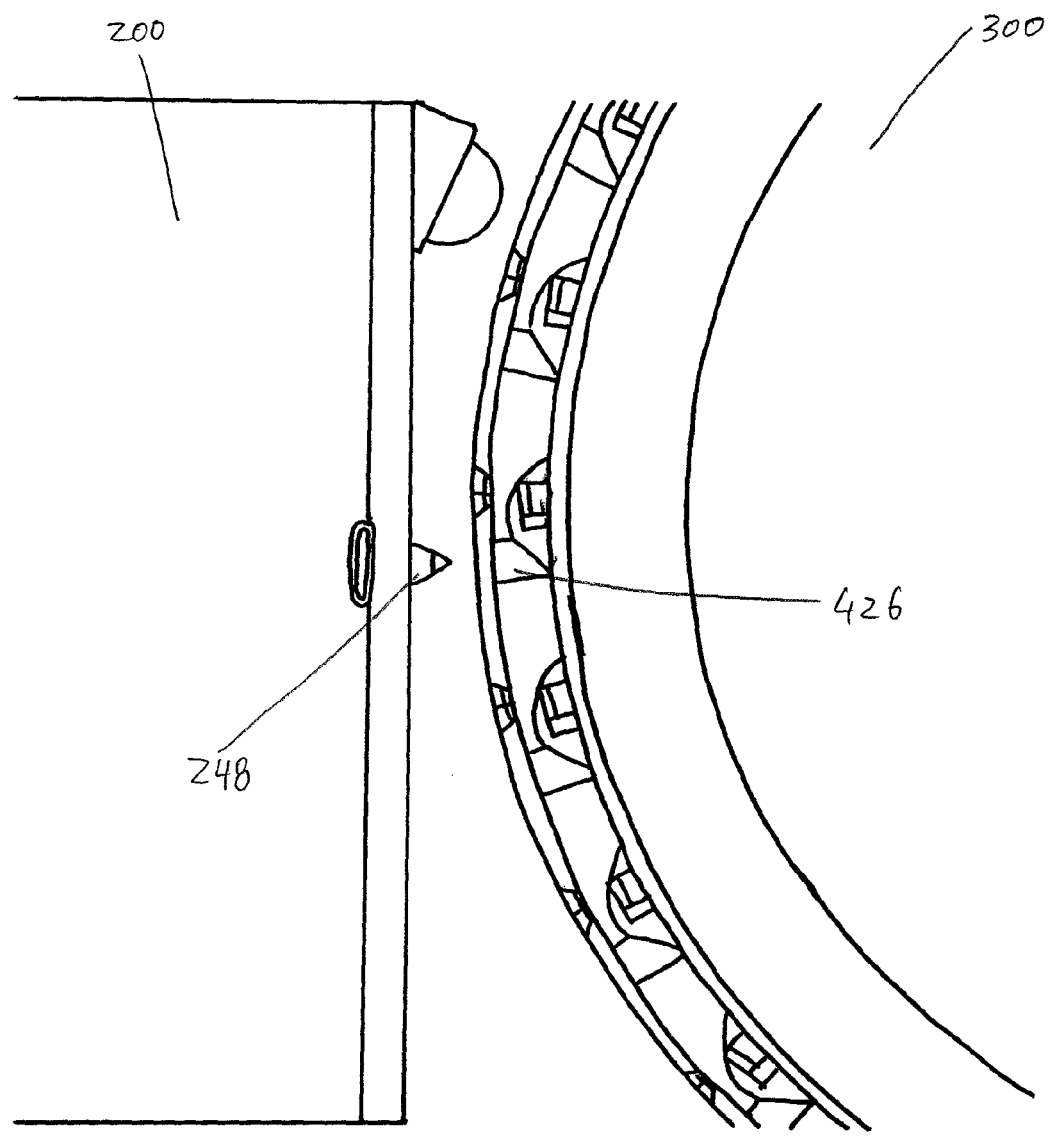
FIG. 7 depicts a possible load configuration of the PL cartridge and disk assembly.

In some fluid monitoring systems, the disk assembly (300) is installed with minimal contact with other system elements as shown in FIG. 7. For example, disk assembly (300) may be installed to maintain an air space or gap between the alignment aperture (426) and alignment protrusion (248) of the PL cartridge (200). This ensures that the dispense nozzle (246) of PL cartridge and the inlet of the disk assembly (300) (not shown in FIG. 7) also maintain an air space. Such a load configuration may be useful for some variations to maintain the sterility of either the PL cartridge (200) or the disk assembly (300). Other load configurations may be used as appropriate for other disk assemblies and PL cartridges, depending on the degree of sterility that is desired.

Some variations of a fluid monitoring system may include mechanisms that prevent the installation and use of an inappropriate PL cartridge (200), such as an incompatible part, or a previously used PL cartridge. For example, when there is no PL cartridge the fluid monitoring system, the alignment and/or lock features of the fluid monitoring system may be in a "load" configuration. Only PL cartridges that are also in a matching "load" configuration can be installed in the system. This mechanism may be implemented in the dispense valve, where the "load" configuration is one that is not used during the operation of the PL cartridge. Other sub components may carry out this lock-out function.

Operational Configurations

Once the PL cartridge and disk assembly have been installed into the system according to the various alignment and locking features, the system may undergo an initialization and/or diagnostic procedure. The initialization or diagnostic procedure may involve polling and testing all system sensors (temperature, humidity, pressure, air-in-line detector, blood detector, etc) to ensure that every sensor is properly calibrated, installed, and initialized. Initialization may also include priming the tubing system within the PL cartridge, for instance, perfusing a cleaning solution or saline into all the tubing. This perfusion step may serve to reduce or eliminate the air in tubing and may rinse away any residual manufacturing agent. The perfusate may then be flushed out of the system through a waste portal. The initialization procedure may also include reading the RFID components of the PL cartridge and disk assembly as previously described. The information read from the RFID components may be incorporated by the control system to adjust the operation of the fluid monitoring system, and may also confirm that the PL cartridge and disk assembly have been properly aligned and installed. The control system may also have data from a look up table, e.g. provided by disk assembler, manufacturer or transporter concerning lot numbers, initial lot calibration information, dates of assembly, production or transport information, etc. This information may be downloadable or otherwise provided to a user of the instrument.

Dispense Configuration

Figure 8A:
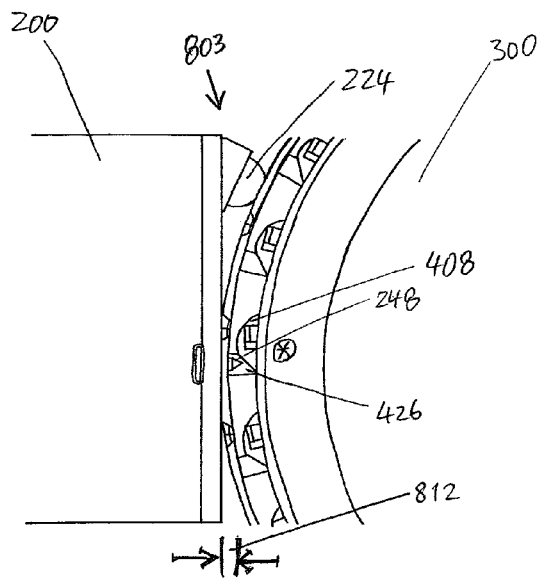
FIGS. 8A-D depict different functional configurations (such as dispense, withdraw, index, and wipe) of the PL cartridge and disk assembly.
Figure 8B:
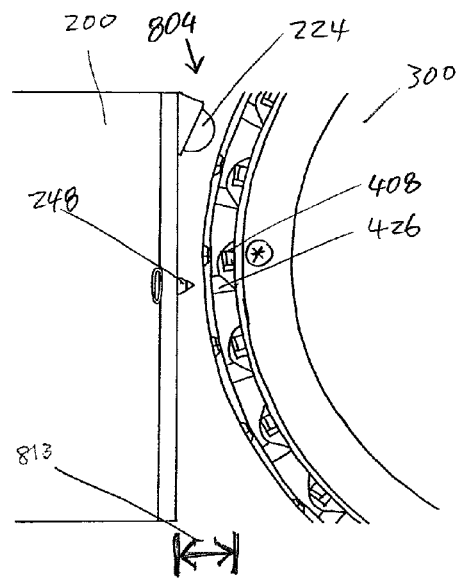

After the initialization procedure has successfully completed, PL cartridge (200) and disk assembly (300) may be placed in a fluid dispense configuration (803), as shown in FIG. 8A. In the dispense configuration (803), the alignment protrusion (248) on the PL dispense valve is inserted in the alignment aperture (426), which ensures that the dispense nozzle positioned to deliver a fluid sample to the transfer disk inlet (not shown) to the transfer disk transfer reservoir (408). Once such alignment is confirmed, the control system may signal to the PL cartridge to dispense a fluid sample to the transfer reservoir (408) of disk assembly (300). The asterisk in FIGS. 8A-8D marks the transfer reservoir that received the sample in FIG. 8A. The fluid channel plug (224) may or may not be aligned with transfer disk inlet. In dispense configuration (803), the PL cartridge (200) and the disk assembly (300) may be in close proximity (812) to each other.

Withdrawal Configuration

After a desired quantity of fluid has been dispensed to the disk assembly (300), as sensed by a fluid sensor in the system, e.g. within the transfer disk transfer reservoir (408), the control system (185) may issue a command to the PL cartridge to cease the fluid flow. Then, the PL cartridge (200) and/or the disk assembly (300) may be manipulated so that the distance between then is increased (813). In the withdraw configuration (804), the distance (813) may be large enough to separate any fluid connection that may remain between the PL cartridge and disk assembly after the PL cartridge has ceased the fluid flow. In some variations, the distance between the PL cartridge and disk assembly in the withdraw configuration (804) may be small, but large enough so that the individual components may be advanced or rotated without impacting the other. In the withdraw configuration (804), the fluid channel plug (224) may not be in contact with the disk assembly (300).

Indexing Intermediate Configuration

Figure 8C:
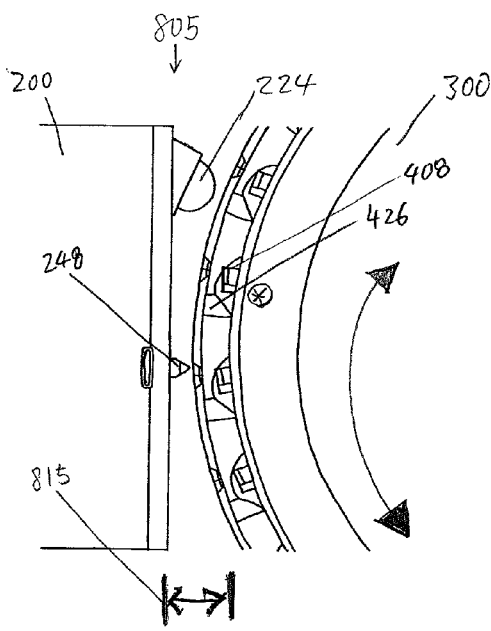

Some variations may have an indexing intermediate configuration (805) where the disk assembly (300) is advanced with respect to the dispense nozzle. An example of a position in the intermediate configuration (805) is shown in FIG. 8C. This may be achieved by rotating, translating, or pivoting the disk assembly (300), and/or manipulating the PL cartridge, so that the dispense nozzle (246) and alignment apertures (426) is moved towards a transfer reservoir (408) other than the one just accessed. The distance (815) between the PL cartridge and disk assembly may be large enough so that the disk assembly and PL cartridge may be rotated separately without substantial contact. The fluid channel plug (224) may not be in contact with the disk assembly (300). The indexing intermediate configuration (805) may rotate the disk assembly (300) any number of steps to any transfer reservoir (408), consecutive or otherwise, on the disk assembly. For example, the disk assembly (300) may be rotated clockwise or counterclockwise, in any order, and any number of degrees (e.g. about 10°, 13°, 25°, etc). In some fluid monitoring systems, the control system (185) may maintain a lookup table to track which transfer reservoirs have already been accessed, and may be programmed to access to a transfer reservoir only once. The sequence and degree of rotation may be determined by the positioning and number of transfer reservoirs on the disk assembly. In certain variations, the sequence and degree of rotation may prevent the contamination of wipes. The lookup table may also contain information about the type of sensor located at each index position, and based upon user input, (or upon information in a look up table accessible by the controller and corresponding to RFID lot number) may advance the disk assembly so that the fluid is dispensed to the transfer reservoir that transfers the sample to the desired sensor type.

Wipe Configuration

Figure 8D:
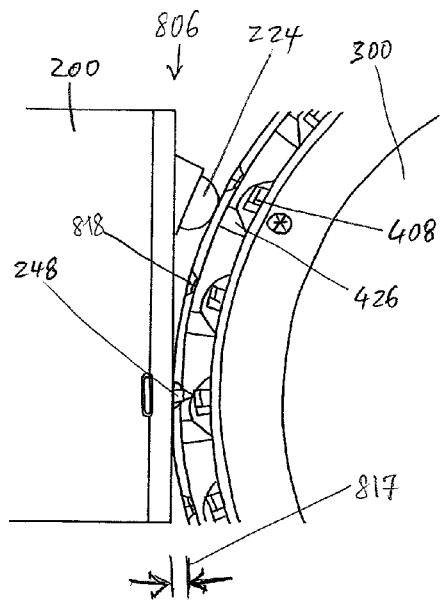

In some variations of a fluid monitoring system, a wipe configuration (806) may follow the index configuration (805), as shown in FIG. 8D. The wipe configuration (806) that positions the alignment protrusion (248) in a notch (818), which may also position the dispense nozzle in contact with a wipe (not shown). In wipe configuration (806), the fluid channel plug (224) may be occluding the inlet to a transfer reservoir (408) that may contain a fluid sample, preventing any back flow of fluid from the transfer reservoir. In this configuration (806), the fluid sample may be transferred to the test sensor substrate by any mechanism, for example, pumping, pushing, or gravity feed. The distance between the PL cartridge and disk assembly may be reduced from the previous configuration (e.g. the withdraw (804) and/or index intermediate (805) configuration), such that the alignment protrusion (248) is fully inserted into notch (818), and the dispense nozzle is in substantial contact with a wipe (not shown). The control system (185) may maintain a lookup table that tracks which wipes have been previously used.

Fluid Transfer Path

Figure 9A:
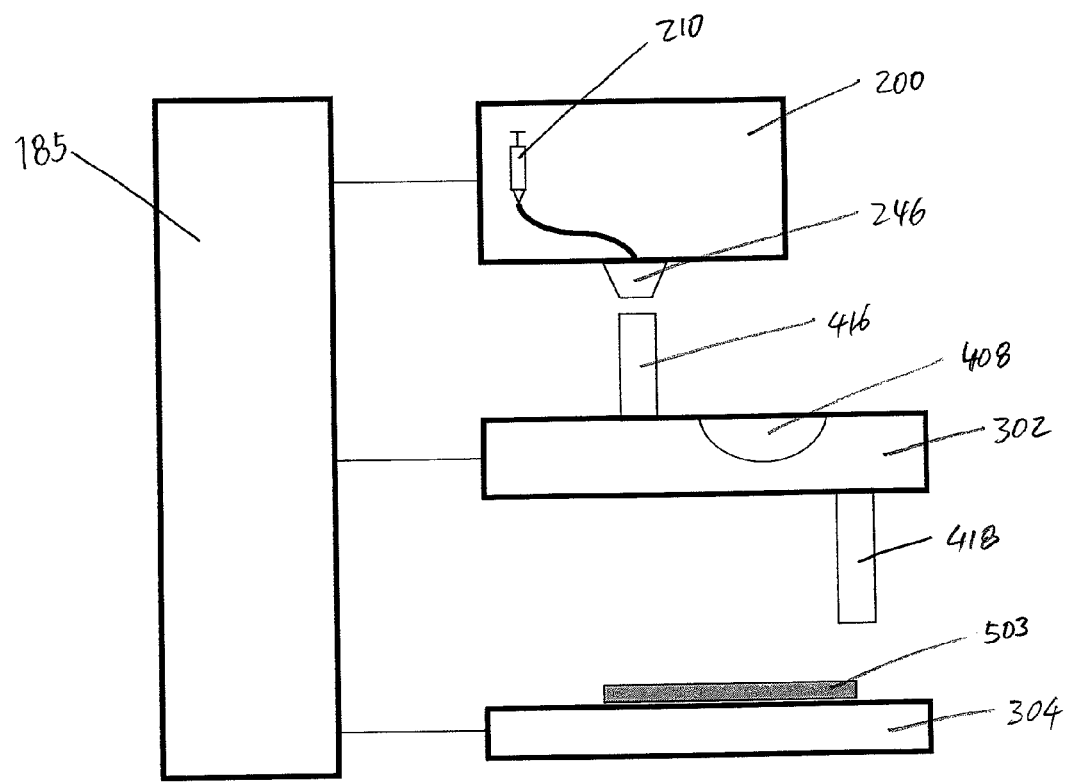
FIGS. 9A-9C depict the various mechanisms that regulate fluid flow from the PL cartridge to the transfer disk to the sensor disk.

As depicted in FIG. 9A, the control system (185) may regulate the timing and fluid flow in various stages in the PL cartridge and disk assembly. After the fluid sample (e.g. blood) is obtained from the source (e.g. a patient), the sample is first accumulated in the PL cartridge (200), for example, in fluid channels or a reservoir. The control system (185) may hold the sample in the PL cartridge (200) as long as desired, and may withhold the sample from testing if sample contamination is suspected. When the control system (185) configures the disk assembly to receive the sample, the sample may be dispensed from the dispense nozzle (246) to the transfer disk (302), where it may enter a transfer reservoir (408) via an inlet (416). Once the transfer reservoir (408) has received a sufficient quantity of fluid sample, the control system (185) may then stop the fluid flow from the PL cartridge (200) to the transfer reservoir (408), by closing the dispense valve (206) or adjusting the pressure in the PL cartridge (e.g. by adjusting the syringe pump (210)). Once the fluid flow from the PL cartridge has ceased, the fluid in the PL cartridge and the fluid in the transfer reservoir (408) may be entirely separate fluid entities. However, for some fluids, such as viscous fluids, there may be a fluid connection between the PL cartridge (200) and the transfer reservoir (408) even after the fluid flow from the PL cartridge has been stopped. In such a circumstance, if complete fluid separation is desired, the control system (185) may advance the disk assembly away from the dispense valve (206), as described below. The control system (185) may hold the sample in the transfer disk (302) as long as necessary, and may withhold the sample from testing if sample contamination is suspected. When the control system (185) determines that the sensor disk (304) is ready to receive the fluid sample, the sample may be transferred from the transfer reservoir (408) to the sensor substrate (503). The fluid from the transfer reservoir (408) may be transferred to the sensor substrate (503) through various methods, for example, gravity feed or pumping or otherwise actively moving a sample, as described previously.

As previously mentioned, the timing of fluid transfer from the PL cartridge (200) to the transfer disk (302) to the sensor disk (304) may be regulated by the control system (185). The control system (185) may execute different system functions between the stages of the fluid flow. For example, after the transfer of fluid from the PL cartridge (200) to the transfer disk (302), the transfer disk may be advanced so that a different transfer reservoir (408) is positioned near the dispense valve (206). Before the fluid is moved from the transfer disk (302) to the sensor disk (304), the control system (185) may execute a calibration procedure to ready the sensor substrate (503) for sample testing. Any system configuration may be utilized to regulate the quantity, direction, and rate of fluid flow to optimally monitor analytes in the fluid sample. In some variations of a fluid monitoring device, the movement of fluid from a first location to a second location may be regulated so that the fluid connection between them is reduced or eliminated. For example, the fluid flow may be regulated to avoid a continuous fluid column from the sensor substrate (503) to the PL cartridge (200). This type of fluid flow regulation may reduce or eliminate the back flow of any contaminants from the sensor substrate (503) to the patient line.

Figure 9B:
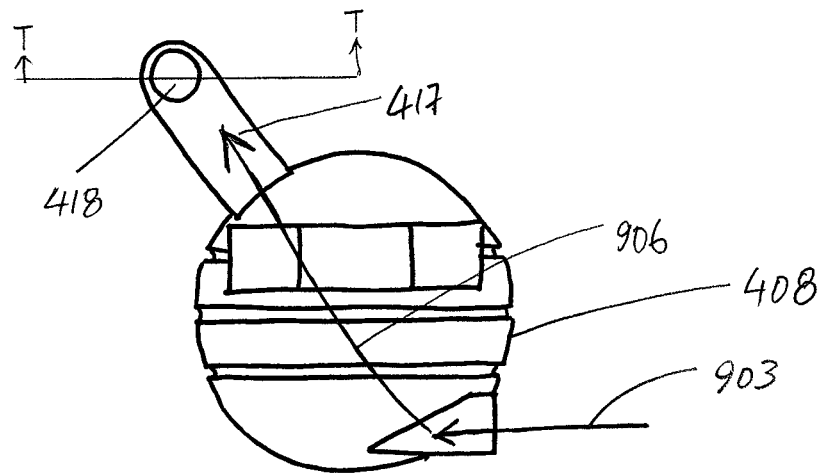
Figure 9C:
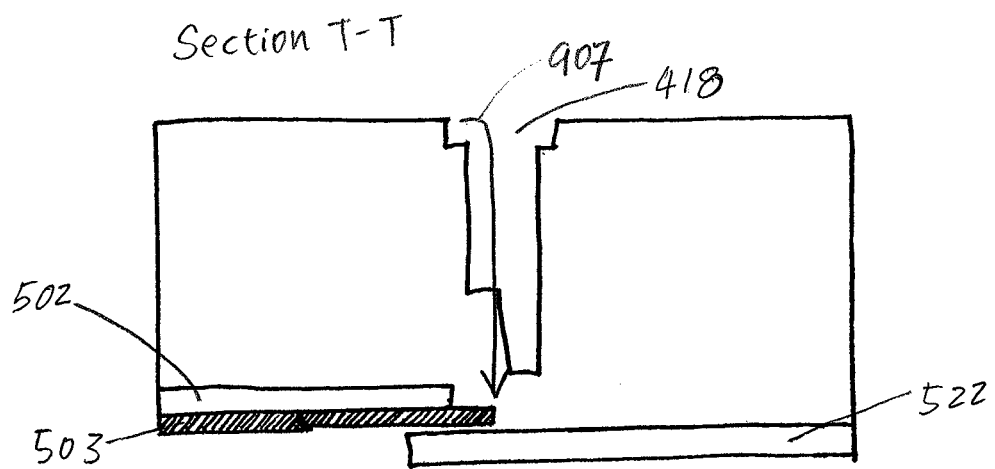

FIG. 9B illustrates an example of the path a fluid sample may take from the PL cartridge to the sensor substrate. Arrow (903) shows the path of the fluid sample from the PL cartridge, through the inlet (901) to the transfer reservoir (408). The fluid is then transferred (by a variety of means, such as gravity feed, by actively moving, displacing or by pumping) in the direction of arrow (906) to the outlet neck (417) to the outlet (418). Cross-section T-T through the outlet (418) shows the path of the fluid sample in the direction of arrow (907) down the outlet (418), towards the test sensor (502). The test sensor substrate (503) may be positioned to receive the fluid sample, for example, at a location directly under or tangential to the outlet (418). Any excess fluid may be captured in a drain (522), and then channeled to an absorbent material that prevents the fluid from contaminating unused test substrates. As previously described, various system functions may be performed between the individual stages of this fluid flow (i.e. the stages indicated by arrows (903), (906), and (907)), such as advancing the disk assembly, calibration procedures, and the like. The fluid sample may also be withheld indefinitely in the PL cartridge or the transfer disk transfer reservoir as desired.

Separation of Sterile & Non-Sterile Components

Figure 10A:
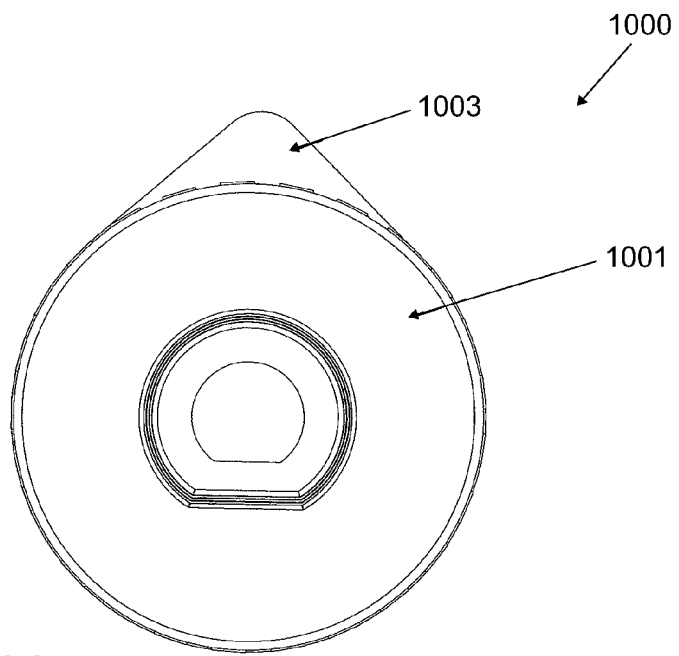
FIGS. 10A-10C depict an example of sterile packaging for a disk assembly component.
Figure 10B:
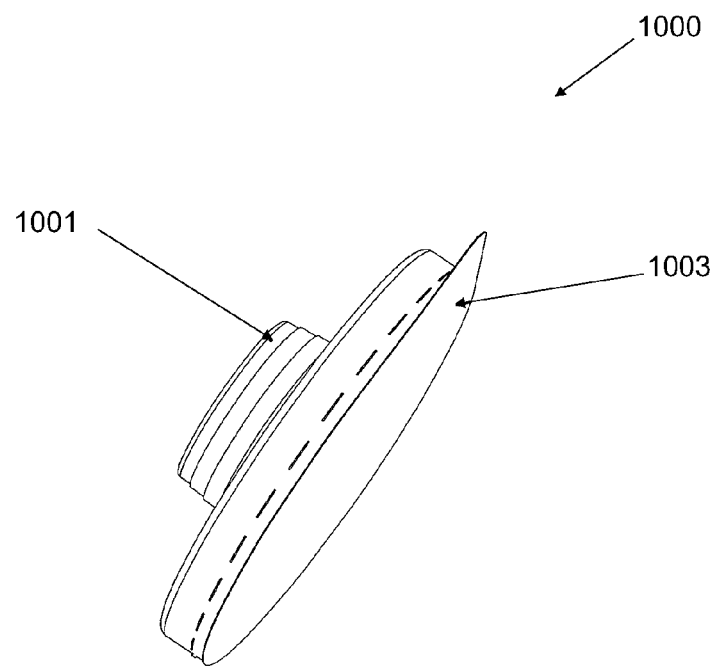
Figure 10C:
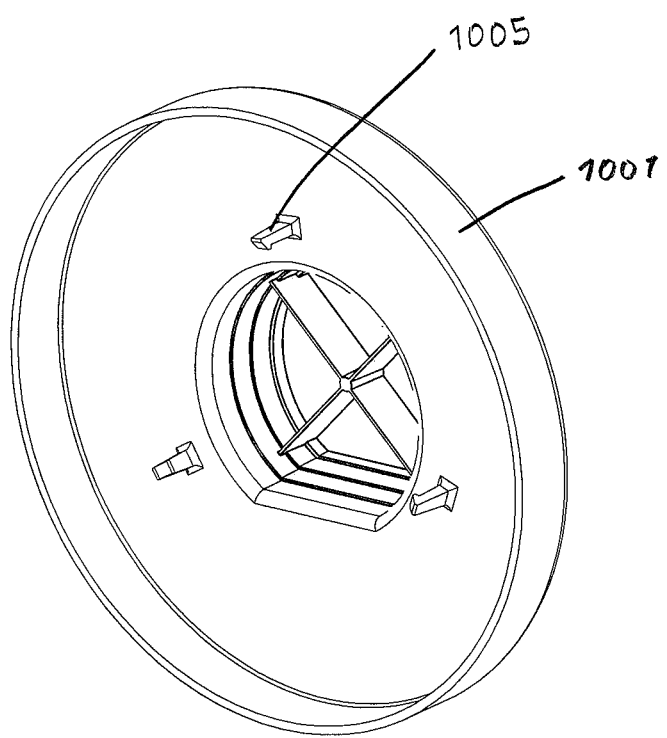

In some variations of a fluid monitoring system, the fluid that is monitored is patient blood. In such variations, the components that contact the patient's blood may be sterile to reduce the risk of contamination to the patient. A component may be manufactured using a sterile process and facility, or may undergo a sterilization process post-manufacture. In either case, the component may be packaged to preserve sterility. Some fluid monitoring systems may be manufactured and assembled in a sterile environment, or may be assembled, then sterilized. In some variations, not all components of the fluid monitoring system are sterilized. For example, the fluid lines in the PL and housing may be sterile, but the transfer disk and/or the sensor disk may not be sterile. A barrier, such as a sterile membrane or a gap, may be imposed between sterile and non-sterile components to reduce and/or eliminate contact between components. In some cases, the barrier may be temporary, such as packaging that is removed upon installation, or permanent, such as air space between components. In other cases, the barrier gap may be permanent, such as protrusions or spacers that provide permanent clearance between sterile and non sterile components. Additional steps may be taken during manufacture and installation to protect sterilized components from contamination by non-sterile components. For example, the packaging of a sterile PL and housing or disk assembly may be sized and shaped so that the component can be handled and installed without contamination, as shown in FIGS. 10A and 10B. Packaging (1000) may be used to protect the sterility of any system component, such as a PL cartridge or disk assembly. Packaging (1000) may comprise a tray (1001) and lid (1003). The tray may be molded into a shape that fits the contours of the component it is intended to house, for example, the circular tray (1001) may be suitable for housing a component of the disk assembly, such as the transfer disk or sensor disk, and may be made of any material that provides sufficient structural integrity to encase the enclosed component, such as high-density polyethylene (HDPE) or poly propylene. Some variations of a tray may comprise latches or snap closures (1005) that retain the component within the tray, as shown in FIG. 10C. Once the component is placed inside tray (1001), the lid (1003) may be sealed over the component. The lid (1003) may be made of any suitable material that can be effectively sealed and bonded with the tray material, such as Tyvek for a HDPE tray, or polycoated foil lid stock. The seal between lid (1003) and tray (1001) may be a heat seal, or an adhesive seal, according to the material composition of the lid and tray. Prior to installation, the lid (1003) may be removed, exposing the alignment and locking features of the component, while the component remains seated (and engaged by latches (1005)) within the tray (1001). The latches (1005) or any alternate coupling mechanism is configured to engage the component to the tray (1001) in a manner that prevents a user from separating the component from the tray, and thus preventing use of the component in a manner that would compromise sterility. The tray (1001) may then be gripped to guide the component to the appropriate installation site, and manipulated so that the alignment and locking features of the component are fully engaged with the monitoring system. Full engagement and alignment with the fluid monitoring system may urge the latches in the tray to disengage the component. The tray (1001) may then be dissociated from the component and discarded. Other variations of packaging (1000) and methods of installation may be used as appropriate for the component to be installed, where the packaging and method of handling reduces the contact of non-sterile items with the sterile component and may eliminate contamination by non-sterile components along a sterile fluid pathway. During the manufacturing process, the different components may be treated and packaged separately. For example, the transfer disk may be sterilized via gamma irradiation, however, the sensor disk may not be sterilized. Directly prior to use, the transfer disk and sensor disk may be assembled in the same clean room, even those they are packaged separately.

Figure 11A:
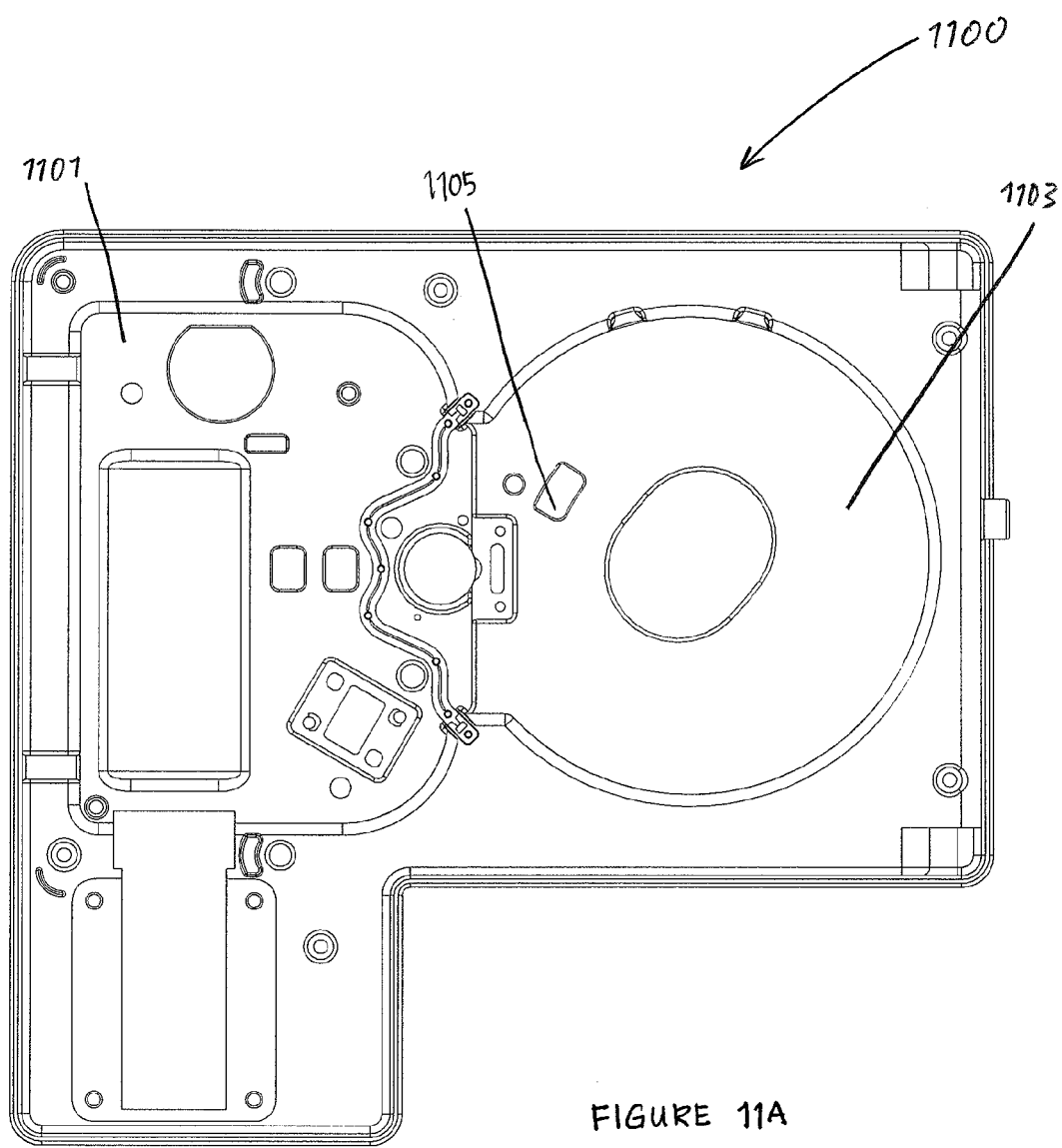
FIGS. 11A-11B depict a variation of the system interface for the patient line and housing and disk assembly.
Figure 11B:
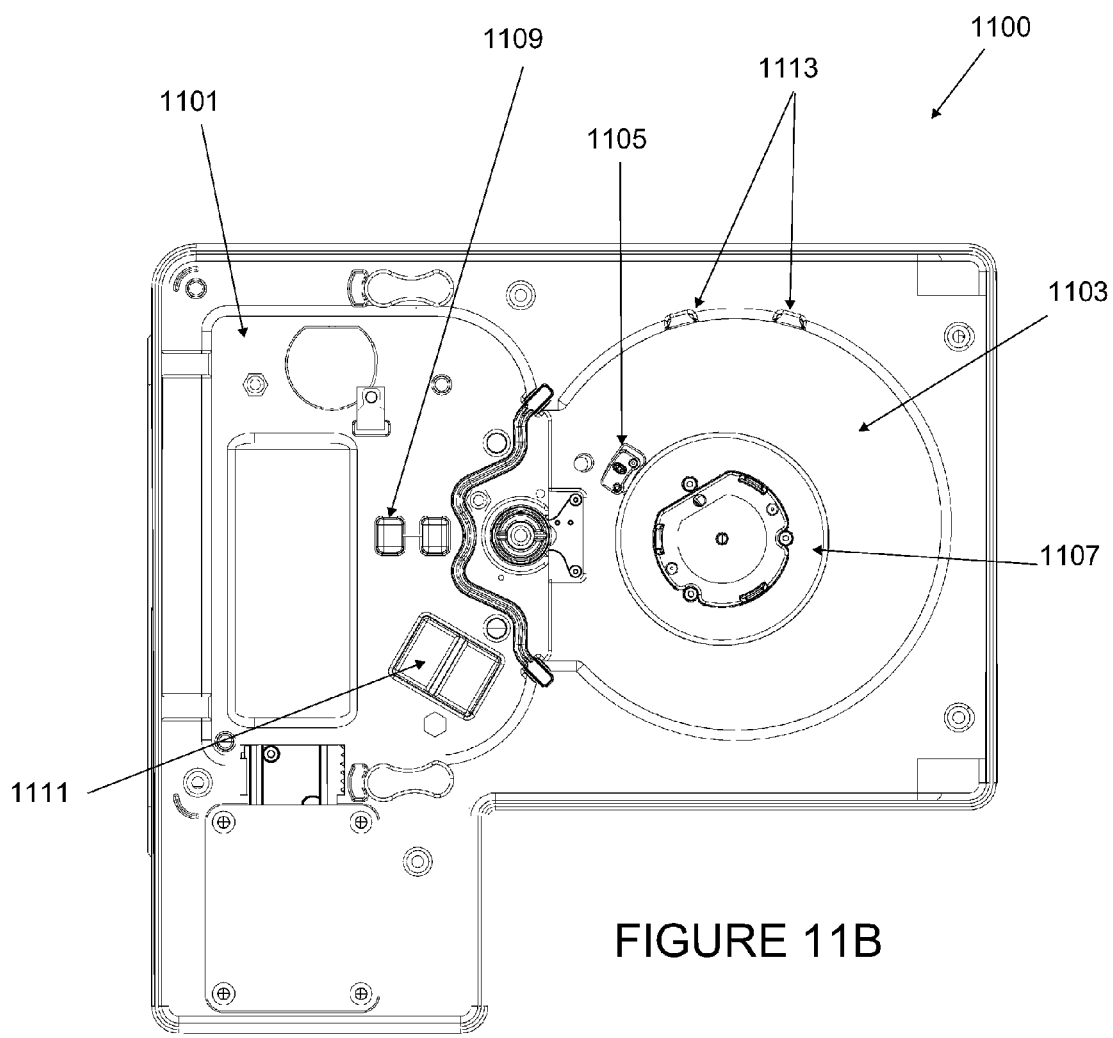

The fluid monitoring system interface with the PL cartridge and disk assembly may have any suitable shape and size, with the appropriately aligned pins and recesses to accommodate the PL cartridge and disk assembly. One variation of an interface (1100) is shown in FIGS. 11A-11B. The system interface (1100) has a recess (1101) for the installation of PL cartridge (200), and has a recess (1103) for the installation of disk assembly (300). There may also be additional recesses of varying shapes and sizes to accommodate additional system components, as well as apertures and snap closure to keep the PL cartridge and/or disk assembly components from disengaging from the system during use. The interface (1100) may also comprise sensor access apertures (1105) for ready access to the disk assembly. The blood-in-line, air-in-line, humidity and other sensor types may access the disk assembly through apertures such as (1109), (1111), and (1113) respectively.

FIG. 11B shows the housing provided by the fluid monitoring system, wherein the syringe may be installed prior to the PL cartridge (200). The recess (1103) may also comprise a protrusion that articulates with the alignment features in the transfer disk (302). In this embodiment, the system interface (1100) is configured for the vertical installation of the disk assembly, but in other embodiments, the disk assembly may be oriented horizontally, or any position between the two. The intersection between recess (1101) and recess (1103) may be configured so that the disk assembly (300) and the PL cartridge (200) may not contact each other when first installed, however a variety of actuators may be used to adjust the distance between the disk assembly and PL cartridge.

What is claimed as new and desired to be protected by Letters Patent of the United States is:

1. A fluid sensor device, comprising:
    a plurality of transfer reservoirs, each transfer reservoir comprising an optically transmissive material, an inlet opening, an outlet opening, and a cavity comprising a deformable wall and a light-reflecting structure; and
    a plurality of alignment structures, wherein at least one alignment structure is associated with each transfer reservoir.

2. The fluid sensor device of claim 1, wherein the deformable walls of the plurality of transfer reservoirs are deformable membranes.

3. The fluid sensor device of claim 1, wherein the cavities of the plurality of transfer reservoirs further comprise a fixed wall.

4. The fluid sensor device of claim 1, wherein the plurality of transfer reservoirs are located in a circular transfer cartridge and wherein the inlet openings of the plurality of transfer reservoirs are located on the outer circumferential surface of the circular transfer cartridge.

5. The fluid sensor device of claim 1, further comprising a sensor cartridge interface.

6. The fluid sensor device of claim 5, wherein the sensor cartridge interface comprises an alignment structure and at least one locking structure.

7. The fluid sensor device of claim 6, wherein the sensor cartridge interface further comprises a plurality of sensor substrate access apertures.

8. The fluid sensor device of claim 6, further comprising a sensor cartridge comprising a transfer cartridge interface complementary to the sensor cartridge interface of the transfer cartridge.

9. The fluid sensor device of claim 8, wherein the sensor cartridge further comprises a plurality of test strips.

10. The fluid sensor device of claim 8, wherein the sensor cartridge further comprises a plurality of fluid sample receiving regions, a plurality sensor substrates and a plurality of sensor electrode contacts.

11. The fluid sensor device of claim 8, wherein the plurality of fluid sample receiving regions are oriented to correspond to the outlet openings of transfer reservoirs when the transfer cartridge and sensor cartridge are attached.

\* \* \* \* \*